US011723808B2

(12) United States Patent
Burnet et al.

(10) Patent No.: US 11,723,808 B2
(45) Date of Patent: Aug. 15, 2023

(54) DETECTING MICROBIAL INFECTIONS IN WOUNDS

(71) Applicants: CONVATEC TECHNOLOGIES INC., Las Vegas, NV (US); SYNOVO GMBH, Tübingen (DE); QUALIZYME DIAGNOSTICS GMBH AND CO KG, Graz (AT)

(72) Inventors: Michael Burnet, Tübingen (DE); Philip Bowler, Appleton (GB); Sarah Wroe, Manchester (GB); Jade Steven, Ellesmere Port (GB); Daniel Metcalf, Sale (GB); David Parsons, West Kirby (GB); Lucy Ballamy, Llangollen (GB); Andrea Heinzle, Gratwein-Strassengel (AT); Eva Sigi, Sankt Barbara im Mürztal (AT); Daniel Luschnig, Graz (AT); Clemens Gamerith, Graz (AT)

(73) Assignees: CONVATEC TECHNOLOGIES INC., Las Vegas, NV (US); SYNOVO GMBH, Tübingen (DE); QUALIZYME DIAGNOSTICS GMBH AND CO KG, Graz (AT)

( * ) Notice: Subject to any disclaimer, the term of this patent is extended or adjusted under 35 U.S.C. 154(b) by 169 days.

(21) Appl. No.: 17/397,462

(22) Filed: Aug. 9, 2021

(65) Prior Publication Data

US 2021/0361490 A1 Nov. 25, 2021

Related U.S. Application Data

(63) Continuation of application No. 16/090,045, filed as application No. PCT/US2017/024991 on Mar. 30, 2017, now abandoned.

(Continued)

(51) Int. Cl.
*A61F 13/00* (2006.01)
*A61L 15/38* (2006.01)
(Continued)

(52) U.S. Cl.
CPC ........ *A61F 13/00051* (2013.01); *A61B 5/445* (2013.01); *A61L 15/38* (2013.01);
(Continued)

(58) Field of Classification Search
CPC ................. A61B 5/445; A61F 13/0051; A61F 2013/00429; A61L 15/16; A61L 15/38;
(Continued)

(56) References Cited

U.S. PATENT DOCUMENTS 4,087,327 A * 5/1978 Feder .................... C12M 29/16
435/399
7,611,860 B2 11/2009 Ferguson et al.
(Continued)

FOREIGN PATENT DOCUMENTS

EP 3187204 A1 7/2017
EP 3291849 B1 9/2021
(Continued)

OTHER PUBLICATIONS

Ausbalian Examination Report No. 1, IP Australia, Australian Patent Application No. 2017239643, dated Apr. 1, 2021, 5 pages.
(Continued)

*Primary Examiner* — Kaylee R Wilson
*Assistant Examiner* — Raymond P Dulman
(74) *Attorney, Agent, or Firm* — Taft Stettinius & Hollister LLP; Ryan O. White; Derek B. Lavender

(57) ABSTRACT

Provided herein are microbial infection indicator devices, including dressing with indicators, standalone indicator inserts or disks that can be freely placed at a wound site or dressing, and applications thereof for displaying a visible or
(Continued)

detectable signal to a user upon detection of an analyte or biomarker indicative of an infection, such as a color change.

11 Claims, 39 Drawing Sheets

Related U.S. Application Data

(60) Provisional application No. 62/315,565, filed on Mar. 30, 2016.

(51) Int. Cl.
| | | |
|---|---|---|
| *A61L 15/56* | (2006.01) | |
| *G01N 33/00* | (2006.01) | |
| *A61B 5/00* | (2006.01) | |
| *A61B 10/00* | (2006.01) | |
| *A61F 13/84* | (2006.01) | |
| *C12Q 1/37* | (2006.01) | |

(52) U.S. Cl.
CPC .............. *A61L 15/56* (2013.01); *G01N 33/00* (2013.01); *A61B 10/0045* (2013.01); *A61F 2013/00429* (2013.01); *A61F 2013/8473* (2013.01); *C12Q 1/37* (2013.01)

(58) Field of Classification Search
CPC ...... C12Q 1/37; G01N 33/569; G01N 33/573; G01N 33/68
See application file for complete search history.

(56) References Cited

U.S. PATENT DOCUMENTS

| | | |
|---|---|---|
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Lauren sou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |

(56) References Cited

U.S. PATENT DOCUMENTS

| | | |
|---|---|---|
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,096,829 B2 | 8/2021 | Robinson et al. |
| 11,229,719 B2 | 1/2022 | Locke et al. |
| 2005/0079542 A1 | 4/2005 | Cullen |
| 2005/0106713 A1 | 5/2005 | Phan |
| 2006/0034816 A1 | 2/2006 | Davis et al. |
| 2006/0155260 A1 | 7/2006 | Blott et al. |
| 2006/0172000 A1 | 8/2006 | Cullen et al. |
| 2007/0179373 A1 | 8/2007 | Pronovost et al. |
| 2007/0185426 A1 | 8/2007 | Ambrosio et al. |
| 2007/0219512 A1 | 9/2007 | Heaton et al. |
| 2007/0224084 A1 | 9/2007 | Holmes et al. |
| 2007/0239078 A1 | 10/2007 | Jaeb |
| 2007/0269851 A1 | 11/2007 | Sanders et al. |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coultharcl et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0129186 A1 | 5/2012 | Garcia et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2012/0264163 A1 | 10/2012 | Booher |
| 2012/0309036 A1 | 12/2012 | Gubitz et al. |
| 2013/0052653 A1 | 2/2013 | Stein et al. |
| 2013/0053795 A1 | 2/2013 | Coultharcl et al. |
| 2013/0123728 A1 | 5/2013 | Pratt et al. |
| 2013/0226063 A1 | 8/2013 | Taylor et al. |
| 2013/0252231 A1* | 9/2013 | Albrecht .......... G01N 33/56983 435/5 |
| 2013/0261409 A1 | 10/2013 | Pathak et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0182157 A1 | 7/2015 | Boriah et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinsori et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |

(56) References Cited

U.S. PATENT DOCUMENTS

| | | |
|---|---|---|
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336348 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |

(56) References Cited

U.S. PATENT DOCUMENTS

| | | |
|---|---|---|
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvnen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0107964 A1 | 4/2020 | Locke et al. |
| 2020/0107965 A1 | 4/2020 | Greener |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121510 A1 | 4/2020 | Hartwell et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0155355 A1 | 5/2020 | Hill et al. |
| 2020/0155358 A1 | 5/2020 | Wheldrake |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179558 A1 | 6/2020 | Hubbell et al. |
| 2020/0179673 A1 | 6/2020 | Wan |
| 2020/0188180 A1 | 6/2020 | Akbari et al. |
| 2020/0188182 A1 | 6/2020 | Sanders et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Wate |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330264 A1 | 10/2020 | Locke et al. |
| 2020/0330283 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0322666 A1 | 10/2021 | Greener |
| 2021/0338487 A1 | 11/2021 | Robinson et al. |
| 2022/0105231 A1 | 4/2022 | Locke et al. |

FOREIGN PATENT DOCUMENTS

| | | |
|---|---|---|
| EP | 3936095 A1 | 1/2022 |
| EP | 3936163 A1 | 1/2022 |
| TW | 201201874 A | 1/2012 |
| TW | I385002 B | 2/2013 |
| WO | 9912581 A2 | 3/1999 |
| WO | 1999012581 A2 | 3/1999 |
| WO | 2005018543 A2 | 3/2005 |
| WO | 2011121394 A1 | 10/2011 |

(56) References Cited

FOREIGN PATENT DOCUMENTS

| | | |
|---|---|---|
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |

OTHER PUBLICATIONS

International Search Report, International Searching Authority, International Patent Application No. PCT/US2017/024991, dated Jul. 26, 2017, 3 pages.

International Preliminary Report on Patentability, International Searching Authority, International Patent Application No. PCT/US2017/024991, dated Oct. 2, 2018, 32 pages.

* cited by examiner

FIG. 1: Examples of engineered three-dimensional fabric structures, such as corrugations.
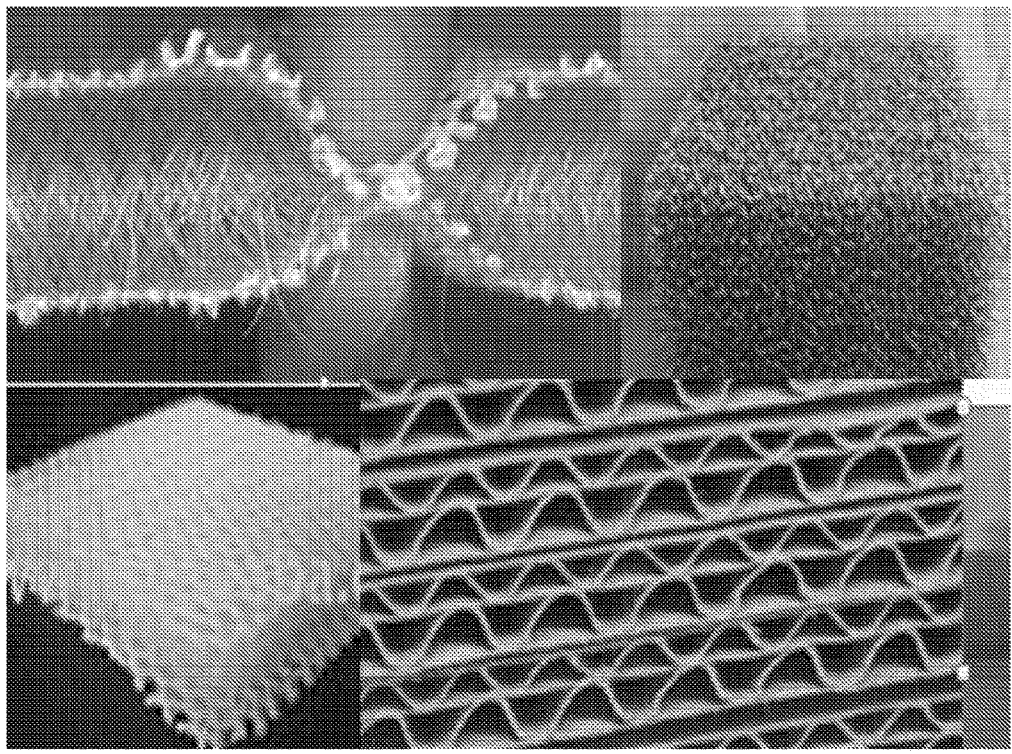

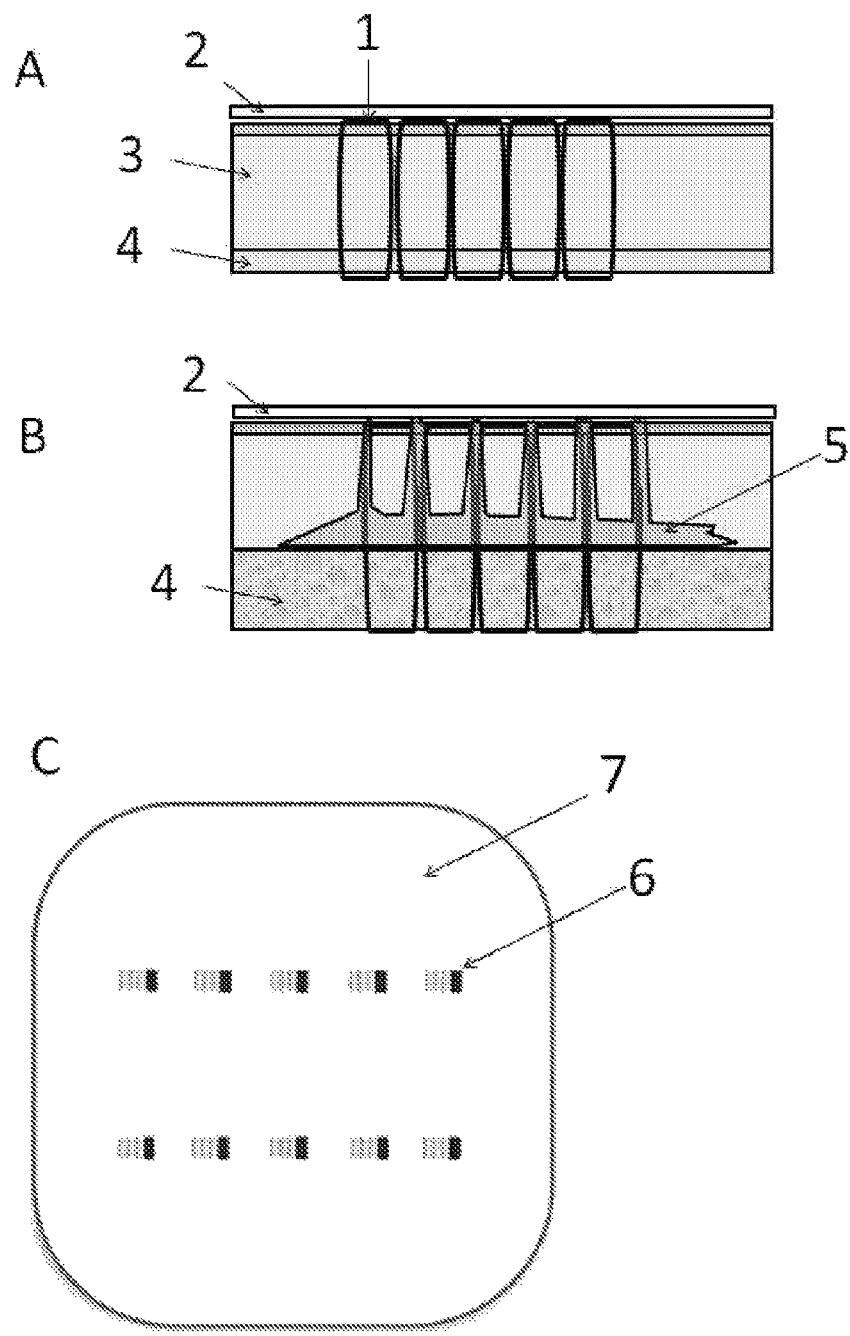
FIG. 2: Example of a dressing with AQUACEL

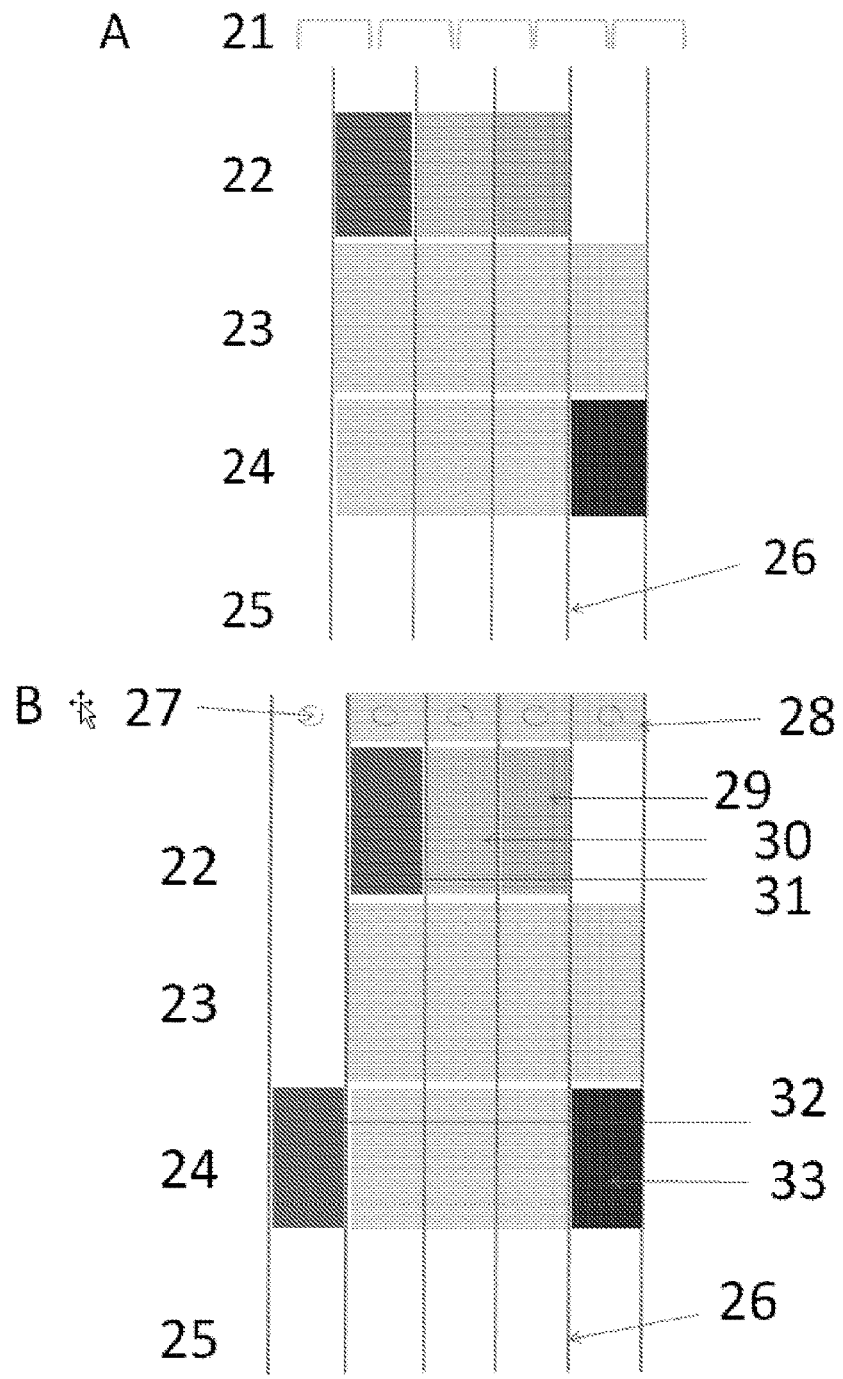
FIG. 3: Schematic of reaction cells

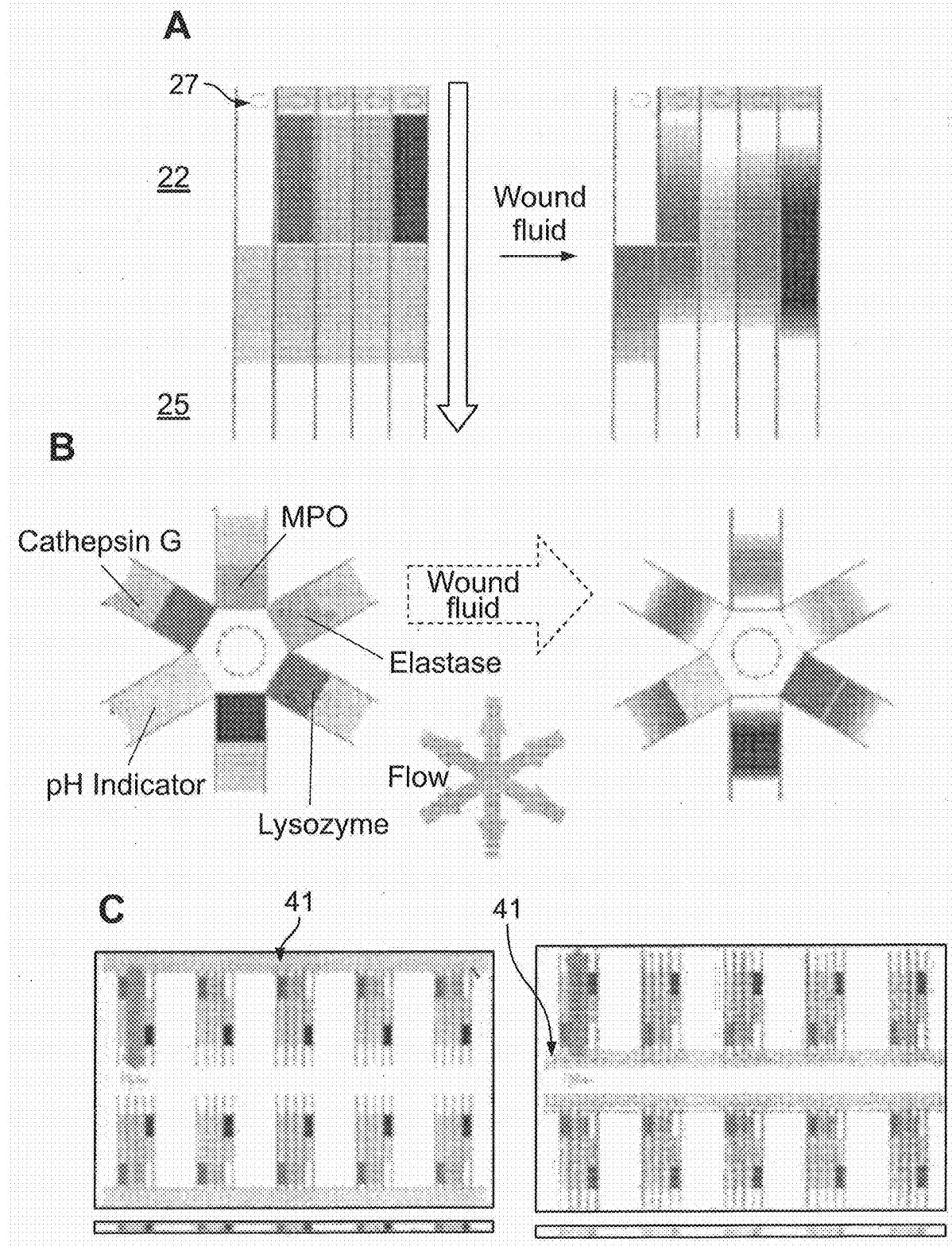
FIG. 4: Movement of indicators in reaction cells

FIG. 5: Radial arrangement of indicators
A.
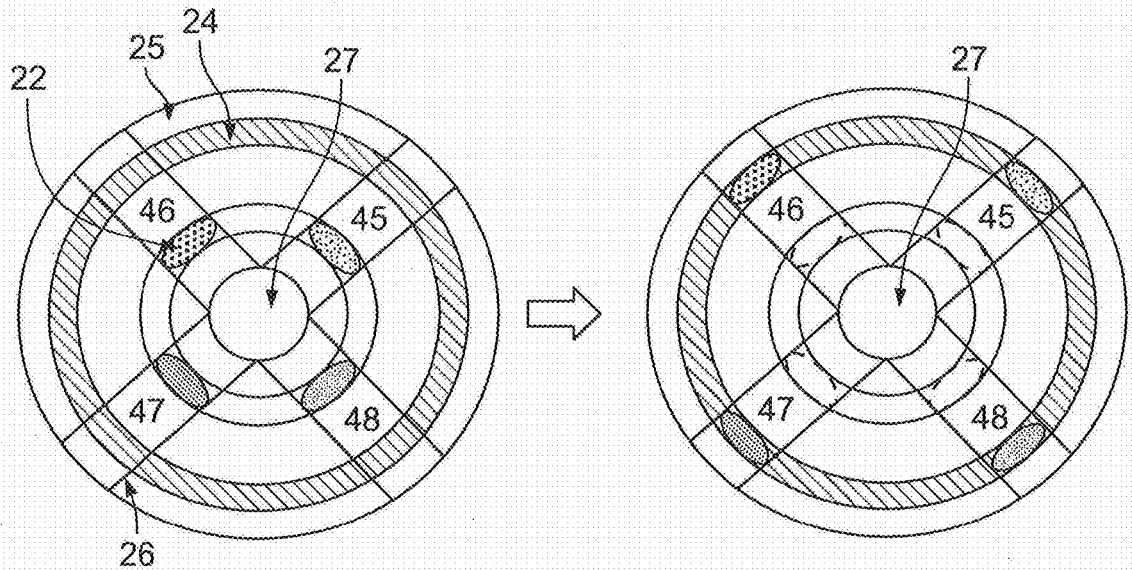
B.
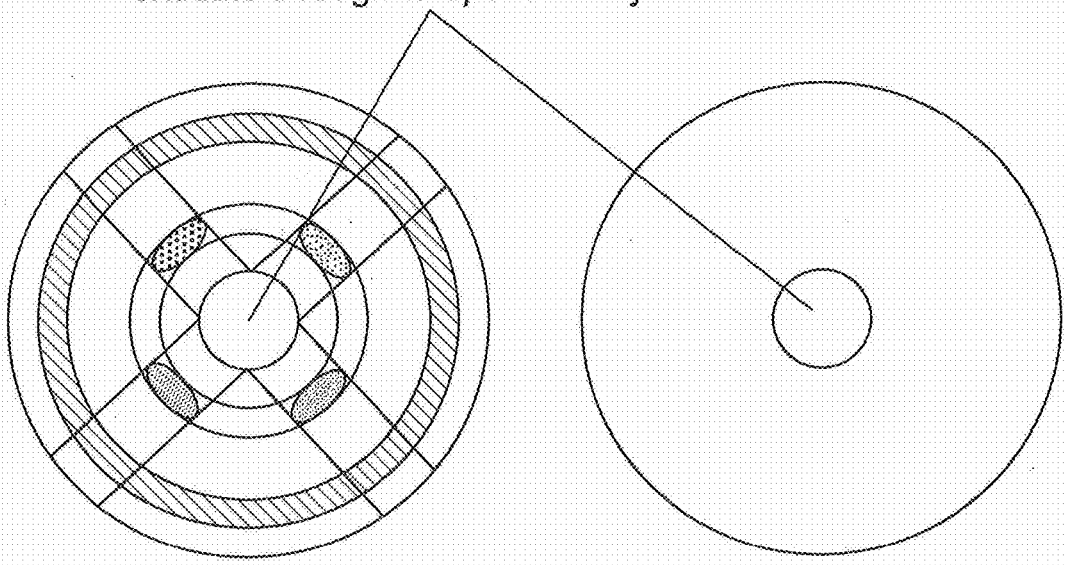

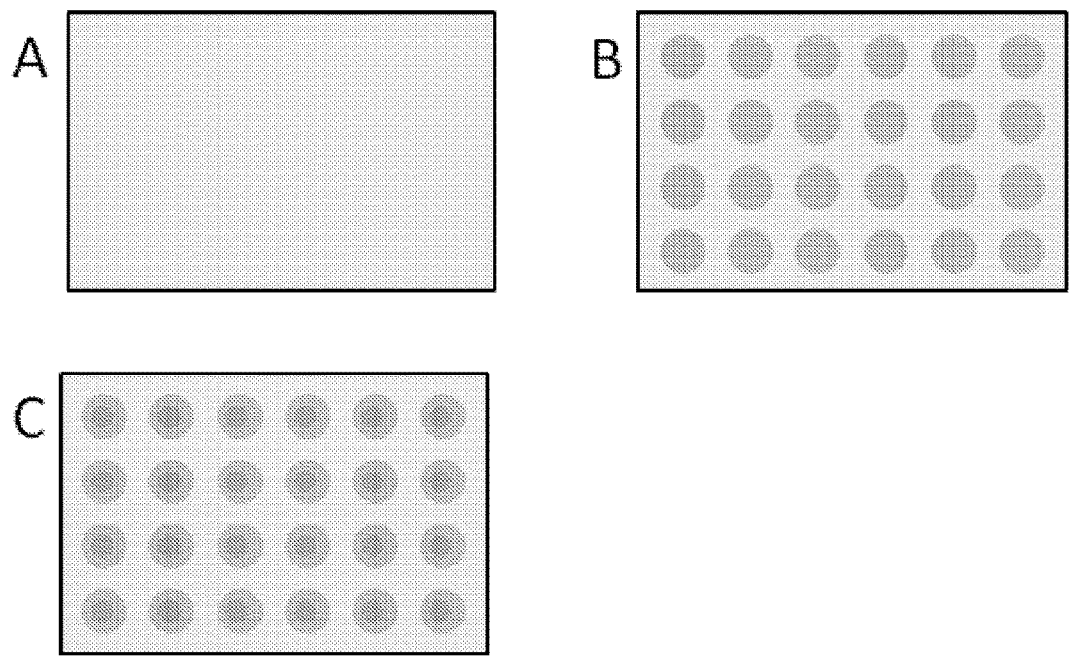
FIG. 6: Dressing printed for MPO detection

FIG. 7: In-place color development of MPO and elastase substrates on testing strips
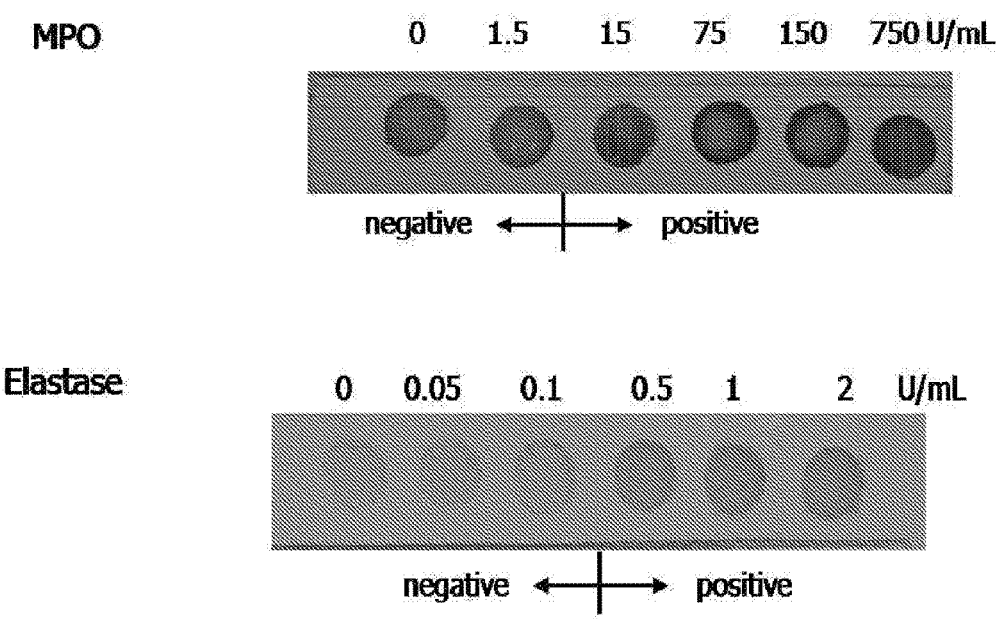

FIG. 8: Examples of substrates
A. MPO substrate (Fast Blue derivative)
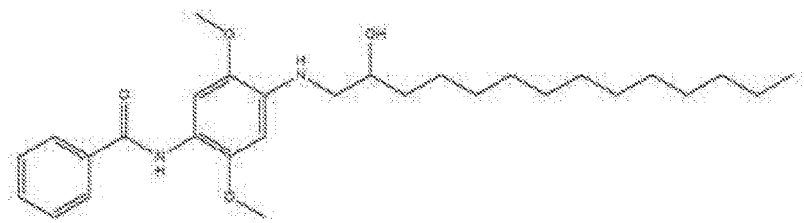
B. Elastase substrate
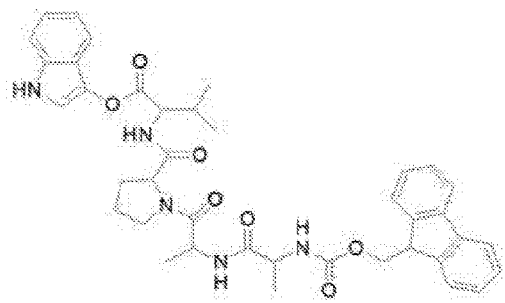
C. Oxidation to blue colored Indigo
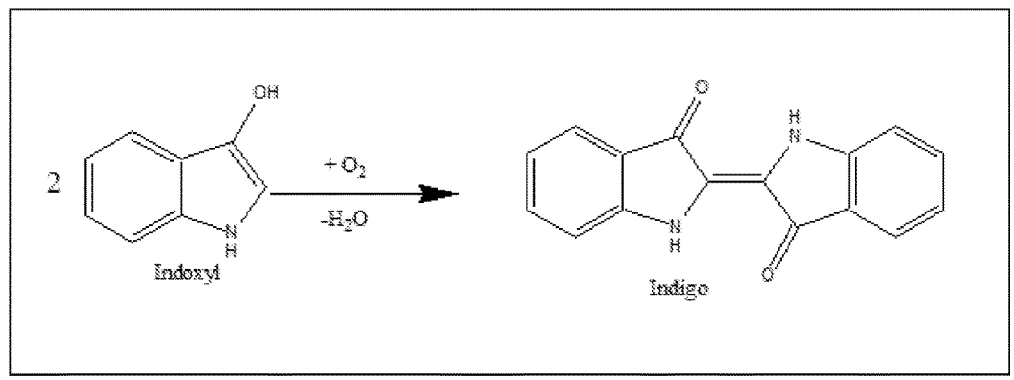

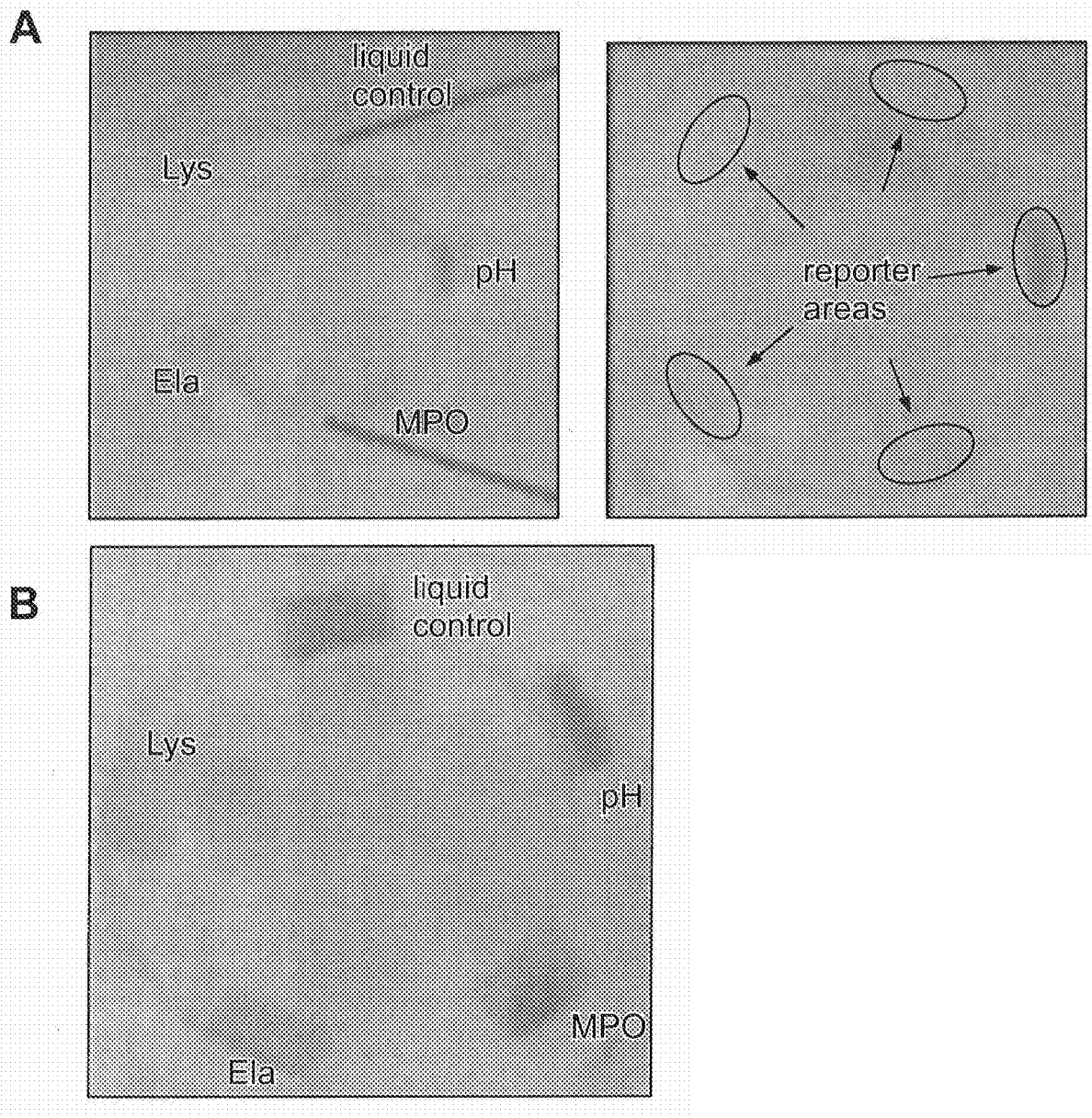
FIG. 9: In-place color development of different indicators in radial arrangement FIG. 10: Schematics of a radial indicator insert or disk
A
Top view:
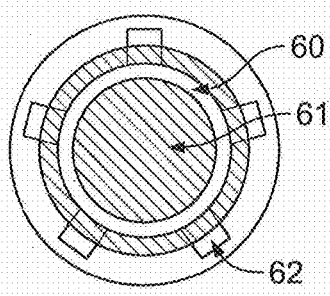
B
Layer 1: bottom layer
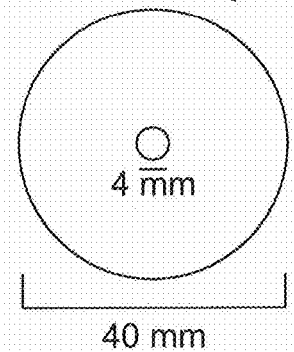
C
Layer 2: reaction material
a: adhesive
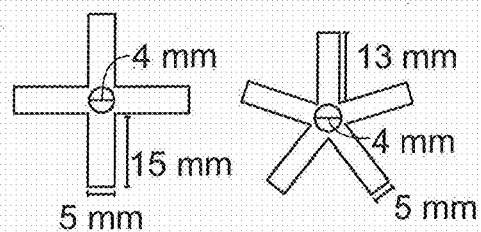
D
b: reaction layer
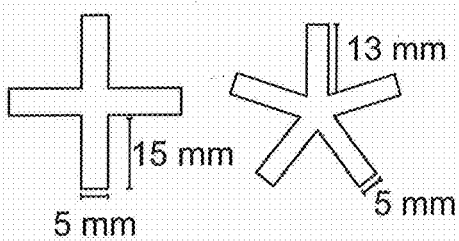
E
Layer 3: cover
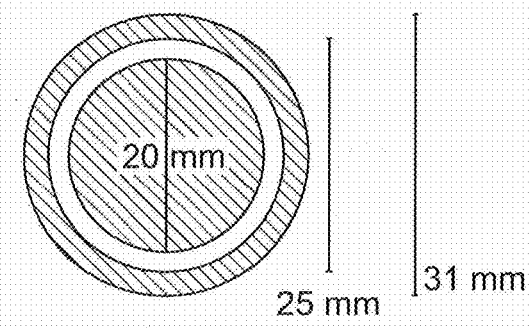

FIG. 11: Schematics of a radial indicator insert or disk with a window
A
Layer 1: bottom layer
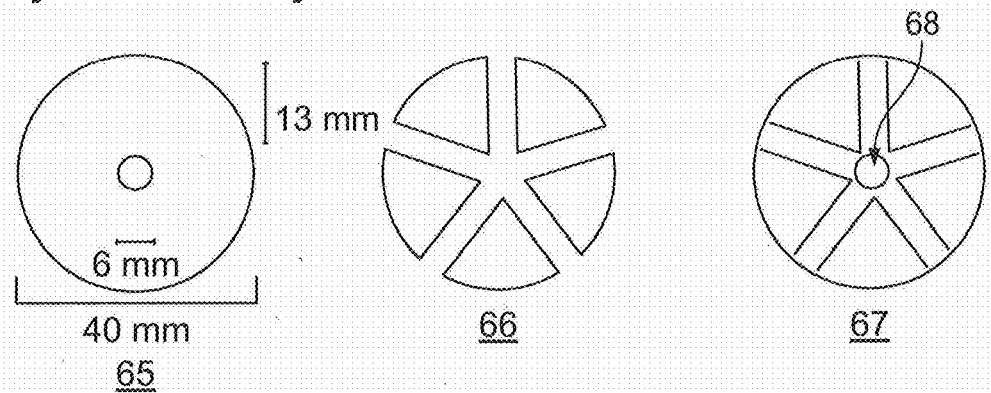
B
Layer 2: reaction material
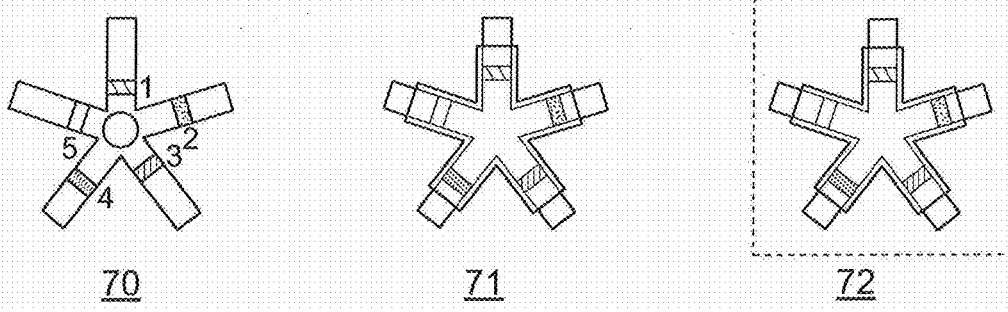

FIG. 12: Schematics of another embodiment of a radial indicator insert or disk
A  Layer 1: bottom layer
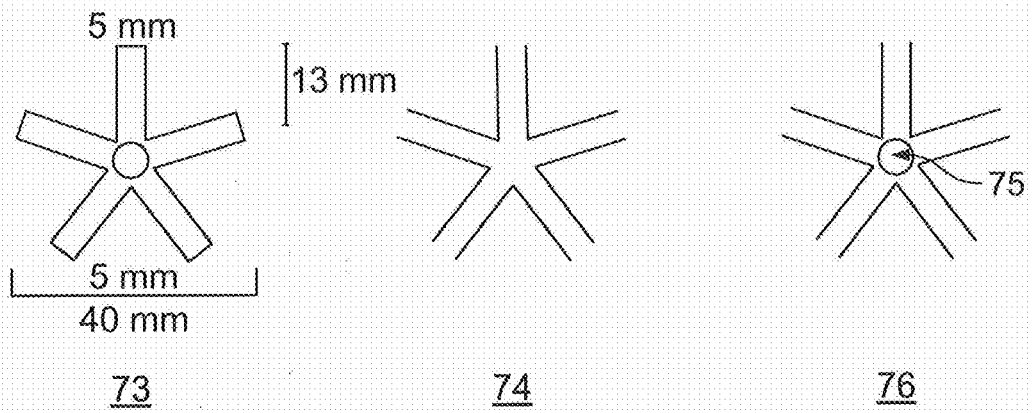
B  Layer 2: reaction material
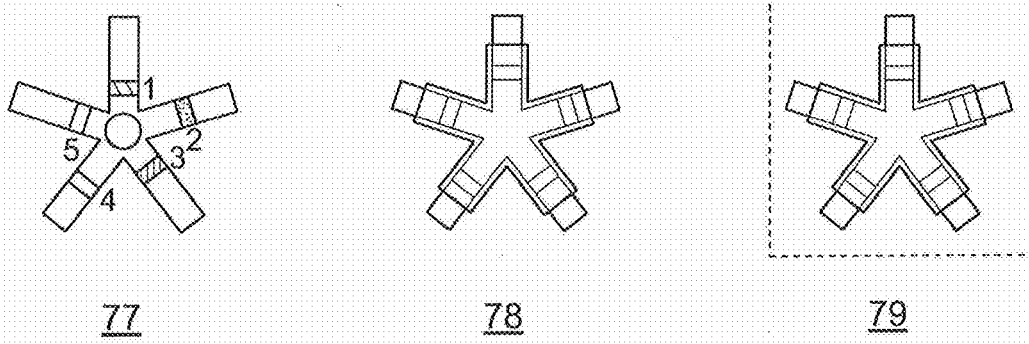

FIG. 13: Transport of Remazol Brilliant Blue
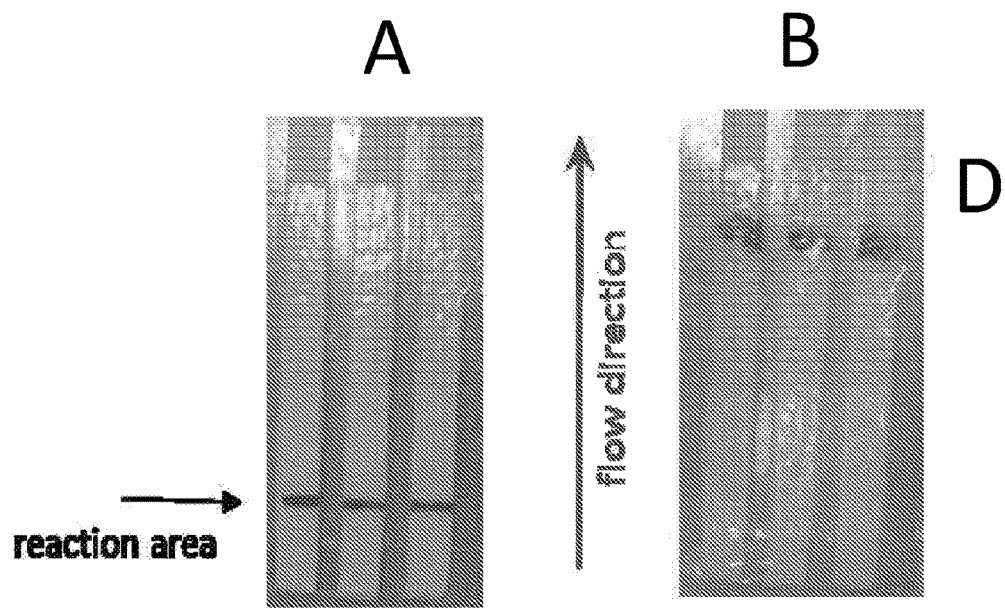

FIG. 14: Example of a pH indicator
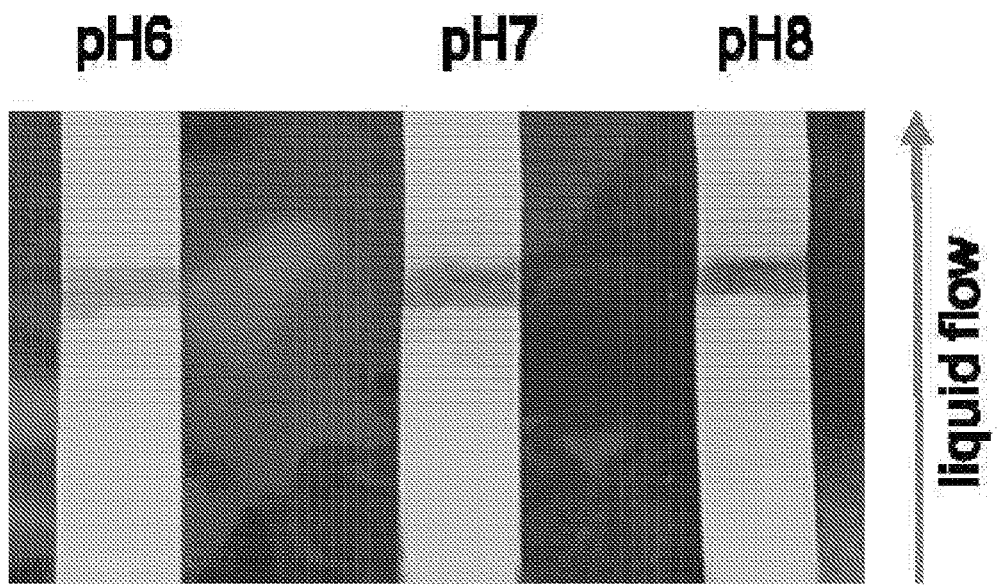

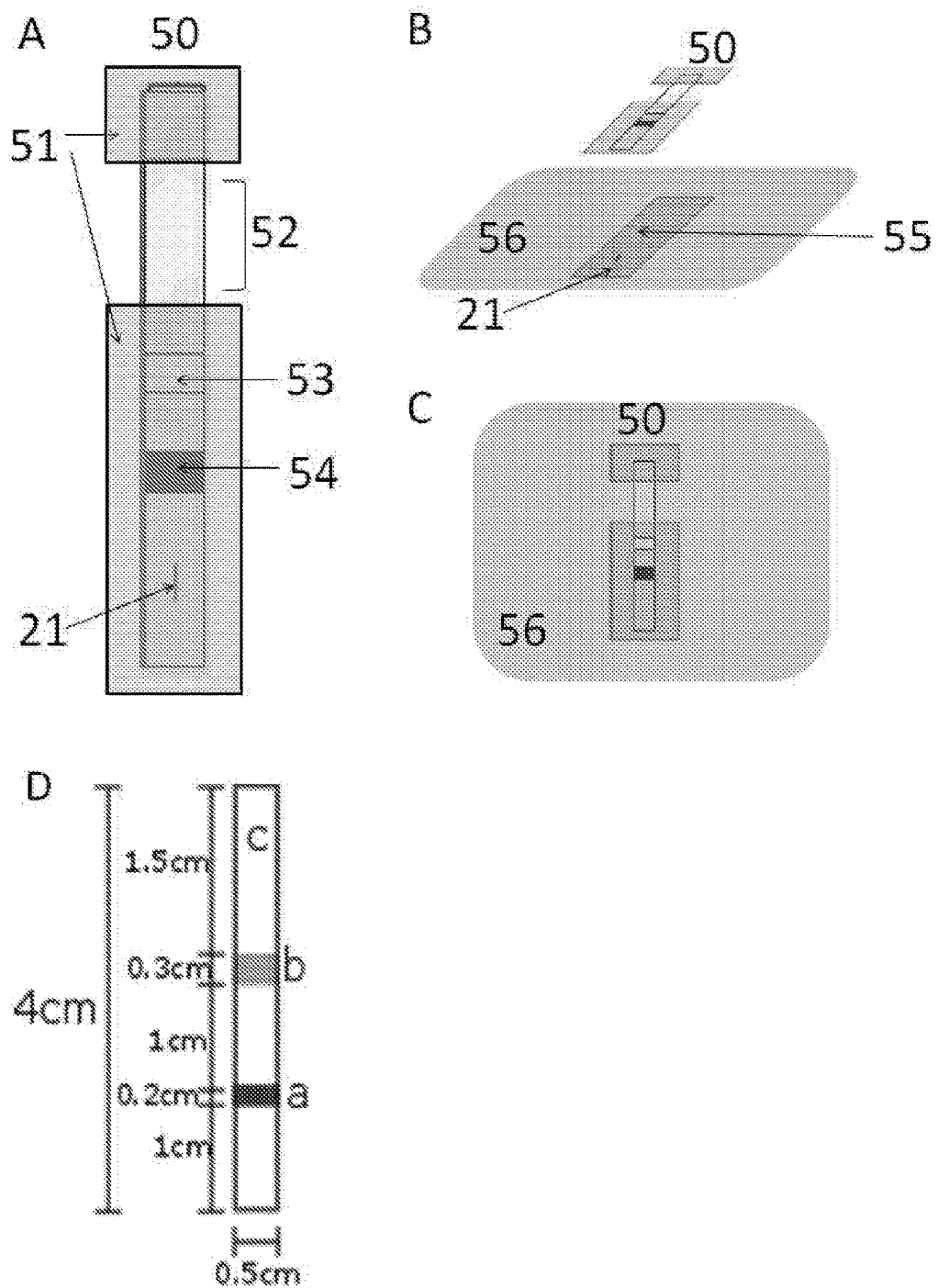
FIG. 15: Schematic of lysozyme test strip

FIG. 16: Examples of indicator substrates and reactions
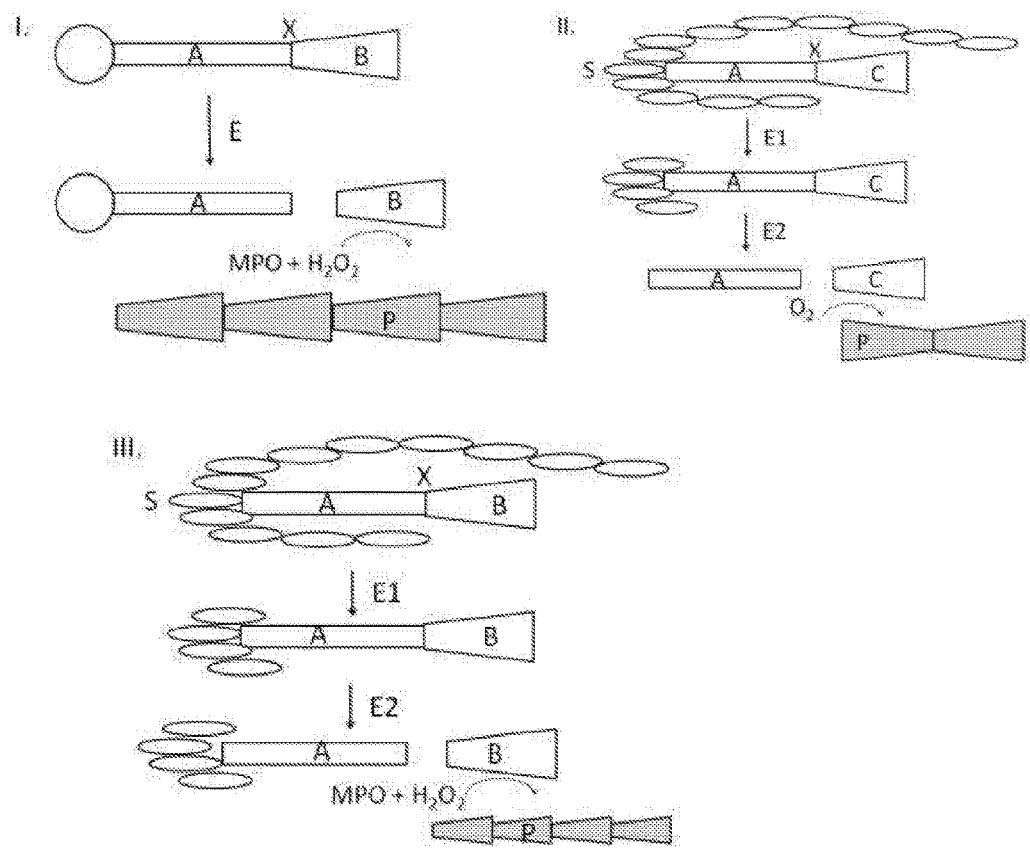

FIG. 17: Example of an indicator disk freely placed in a dressing
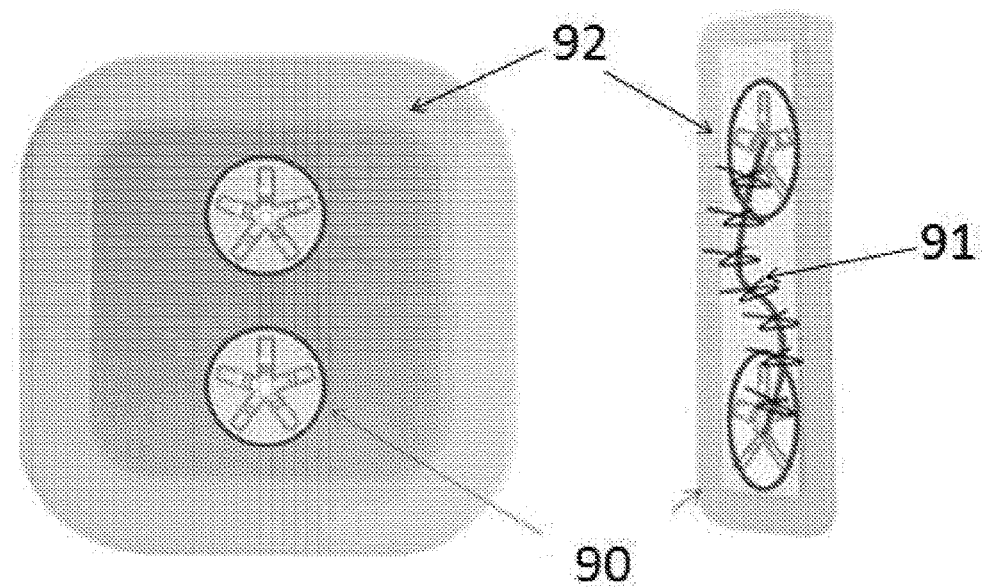

FIG. 18: Embodiments of diagnostic disks in non-woven layer in dressing
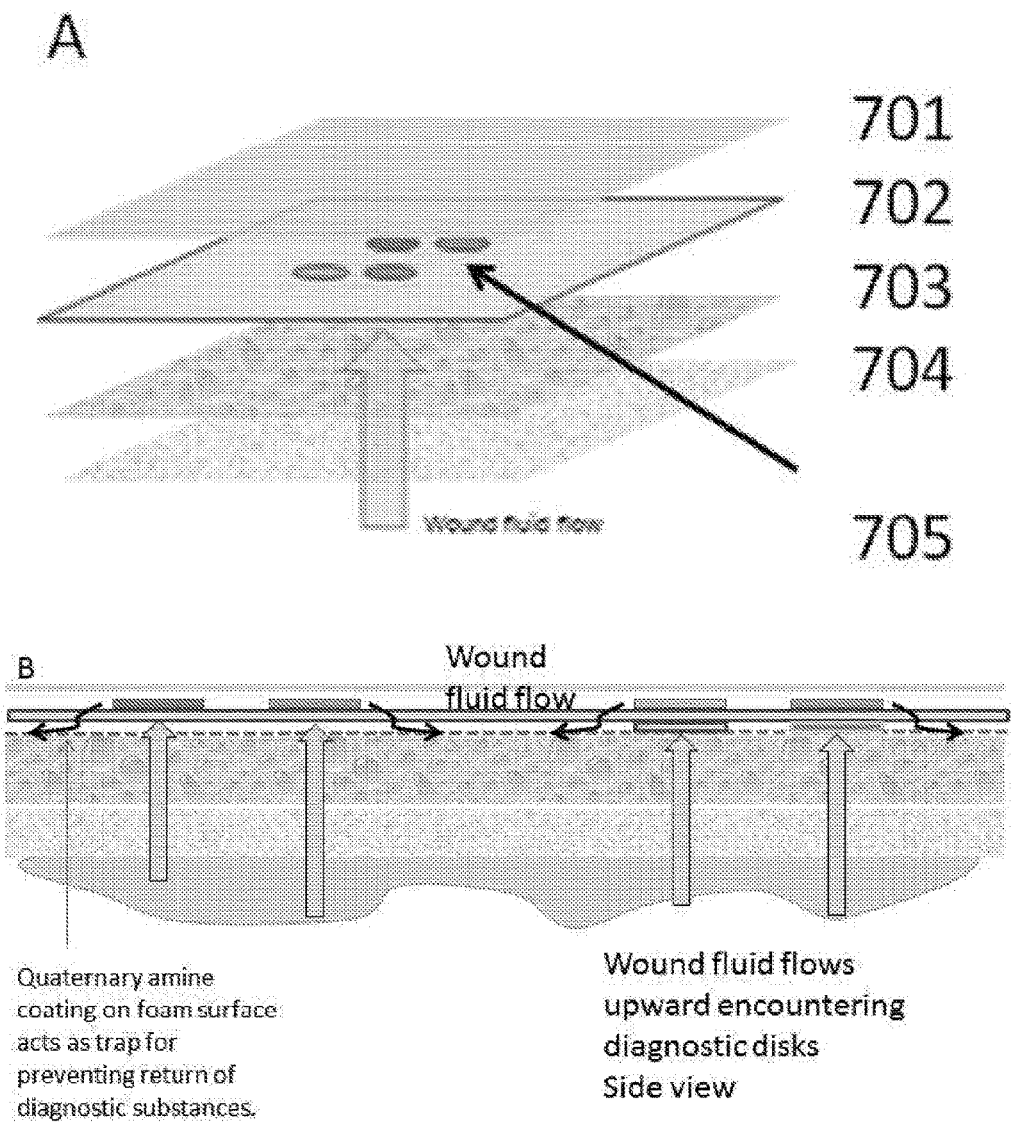

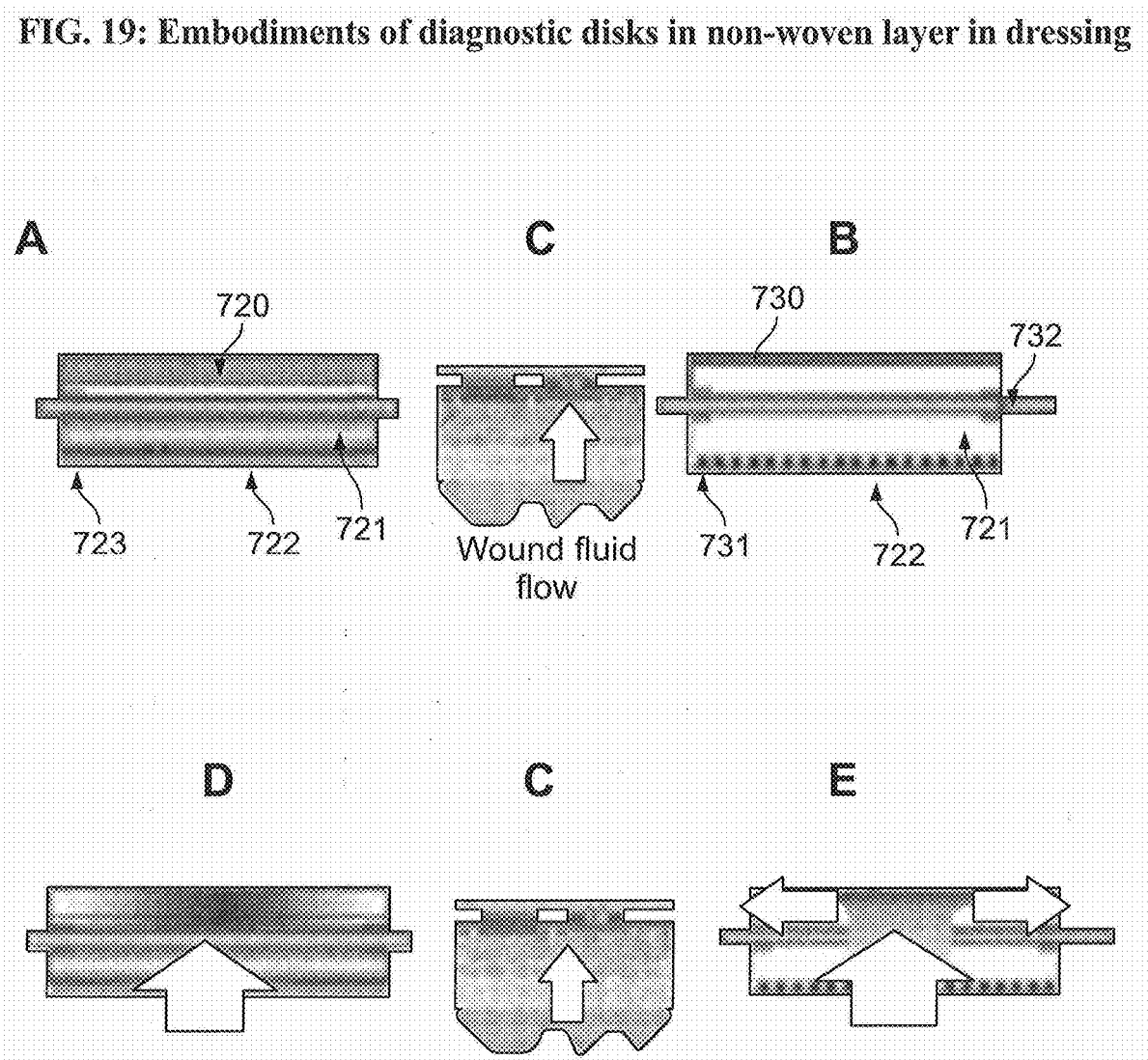
FIG. 19: Embodiments of diagnostic disks in non-woven layer in dressing

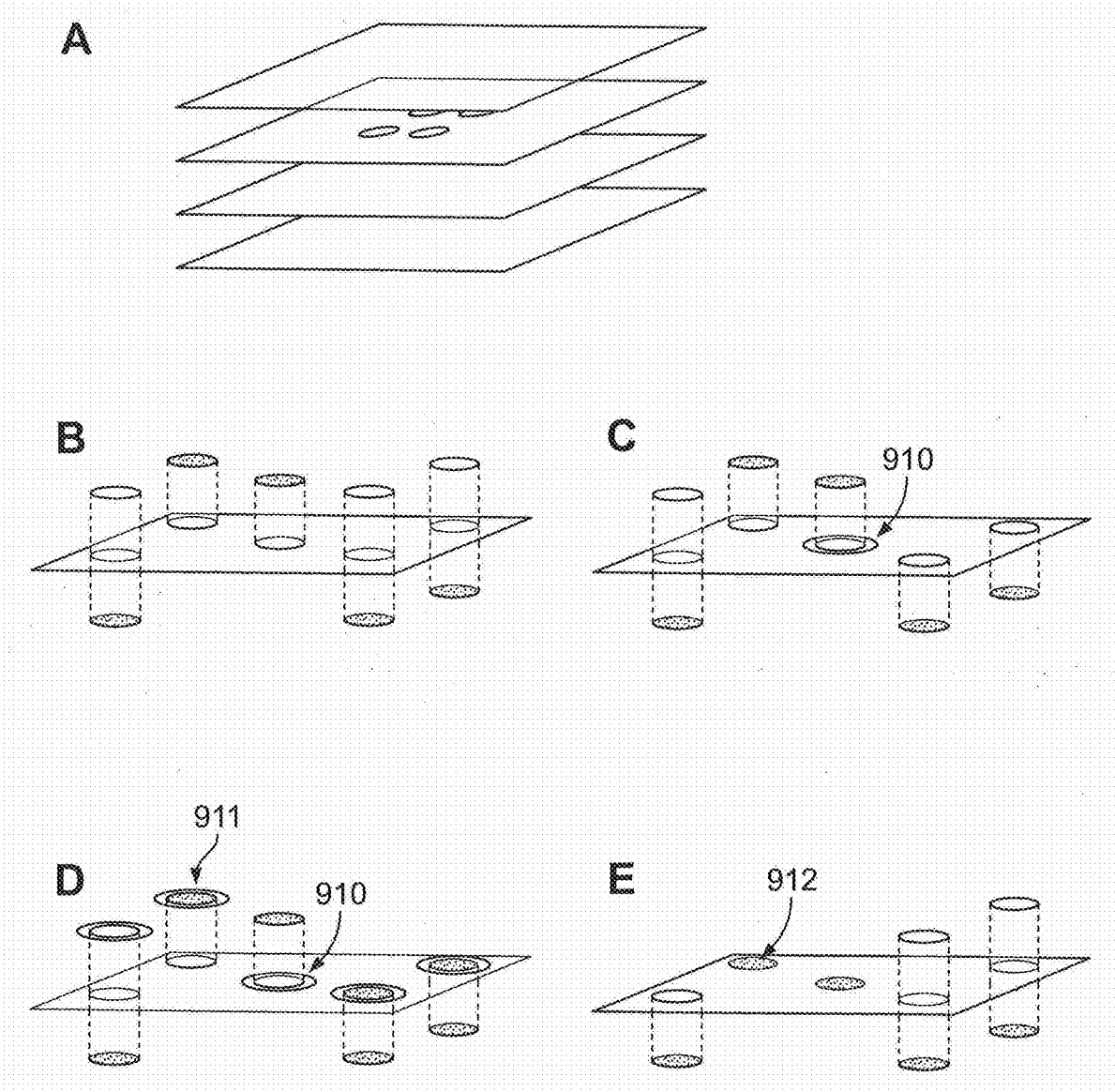
FIG. 20: Example of manufacturing diagnostic disks in sheets

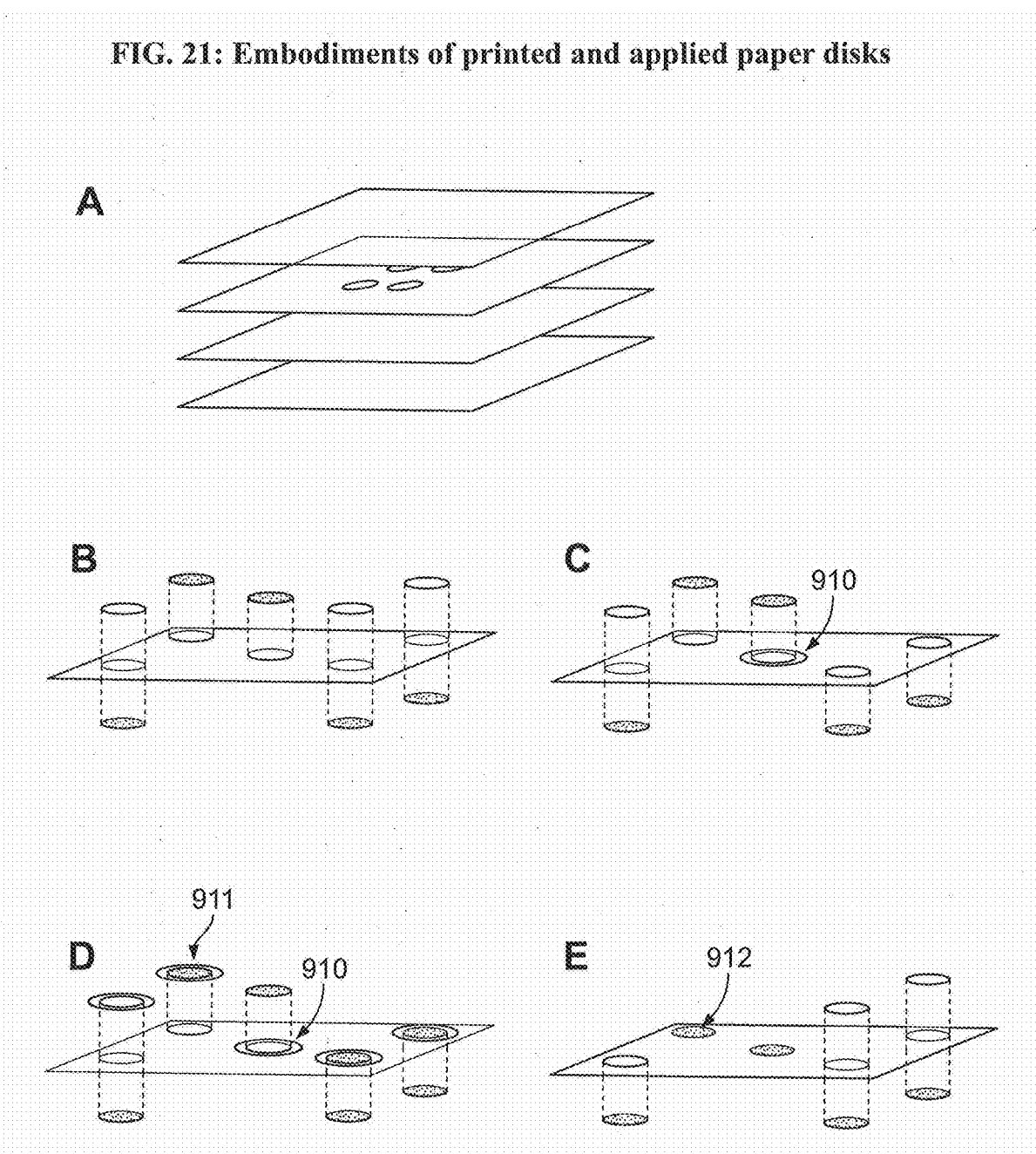
FIG. 21: Embodiments of printed and applied paper disks

FIG. 22: Methods of attaching or applying diagnostic disks to non-woven layer in dressing
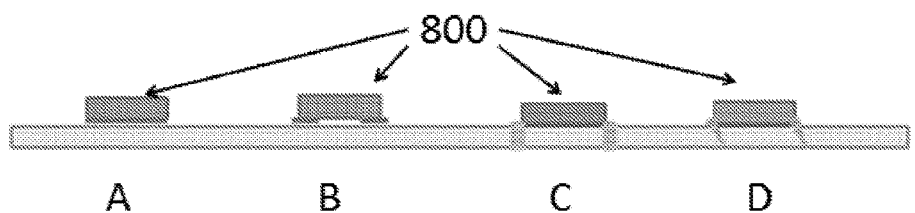

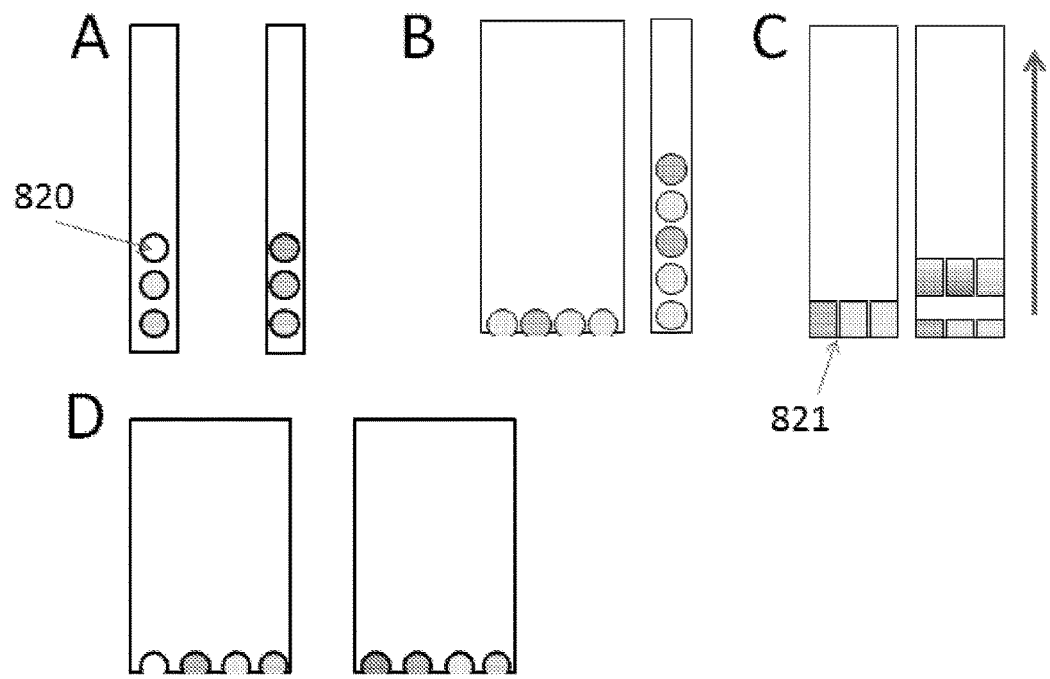
FIG. 23: Dipstick devices with indicator inserts or disks

FIG. 24: Sampling thread and use in dressing
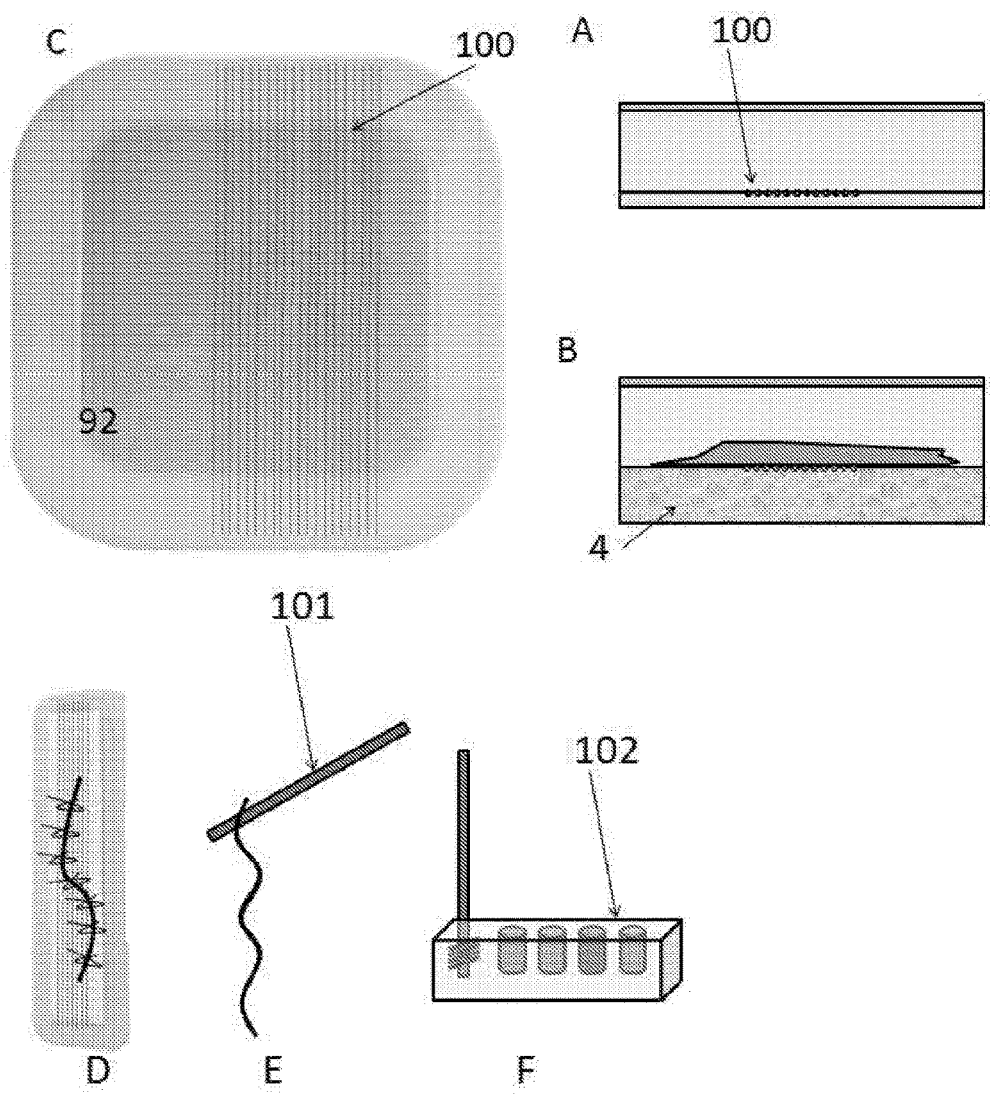

FIG. 25: Assembly for manufacturing indicator inserts
A 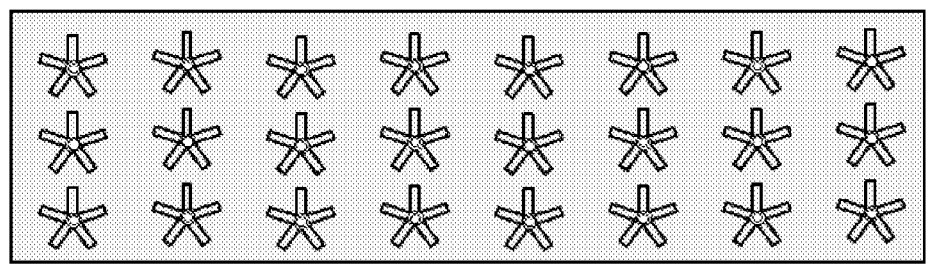
B 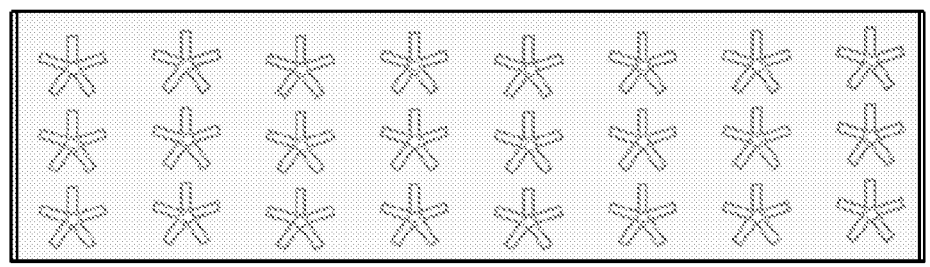
C 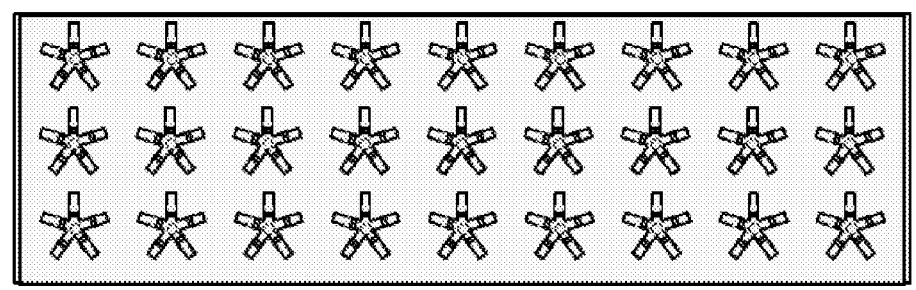
D 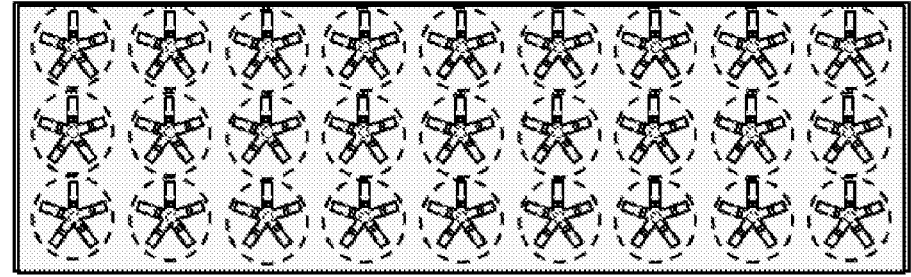

FIG. 26: Cross section of a standalone device kit
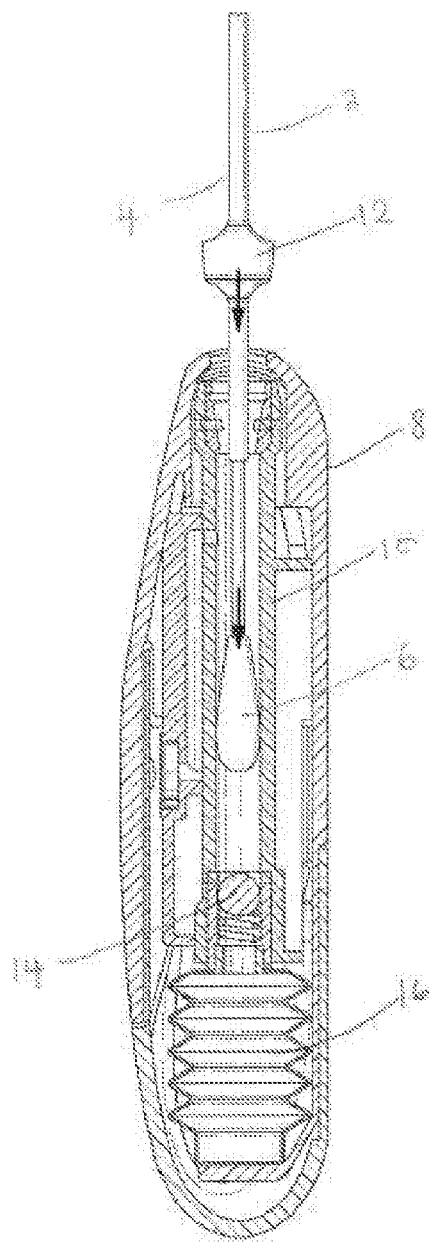

FIG. 27: Sampling tip inserted in the housing of standalone device kit
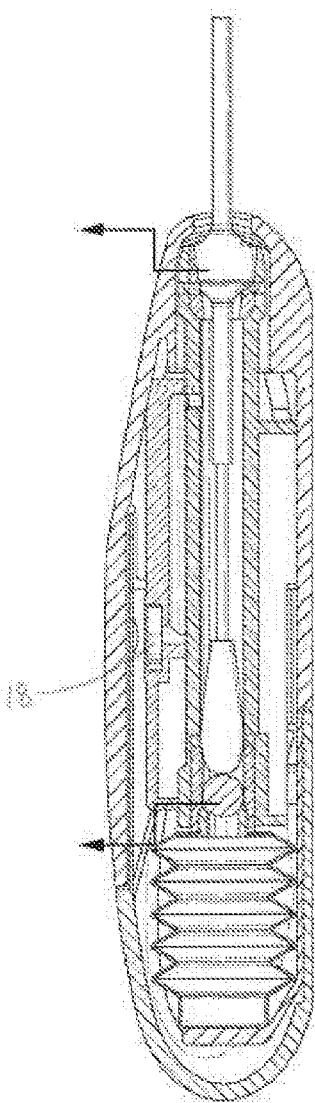

FIG. 28: A plan view of the standalone device kit
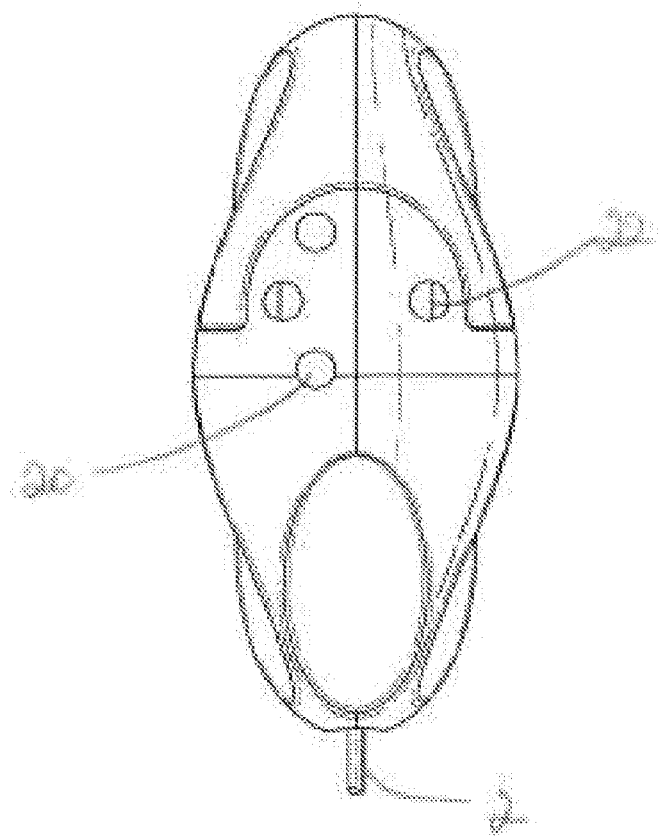

FIG. 29: Another view of the standalone device kit
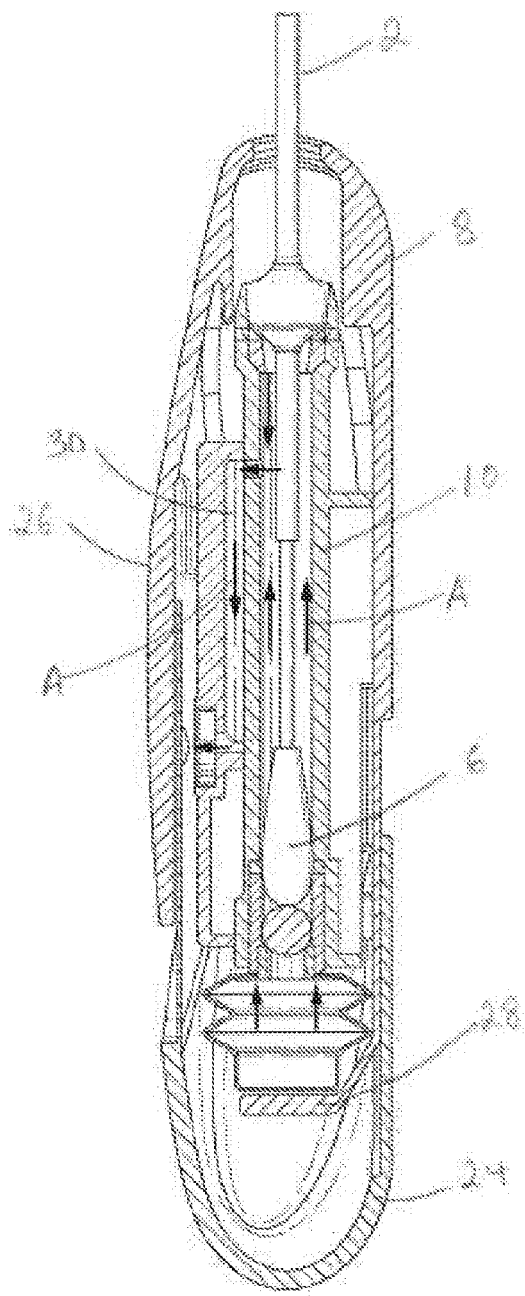

FIG. 30: A plan view of the standalone device kit with housing slid apart
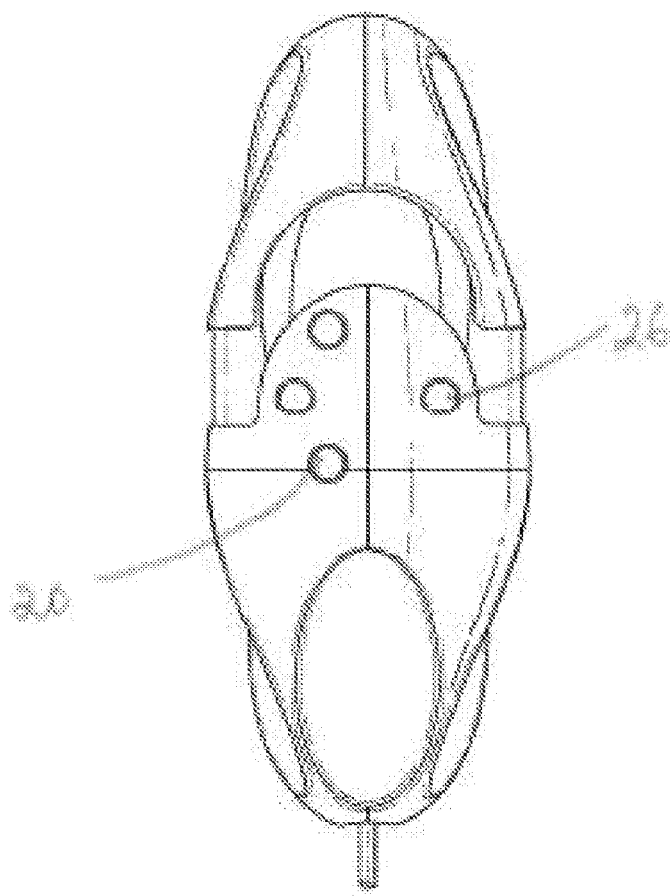

FIG. 31: Diluent chamber, tube and reaction chamber in standalone device kit
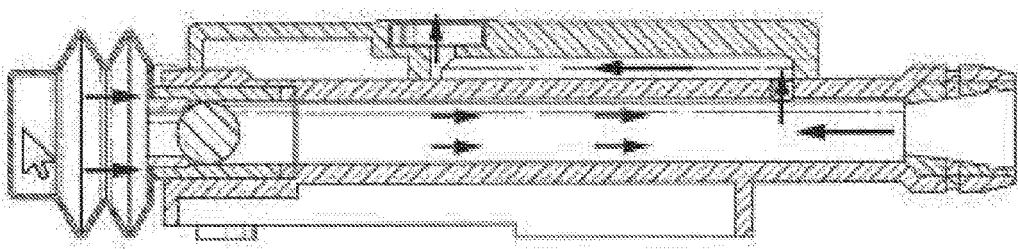

FIG. 32: Distribution of test solution to each reaction chamber in standalone device kit
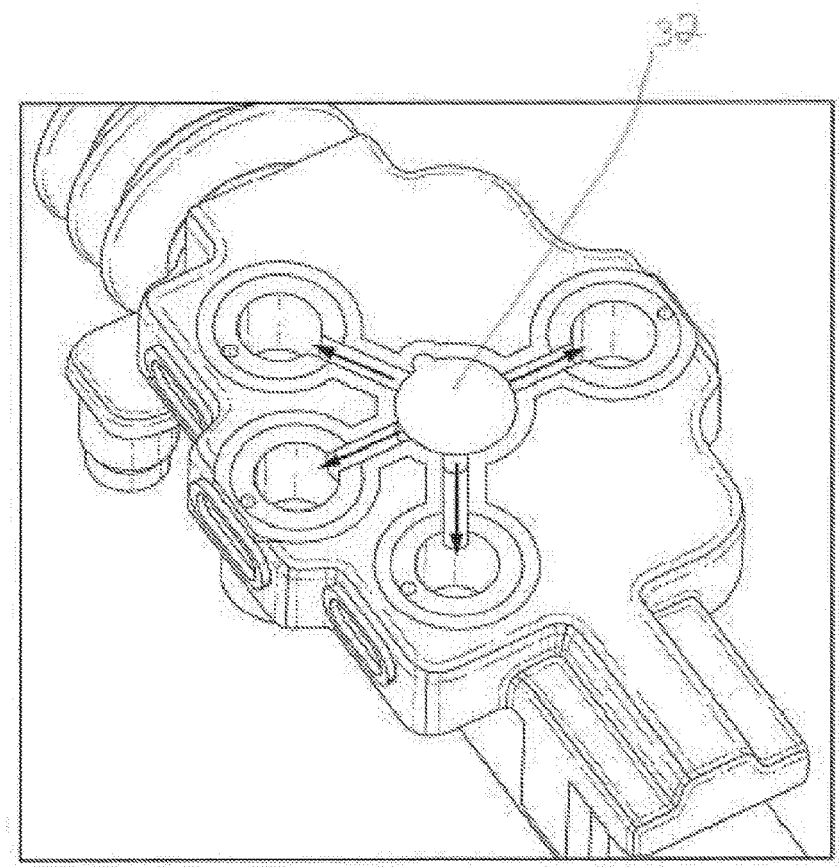

FIG. 33: Diagnostic swab device with housing
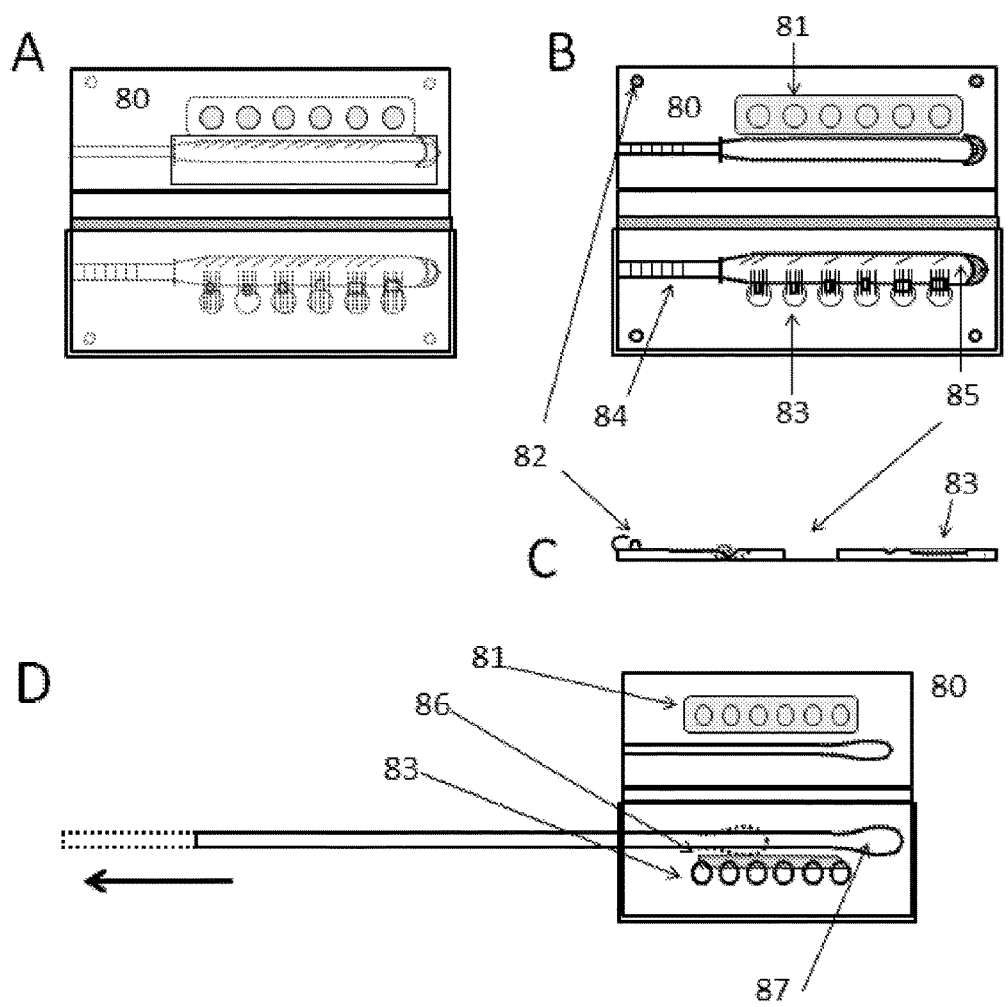

FIG. 34: Thread hook diagnostic device
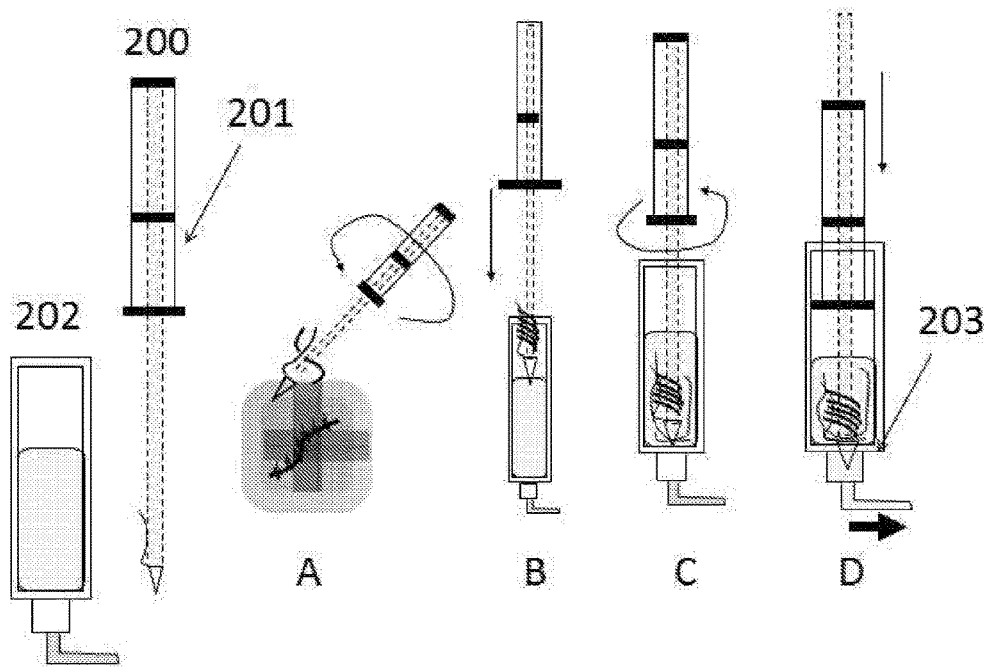

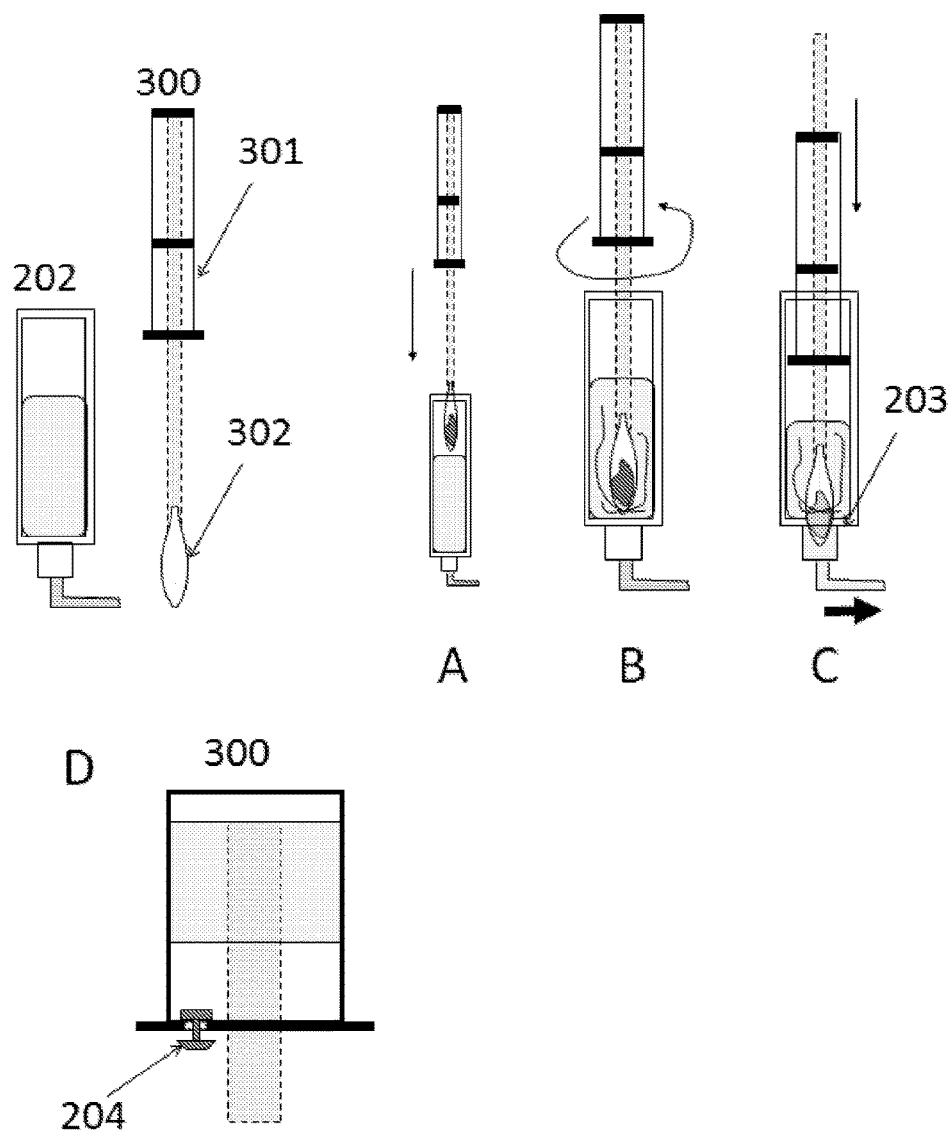
FIG. 35: Swab diagnostic device

FIG. 36: Diluent chamber for sample preparation
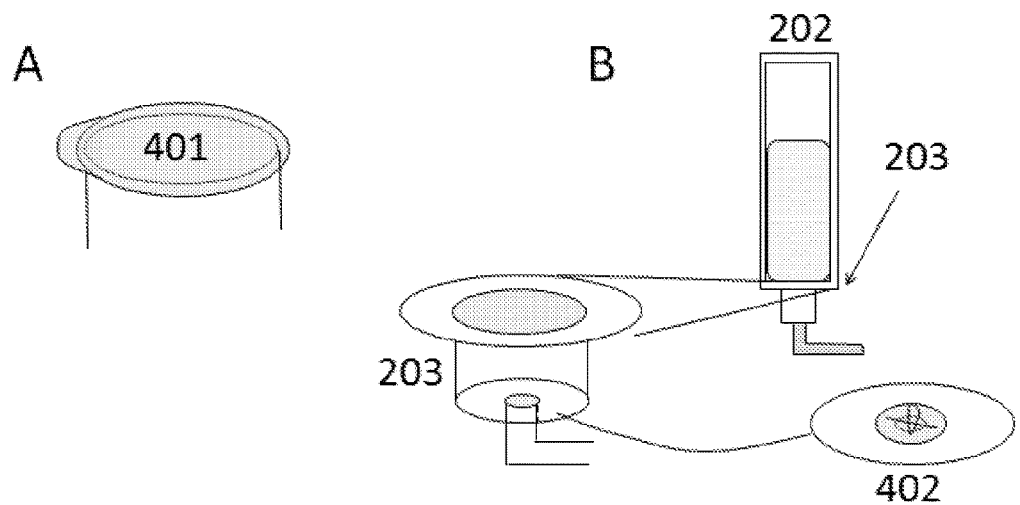

FIG. 37: A diagnostic device with sampling chamber and reaction wells
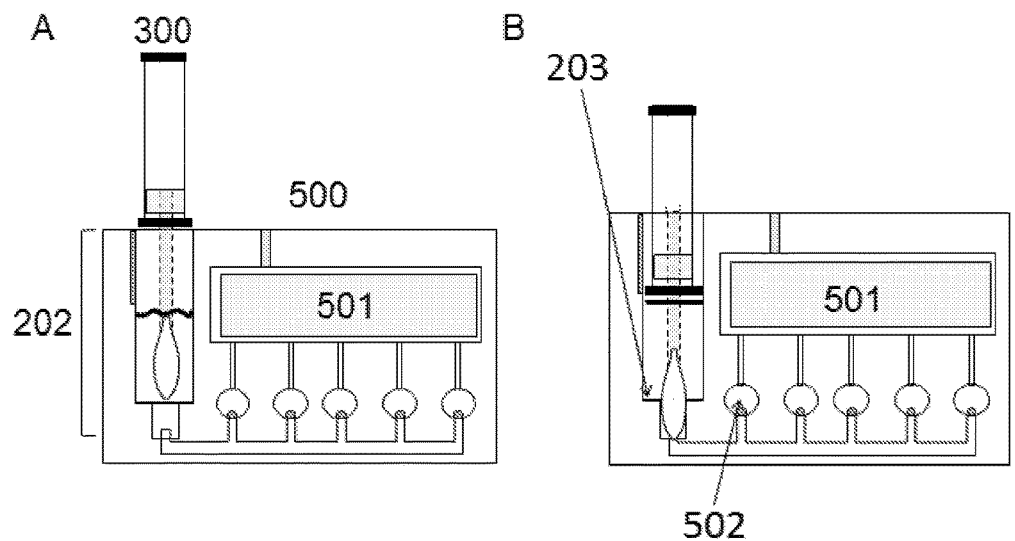

FIG. 38: A diagnostic device or Transfersystem
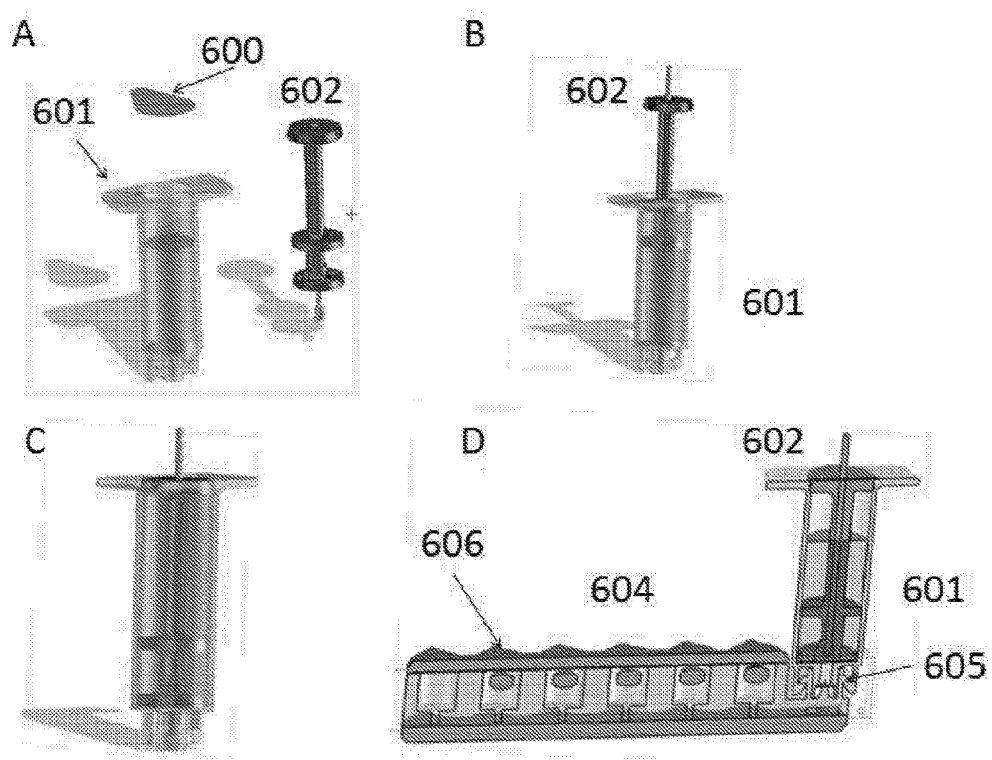

FIG. 39: Further embodiments of an analytic or diagnostic system
A.
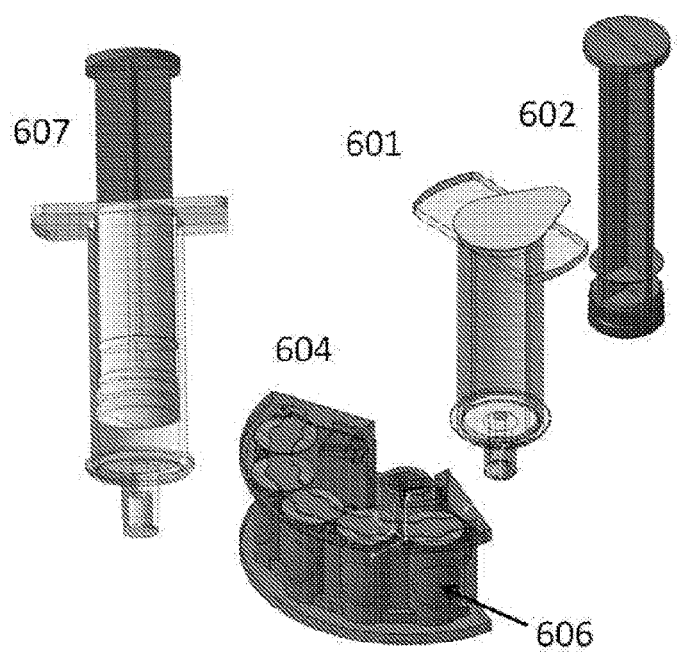
B.
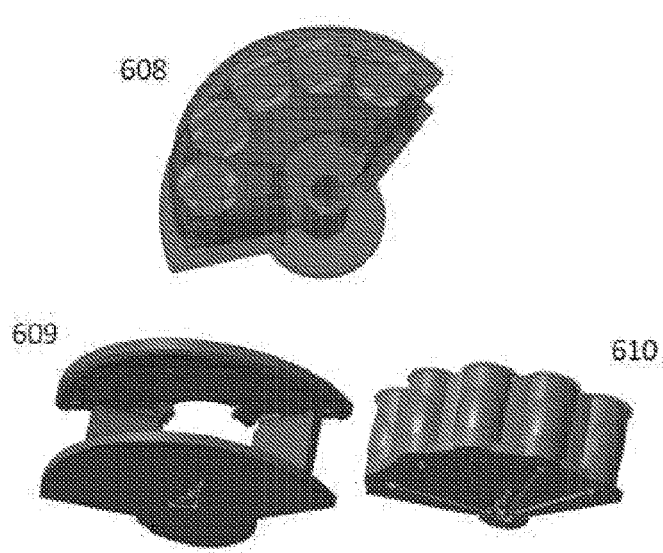

DETECTING MICROBIAL INFECTIONS IN WOUNDS

CROSS-REFERENCE TO RELATED APPLICATIONS

This application is a continuation application of, and claims the priority benefit of, U.S. application Ser. No. 16/090,045 entitled "DETECTING MICROBIAL INFECTIONS IN WOUNDS," which was filed on Sep. 28, 2018, and which is a national stage application of International Application No. PCT/US2017/024991 filed Mar. 30, 2017, which claims the benefit of U.S. Provisional Application No. 62/315,565 filed Mar. 30, 2016. The disclosures of those applications are incorporated by reference herein in their entireties.

TECHNICAL FIELD

Embodiments described herein generally relate to wound healing, and in particular to compositions, apparatuses and methods for the detection and treatment of wounds.

BACKGROUND

In mammals, dermal injury triggers an organized complex cascade of cellular and biochemical events that result in a healed wound. Wound healing is a complex dynamic process that results in the restoration of anatomic continuity and function: an ideally healed wound is one that has returned to normal anatomic structure, function, and appearance. A typical wound heals via a model consisting of four stages—'exudative' phase, proliferative phase, reparative phase and epithelial maturation (Hatz et al., *Wound Healing and Wound Management*, Springer-Verlag, Munich, 1994) orhemostatic, inflammatory, proliferative and remodeling phase (Nwomeh et al., *Clin. Plast. Surg.* 1998, 25, 341). The inflammatory phase is particularly important to the wound healing process, wherein biochemical reactions at the wound situs facilitate healing but also cause tissue breakdown due to production of excess proteases.

Infection of the wound results in either a slower, or an arrested healing process. For example, pathogens in a wound can produce toxins (e.g., *Clostridium* species), generate noxious metabolites like ammonia that raise pH (e.g., *Proteus* species), activate or produce tissue lytic enzymes like proteases, or promote tissue invasion, thereby leading to an increase in the size or seriousness of the wound. In a worst case, pathogens can leave the wound and cause sepsis.

In order to keep the chronicity of wounds in check, a variety of assessment techniques and/or tools are employed in the clinical and veterinary setting. Current methods of assessing an infected wound are based primarily on assaying for a variety of parameters associated with the wound. For instance, a wound may be assessed visually, length and depth measurements may be taken, digital photography may be used where available to track the visual condition and size of a wound (Krasner et al., supra). In clinical practice, diagnosis of infection is based on measurement of secondary parameters, such as, odor, presence of local pain, heat, swelling, discharge, and redness. Many of these clinical indicators, such as inflammation and discharge have a low predictive value of infection in wounds. In other instances, the number(s) and type(s) of pathogenic flora at the wound situs may be determined using laboratory and/or clinical diagnostic procedures. Swabbing of a wound followed by microbiology testing in the hospital laboratory is an option for confirmation of bacterial colonization and identification of the strains associated with infection, thus allowing for the prescription of correct antibiotic course. However, this process is time consuming and labor intensive. Delay in diagnosis of infection can delay the administration of antibiotics and may increase the risk of developing sepsis.

One of the biggest drawbacks associated with existing clinical diagnostics is a lag associated with the onset of infection and the timing of detection. For instance, positive identification of infection using swabbing procedures often depends on attainment of a "critical mass" of microorganisms at the wound site and so early detection cannot be made until a detectable level is reached. Also, the swabs may be contaminated with the flora of the surrounding tissue, thereby complicating the diagnostic procedure. Other drawbacks include, e.g., sampling errors, delays in transport of the swabs, errors in analytical procedures, and/or errors in reporting. See, the review by Bowler et al., *Clin Microbial Rev.* 14(2): 244-269, 2001.

There is therefore an imminent but unmet need for diagnostic reagents and methods that enable early diagnosis of clinical infection, preferably, which permit clinical diagnosis prior to manifestation of clinical symptoms of infection. There is also a need for compositions and methods that would assist in predicting clinical infection of a wound prior to the manifestation of clinical symptoms. Such a prognostic aid would allow early intervention with suitable treatment (e.g., antimicrobial treatment) before the wound is exacerbated and surgery or other drastic intervention is required to prevent further infection. Additionally, if clinicians could respond to wound infection as early as possible, the infection could also be treated with minimal antibiotic usage. This would reduce the need for hospitalization and would reduce the risk of secondary infections, e.g., as a result of contact with other diseased subjects.

SUMMARY

The technology disclosed herein provides for compositions and methods of detecting infected and/or chronic wounds. The disclosed technology improves upon exiting assays by: increasing the sensitivity, precision and specificity of detection of infected wounds; providing for the ability of qualitative and quantitative measurements; and, increasing the speed of detection of infected wounds in situ and in real-time. The assays and methods described herein are partly based on the use of specific reagents that detect biomarkers and/or probes which are present in infected or chronic wounds. The detection process may involve use of reagents that are specific to the markers present in infected wounds but not non-infected or non-chronic wounds and the detection step may involve qualitative or quantitative measurements of the signal(s) that are generated when the probe is acted upon by the marker. In embodiments wherein the detection method involves detection of enzymes present in wounds, the probes comprise modified enzyme substrates that are specific to the enzyme, which generate signals that may be optionally amplified. This greatly improves efficiency and specificity of detection. Moreover, a plurality of detection probes, each specific for one or more targets, e.g., enzymes that are specific to the wounds, may be employed. This greatly helps to maximize both efficiency and accuracy of diagnostic assays while minimizing the incidence of false positives (e.g., due non-specific interactions and/or target redundancy). Furthermore, the experimental results disclosed herein confirm that the novel probes and the assay techniques based thereon are capable of detecting and characterizing various types of wounds. Finally, the reagents of the disclosed technology may be used together with therapeutic molecules such as antibiotics, antifungal agents, etc. to monitor and evaluate treatment and management of chronic wounds.

Embodiments described herein are based, in part, on the discovery that cells of the immune system, including enzymes generated thereby, may serve as markers in the early diagnosis of wounds. These cells, e.g., neutrophils, are recruited at the wound situs to combat infection, do so by engulfing bacteria (and other pathogens) and/or neutralizing them with enzymes. Some enzymes are specific towards proteins (e.g., elastase, cathepsin G), others are specific towards cell wall components (e.g., lysozyme) and yet others mediate protein denaturation (e.g., NADPH oxidase, xanthine oxidase, myeloperoxidase (MPO) and other peroxidases). These cells, e.g., neutrophils, are generally only short-lived and when they lyse in the area of the infection, they release the contents of their lysosomes including the enzymes, which can then be detected to provide a reliable measurement of the status of the wound.

Accordingly, various embodiments described herein utilize the detection of enzyme markers, which are indicative of the presence of myeloid cells, and neutrophils in particular, in a biological sample of interest, for example, wound tissue. Increased level or activity of such enzymes in the wound fluid, therefore, corresponds to a heightened bacterial challenge and a manifestation of disturbed host/bacteria equilibrium in favor of the invasive bacteria.

Provided herein are embodiments of a wound dressing, devices, and methods for detecting an infection in a wound or a sample. One embodiment is a wound dressing comprising a wound contacting layer, a reagent layer comprising one or more testing regions, wherein the reagent layer is in fluid communication with the wound contacting layer, and an outer layer that overlays the reagent layer. In some embodiments, the wound contacting layer comprises gel-forming polymers. In further embodiments, each of the one or more testing regions comprises one or more of each of: back-flow trap, reagent pad, filter pad, indicator trap, and absorbent area, wherein one or more viewing windows are located either above the reagent pad or the indicator trap. In further embodiments, the reagent pad is in fluid communication with the filter pad; the filter pad is in fluid communication with the indicator trap; and the indicator trap is in fluid communication with the absorbent area.

In other embodiments, one or more testing regions comprises one or more reagents selected from the group consisting of enzyme-reactive indicators, reagents that are sources of peroxide, enzymes that produce colored products, pH indicators, protein responsive reagents, and moisture-detecting reagents. The enzyme-reactive indicators include protein-indicator conjugates printed, sprayed, or otherwise deposited in or on the reagent pad. In some embodiments, the protein-indicator conjugate has the structure of Formula (I): A-B, wherein A is an anchor region or moiety that helps to bind an enzyme-reactive region to the reagent pad, and B is the enzyme-reactive region.

In some embodiments, the enzyme-reactive region comprises a peptide and/or an indicator region. In further embodiments, the wound dressing comprises an indicator region that after having been cleaved by the target enzyme in a sample is further transformed into a colored species by accessory enzymes selected from a lipase, esterase, hexosaminidase, peroxidase, oxidase, galactosidase, glycosidase, glucosidase, and laccase, or a combination of two or more thereof. In some embodiments, the enzyme-reactive indicators interact with elastase, lysozyme, cathepsin G, myeloperoxidase, or any combination thereof. In further embodiments, the enzyme-reactive indicators comprise a moiety capable of producing a visible color or a detectable electronic change upon interaction of the enzyme-labile or enzyme-reactive region with one or more enzymes, wherein the moiety is selected from the group consisting of a peroxidase substrate, arylamine, an amino phenol, a neutral dye, a charged dye, a nanoparticle, a colloidal gold particle, or an analog thereof. The anchor region can be attached to the reagent pad covalently, non-covalently, or ionically. In some embodiments, pH-sensitive reagents produce a visible color comprise bromothymol blue, phenol red, bromophenol red, chlorophenol red, thymol blue, bromocresol green, bromocresol purple; nitrazine yellow; or other sulfophthalein dyes.

In some embodiments, the wound dressing also comprises one or more lines of wicking stitching or wicking tufting throughout all layers of the wound dressing except the outer layer, wherein the wicking stitching or wicking tufting provides fluid communication between the reagent layer and the wound contacting layer. Fibers that are wettable and exhibit capillary action may be used for wicking stitching or wicking tufting to form fluid communication between a sample or a wound and the reagents. In some embodiments, the wicking fibers are solid or hollow. Examples of wicking fibers include, but are not limited to, cotton, rayon, viscose, wool, silk, polyester, polyamide, CMC, and polypropylene.

In further embodiments, the wound dressing comprises one or more testing regions, comprising a leach-back trap in fluid communication with the reagent pad and one or more lines of wicking stitching or wicking tufting crossing through one or more testing regions only at the leach-back trap. In some embodiments, a foam layer is added between the wound contacting layer and the reagent layer. One or more perforations can be added in the wound contacting layer or in the foam layer and the wound contacting layer. In further embodiments, each of the one or more testing regions further comprises a leach-back trap in fluid communication with the reagent pad and one or more perforations aligned with the leach-back trap.

In some embodiments, the testing regions comprise a multichannel testing region, wherein each channel within the multichannel testing region is separated from an adjacent channel by one or more impermeable separators or borders. Such multichannel testing regions can comprise 1 to 10 testing regions, preferably 3, 4, or 5 testing regions, wherein the testing regions are arranged in a linear or a radial configuration. Arrays of multichannel testing regions can be combined to cover a broader area of a wound or wound dressing. In further embodiments, the outer layer of the wound dressing comprises one or more windows that permit visualization of a signal from the reagent layer, wherein the signal is a color change.

Such wound dressing or device provides a method of detecting the level of one or more enzymes in a mammalian wound, comprising contacting the mammalian wound with the wound dressing; observing one or more signals in the reagent layer, wherein the signal is a color change; and comparing the signal to a reference or control to determine the level of an enzyme. In another embodiment, the wound dressing can be used to detect the presence of one or more enzymes and/or pH in a mammalian wound, comprising contacting the mammalian wound with the wound dressing and observing one or more signals in the reagent layer, wherein the signal is a color change. In another embodiment, the wound dressing can be used to treat an infection in a wound of a mammal or to determine when such treatment is necessary, comprising contacting the wound with a wound dressing described herein, observing one or more signals in the reagent layer, wherein the signal is a color change and indicates the presence of an infection, and administering a medical treatment to the mammal.

In some embodiments, a device for detecting an infection in a wound comprises a wound contacting layer, a reaction layer comprising one or more reagents that can indicate the presence of one or more analytes associated with an infection, wherein the reagents are affixed to a solid phase and produce a detectable signal in a reporter area, a cover on top of the reaction layer, wherein the cover comprises one or more windows or clear areas to allow visualization of the detectable signal, such as a color change, and fluid communication between the wound contacting layer and the reaction layer. Reagents include enzymereactive indicators that interact with one or more enzymes selected from the group consisting of lysozyme, MPO, cathepsin G, elastase, catalase, lipase, esterase, and any combination thereof, at least one indicator for pH or a change in pH, wherein the indicators may be printed, sprayed, or deposited on a solid phase or support material, including paper, viscose, regenerated cellulose, glass fiber, or similar materials. In further embodiments, the enzymereactive indicators comprise a moiety capable of producing a visible color or a detectable electronic change upon interaction of the enzyme-labile or enzyme-reactive region with one or more enzymes, wherein the moiety is selected from the group consisting of a peroxidase substrate, arylamine, an amino phenol, a neutral dye, a charged dye, a nanoparticle, a colloidal gold particle, and an analog thereof. In further embodiments, the device comprises wicking stitching or wicking tufting of an absorbent material to form fluid communication between the wound contacting layer and the reaction layer.

A device for detection of infection associated enzymes that is provided as an independent entity and can be placed into any dressing or bandage system, comprising a sample inlet in fluid communication with reagent cells, wherein reagent cells comprise indicators for sample delivery and/or pH change, which can be one and the same, and one or more indicators for biomarkers of an infection, including lysozyme, MPO, cathepsin G, elastase, catalase, lipase, esterase, and any combination thereof. The fluid communication comprises at least one indicator channel, lane, or arm, such as one to ten indicator channels, or one, two, three, four, five, six, seven, eight, nine, or ten separate indicator channels, wherein the indicators are printed, sprayed, or deposited in a reaction area or field on a carrier material or solid phase and arranged in a radial configuration to form a disk, and wherein the reaction areas or fields are separated by impermeable separators or lanes. The carrier material may comprise a non-woven material. In some embodiments, the disk comprises reagents printed, sprayed, or deposited on the top surface of the disk with a trap material and a substrate material on the bottom surface, wherein the substrate can be digested by one or more enzymes in the sample to release one or more products that migrate towards the trap. In further embodiments, one or more products are colored or produce a color change capable of being visualized on the top surface of the disk.

In additional embodiments, a diagnostic disk for detecting an infection in a wound comprises a reaction layer comprising one or more reagents that interact with an enzyme indicative of an infection, wherein the reagents are affixed to a solid phase; each reagent is sprayed, printed, or deposited in a reagent area separated by impermeable separators; each lane comprises a reporter area wherein a color change can be observed; and a cover comprising a window for visualizing the color change in the reported area. The diagnostic disk may further comprise at least one reagent that produces a color change in response to a change in pH. Multiple lanes in the diagnostic disk, wherein each lane contains a different indicator/reagent, can be arranged in a linear or radial configuration about a cut access, perforation, or wicking material that allows fluid communication between a sample or wound contact material and the reagents in the reaction layer. The reagents include indicators as described above, namely, reagents that interact with lysozyme, MPO, cathepsin G, elastase, catalase, lipase, or esterase. In some embodiments, the diagnostic disk comprises a solid phase material selected from the group consisting of paper, viscose, regenerated cellulose, glass fiber, and similar material. In further embodiments, the disk is attached to a non-woven carrier in a wound dressing, wherein means for such attachment include, but are not limited to, a continuous adhesive, ring or annular adhesive, welding with UV printed border, and welding with a polyethylene component or the non-woven carrier.

In further embodiments, the reagents describes herein may be applied to form a lateral flow or dipstick device for detecting an infection in a wound, comprising one or more reagent disks arranged in a linear configuration, wherein each reagent disk is impregnated with a reagent that interacts with an enzyme to produce a color change or a similar detectable signal, wherein one of the disks produces a color change based on pH, and wherein the disks are affixed to a solid phase comprising paper, viscose, regenerated cellulose, glass fiber, or similar materials. Reagents include enzyme-reactive indicators that produce a color signal in the presence of lysozyme, MPO, cathepsin G, elastase, catalase, lipase, or esterase. In one embodiment, each disk is separated by an impermeable border or lane.

In a further embodiment, a standalone device for detecting an infection in a wound or a sample comprises a housing, comprising: a sampling component for collecting the sample; a sample preparation chamber in fluid communication with a reaction chamber, wherein the sample preparation chamber receives the sample; the reaction chamber comprising one or more reaction cells containing reagents that interact with one or more enzymes in the sample to indicate the presence of an infection and/or pH of the sample; and a window or a clear area for visualizing a detectable signal, wherein the signal is a color change or an electronic output. One or more reagents interact with an enzyme selected from the group consisting of lysozyme, MPO, cathepsin G, elastase, catalase, lipase, and esterase to produce a detectable signal, wherein the signal is a color change. One or more regents produce a color change in response to a change in pH, a basic pH, or an acidic pH. In further embodiments, the reagents perform the reactions in a primarily liquid medium, wherein the reagents may be provided in tablet form for use in the reaction cells. In some embodiments, the reagents may be printed, sprayed, or deposited in separate reagent fields on a support material to form a panel of tests, such as a testing strip, for use in the reaction chamber. Support materials include paper, viscose, regenerated cellulose, and glass fiber. Reagent fields can be arrayed in a line along a plastic or paper carrier strip, which is capable of absorbing the sample in the reaction chamber, allowing the sample to interact with the reagents in the reaction chamber. In some embodiments, the sampling component comprises a swab device, or a hook or needle device adapted to removing a sampling thread from a wound dressing to sample the wound fluid without disturbing the dressing.

In further embodiments, a kit for detecting an infection in a sample comprises a sampling component for collecting the sample; a test device comprising a housing surrounding a tube to define an opening in the housing for receiving the sampling component, the housing comprising: a diluent chamber that holds a liquid diluent; a reaction well in liquid communication with the tube or the sample, the reaction well holding one or more reagents that interacts with one or more analytes to produce a color change or similar detectable signal; a viewing window or reporter area wherein the color change or similar detectable signal can be observed; and wherein the liquid diluent flows from the sample component into the reaction well to mix the sample with the reagents in the reaction well. The reagents comprise one or more enzyme-reactive indicators and/or pH indicator, as described above. The sample may be obtained from a wound, a wound dressing, or a surgical site. In some embodiments, the sampling component is a swab device or a hook or needle device. The reagents can be provided in tablet form, which are dissolved upon contacting the liquid diluent and the sample. The reagents can also be deposited in separate fields on a testing strip to form a panel of tests, which can be applied in the reaction wells.

In another embodiment, the reagents are provided in liquid form for use in the reaction wells. The number of reaction wells is based upon the number of analytes to be analyzed, ranging from one to ten, including indicators that produce a detectable signal in response to pH or the presence of one of the following enzymes: lysozyme, MPO, cathepsin G, elastase, catalase, lipase, and esterase. The reaction wells can be arranged in various configurations, including a linear or a radial configuration.

In another embodiment, a wound dressing is disclosed comprising: a wound contacting layer; a reagent layer comprising one or more testing regions, wherein the reagent layer is in fluid communication with the wound contacting layer; and an outer layer that overlays the reagent layer.

In another embodiment, a wound dressing is disclosed wherein each of the one or more testing regions comprises one or more of each of a back-flow trap, a reagent pad, a filter pad, an indicator trap, and an absorbent area, and wherein one or more viewing windows are located either above the reagent pad or the indicator trap.

In another embodiment, a method of detecting the level of one or more enzymes in a mammalian wound is disclosed, the method comprising: contacting the mammalian wound with a wound dressing; observing one or more signals in the reagent layer, wherein the signal is a color change, a fluorescent signal, a luminescent signal, or an electrical change; and comparing the signal to a reference or a control to determine the level of an enzyme.

In another embodiment, a method of detecting the presence of one or more enzymes in a mammalian wound is disclosed, the method comprising: contacting the mammalian wound with a wound dressing; and observing one or more signals in the reagent layer, wherein the signal is a color change, a fluorescent signal, a luminescent signal, or an electrical change.

In another embodiment, a method of detecting an infection in a mammalian wound is disclosed, the method comprising: contacting the wound with a wound dressing; and, observing one or more signals in the reagent layer, wherein the signal is a color change, a fluorescent signal, a luminescent signal, or an electrical change.

In another embodiment, a device for detecting an infection in a wound is disclosed, comprising: a wound contacting layer; a reaction layer comprising one or more reagents that can indicate the presence of one or more analytes associated with an infection, wherein the reagents are affixed to a solid phase and produce a detectable signal in a reporter area; a cover on top of the reaction layer, wherein the cover comprises one or more windows or clear areas to allow visualization of the detectable signal; and, fluid communication between the wound contacting layer and the reaction layer.

In another embodiment, a wound dressing is disclosed wherein the reagent pad is in fluid communication with the filter pad; the filter pad is in fluid communication with the indicator trap; and the indicator trap is in fluid communication with the absorbent area.

In another embodiment, a diagnostic disk for detecting an infection in a wound is disclosed, comprising: a reaction layer comprising one or more reagents that interact with a target enzyme indicative of an infection, wherein the reagents are affixed to a solid phase; each reagent is sprayed, printed, or deposited in a reagent area in a lane separated from adjacent lanes by impermeable separators; each lane comprises a reporter area wherein a color, color change, or other detectable signal is observed; and a cover comprising a window for visualizing the signal in the reporter area.

In another embodiment, a lateral flow or dipstick device for detecting an infection in a wound is disclosed, comprising: one or more reagent disks arranged in a linear configuration, wherein each reagent disk is impregnated with a reagent that interacts with an enzyme to produce a color change and/or is pH-sensitive, comprising bromothymol blue, phenol red, bromophenol red, chlorophenol red, thymol blue, bromocresol green, bromocresol purple; nitrazine yellow; or other sulfophthalein dyes, and wherein the disks are affixed to a solid phase.

In another embodiment, a device for detecting an infection in a wound or a sample is disclosed, comprising a housing, wherein the housing comprises: a sampling component for collecting the sample; a sample preparation chamber in fluid communication with a reaction chamber, wherein the sample preparation chamber receives the sample; the reaction chamber comprising one or more reaction cells containing reagents that interact with one or more enzymes in the sample to indicate the presence of an infection and/or pH of the sample; and a window or a clear area for visualizing a detectable signal, wherein the signal is a color change.

In another embodiment, a kit for detecting an infection in a sample is disclosed, comprising: a sampling component for collecting the sample; a test device comprising a housing surrounding a tube to define an opening in the housing for receiving the sampling component, the housing comprising: a diluent chamber that holds a liquid diluent; a reaction well in liquid communication with the tube, wherein the reaction well holds one or more reagents that interact with one or more analytes to produce a color change or a detectable signal; a viewing window or reporter area wherein the color change or detectable signal can be observed; and wherein the liquid diluent flows from the sample component into the reaction well to mix the sample with the reagents in the reaction well.

It is understood that other embodiments and configurations of the subject technology will become readily apparent to those skilled in the art from the following detailed description, wherein various configurations of the subject technology are shown and described by way of example or illustration. As will be realized, the subject technology is capable of other and different configurations and its several details are capable of modification in various other respects, all without departing from the scope of the subject technology. Accordingly, the figures and detailed description are to be regarded as illustrative in nature and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

To understand the present disclosure, it will now be described by way of example, with reference to the accompanying figures in which embodiments and examples of the disclosures are illustrated and, together with the descriptions below, serve to explain the principles of the disclosure.

FIG. 1: Examples of engineered three-dimensional fabric structures, such as corrugations.

FIG. 2: Example of a dressing with AQUACEL showing different layers of a dressing and stitching that draws fluid from a wound to the reaction layer of the dressing.

FIG. 3: Schematic of reaction cells showing different components of a reaction cell with stitching (21) in (A) and cut access (27) in (B). In some embodiments, each reaction cell can be a different reporter or dye system.

FIG. 4: Movement of indicators in reaction cells upon exposure to fluid, which flows from cut access and reagents (22) toward absorbent or evaporation area (25). Over time, the reaction products diffuse and migrate toward an absorbent or evaporation area. Movement of indicators arranged in a radial manner is shown in (B). In some embodiments, each lane or reaction cell can be a different reporter or color system. Multiple reaction cells can be used as shown in (C). Multiple reaction cells can be used in arrays or combinations to provide indicator function over an area. Leach back traps may be used to prevent backflow.

FIG. 5: Indicators can be arranged in a circular or radial manner to form indicator disks (A). In some embodiments, each lane or reaction cell (45-48) can be a different reporter or color system, such as bromothymol blue, phenol red, bromophenol red, chlorophenol red, thymol blue, bromocresol green, bromocresol purple; nitrazine yellow; or other sulfophthalein dyes. (B) shows views of a radial indicator disk from above and from below.

FIG. 6: Dressing printed for MPO detection. In one embodiment, a wound contact material is sprayed or printed with amylase, starch, and glucose oxidase, followed by printing of a substrate for MPO printed in the centers of each sprayed area.

FIG. 7: In-place color development of MPO and elastase substrates on testing strips are shown. These test strips represent prototypes of visualization methods for detecting the presence of MPO and elastase in a sample, wherein color (e.g., blue) increases in intensity with greater substrate concentration.

FIG. 8: Examples of substrates, including MPO substrate (Fast Blue derivative), elastase substrate, and oxidation of indoxyl to blue colored indigo are shown.

FIG. 9: In-place color development of different indicators in radial arrangement. (A) and (B) represent prototypes of indicators for detecting certain analytes, including pH change, MPO, lysozyme, and elastase. In one embodiment, pH change can be reported as a color change from yellow to green; MPO reported as an appearance of a blue color; lysozyme reported as an appearance of pink or red color; elastase reported as an appearance of green or blue color; and liquid control reported as an appearance of a blue or purple color.

FIG. 10: Schematics of a radial indicator insert or disk.

FIG. 11: Schematics of a radial indicator insert or disk with a window for detection.

FIG. 12: Schematics of another embodiment of a radial indicator insert or disk with a window for detection.

FIG. 13: Transport of Remazol Brilliant Blue, showing migration of indicators to reporter area after liquid transport.

FIG. 14: Example of a pH indicator. In one embodiment, the color can change from green to blue with increase in pH.

FIG. 15: Schematic of a lysozyme test strip. Fluid flow causing stained peptidoglycan particles to move upwards to trap layer.

FIG. 16: Examples of indicator substrates and reactions.

FIG. 17: Example of indicator disk freely placed in a dressing.

FIG. 18: Embodiments of diagnostic disks in nonwoven layer in dressing.

FIG. 19: Embodiments of diagnostic disks in nonwoven layer in dressing.

FIG. 20: Example of manufacturing diagnostic disks in sheets.

FIG. 21: Embodiments of printed and applied paper disks. In some embodiments, each disk can be a different reporter or color system.

FIG. 22: Methods of attaching or applying diagnostic disks to non-woven layer in dressing.

FIG. 23: Dipstick devices with indicator inserts or disks arranged in different arrays and combinations are shown. In some embodiments, each insert, disk, or lane can be a different reporter or color system.

FIG. 24: Sampling thread and use in dressing. Sampling thread can be incorporated in a wound dressing or at a surgical site, wherein the thread can be pulled out without disturbing the dressing to test for the presence of microbial infection or condition of the surgical site or wound in a diagnostic device.

FIG. 25: Assembly for manufacturing indicator inserts.

FIG. 26: Cross section of a standalone device kit

FIG. 27: Sampling tip inserted in the housing of standalone device kit

FIG. 28: A plan view of the standalone device kit

FIG. 29: Another view of the standalone device kit

FIG. 30: A plan view of the standalone device kit with housing slid apart

FIG. 31: Diluent chamber, tube and reaction chamber in standalone device kit

FIG. 32: Distribution of test solution to each reaction chamber in standalone device kit FIG. 33: Diagnostic swab device with housing, wherein reaction with indicator disks or inserts can be observed from a viewing window in the housing.

FIG. 34: Thread hook diagnostic device, suitable for pulling out a sampling thread from a dressing for analysis.

FIG. 35: Swab diagnostic device, wherein a swab is used to obtain a sample for testing with a diagnostic device, further comprising a diluent chamber, gas outlet, and a plunger.

FIG. 36: Diluent chamber for sample preparation. A diluent chamber comprising a diluent is adapted for use with a swab device, a thread hook device, and similar sample preparation devices, comprising a resealable top and a seal or film at the bottom, wherein breaking the seal or film (402) allows the sample to mix with the diluent solution, which flows out of the diluent chamber and into a testing device comprising reaction chambers or wells.

FIG. 37: Embodiment of diagnostic device with sampling chamber and reaction wells. One embodiment of a diagnostic device with reaction chambers (502) adapted to being connected to sampling chamber or diluent chamber (202) for receiving a sample from a sample preparation device (300), such as the swab device.

FIG. 38: Embodiment of diagnostic device or transfer system, wherein the sample chamber or diluent chamber uses a Luer-lock connector to attach to reaction chambers for testing a sample fluid. In one embodiment, the plunger or piston comprises a gas outlet, hook for holding a sample, and membrane that lets out gas as the plunger is depressed into the diluent chamber.

FIG. 39: Further embodiments of an analytic or diagnostic system, wherein reaction chambers are arranged in a radial arrangement.

DETAILED DESCRIPTION

Various aspects of the disclosed technology will be described more fully hereinafter. Such aspects may, however, be embodied in many different forms and should not be construed as limited to the embodiments set forth herein; rather, these embodiments are provided so that this disclosure will be thorough and complete, and will fully convey it scope to those skilled in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

Provided herein are means to detect infections in wounds. In some embodiments these are wound dressings able to detect infection in one or more body fluids before such infection is otherwise apparent. In some embodiments, the wound dressing reacts with wound exudate or wound fluid to detect infection in a wound through a visible or otherwise detectable change in the dressing. In some embodiments, wound exudate or wound fluid is drawn up through the wound dressing to a reagent layer for assessment of possible infection without the need to remove the dressing. In some embodiments, wound exudate or wound fluid reacts with the reagent layer to give rise to a color or other visible or observable marker. In some embodiments, the color is easily distinguishable from those colors that are common in wounds or body fluids. In some embodiments, the reaction between the wound exudate or wound fluid and the reagent layer of the wound dressing occurs at ambient temperature and within a period of time short enough to allow timely response, such as a decision to make a dressing change after cleaning the wound and examining the test result and/or to administer antiseptics or local or systemic antibiotics. In some embodiments, the color or other visible or observable marker and/or the location of the color or other visible or observable marker indicates one or more areas of the wound that deserve closer attention and/or antisepsis. In some embodiments, the color change function is embedded in parts of the dressing that are only visible on dressing change.

In further embodiments, the reagent layer that gives rise to a color change or other visible or observable marker is a standalone device, disk, or insert, capable of application with any wound dressing, at a surgical or wound site, or by itself as a dipstick-type of device. In further embodiments, indicator reagents are applied in a "swab sample preparation device" or a stand-alone device into which wound fluids are injected. In some embodiments, indicator reagents are printed directly on support materials, such as the various layers within a wound dressing.

In some embodiments disclosed herein, a wound dressing comprises a wound contacting layer; a reagent layer comprising one or more testing regions or indicator reagents; and an outer layer that overlays the reagent layer. The wound dressing may comprise one or more testing regions, which further comprise one or more of a back-flow trap, reagent pad, a filter pad, an indicator trap, and an absorbent area, wherein the viewing window is located either above the reagent pad or the indicator trap and the reagent pad is in fluid communication with a filter pad; the filter pad is in fluid communication with the indicator trap; and the indicator trap is in fluid communication with the absorbent area.

In some embodiments, testing regions comprise one or more components selected from the group consisting of enzyme-reactive indicators, reagents that are sources of peroxide, enzymes that are able to transform color reactions, pH indicators, protein responsive reagents, and moisture-detecting reagents. Enzyme-reactive indicators may comprise protein-indicator conjugates.

In some embodiments, protein-indicator conjugates are deposited in or on the reagent pad. In some embodiments, protein-indicator conjugate has the structure of Formula (I): A-B, wherein: A is an anchor region for attachment to the testing region; and B is an enzyme-reactive region. In further embodiments, the enzyme-reactive region comprises a peptide or an indicator region. The anchor region may be covalently or non-covalently attached to the reagent pad.

In further embodiments, the wound dressing comprises one or more lines of wicking stitching or wicking tufting throughout all layers of the wound dressing except the outer layer. One or more testing regions further comprises a leach-back trap in fluid communication with the reagent pad, the one or more lines of wicking stitching or wicking tufting crossing through each of the one or more testing regions only at the leach-back trap. In further embodiments, the wound dressing comprises a foam layer between the wound contacting layer and the reagent layer. In some embodiments, the wound dressing further comprises one or more perforations of the wound contacting layer.

In some embodiments, enzyme-labile or enzyme-reactive regions contained therein may interact with target enzymes including elastase, lysozyme, cathepsin G, and myeloperoxidase. In further embodiments, the enzyme-labile or enzyme-reactive region comprises a moiety capable of producing a visible color or detectable electronic change upon interaction of the enzyme-labile or enzyme-reactive region with one or more target enzymes, the moiety being selected from a peroxidase substrate, arylamine, an amino phenol, an indoxyl, a neutral dye, a charged dye, a nanoparticle, and a colloidal gold particle, and an analog thereof. In some embodiments, after the target enzyme has cleaved the indicator from the substrate it is further reacted by an accessory enzyme selected from a lipase, esterase, hexosaminidase, peroxidase, oxidase, glycosidase, glucuronidase, glucosidase, and laccase, or a combination of one or more thereof.

Applications of the reactive regions may include a device for detection of infection associated enzymes, on a solid phase such as paper, viscose, regenerated cellulose, glass fiber, mixtures of same or similar material, or arrayed in a line along a plastic or paper carrier strip.

In some embodiments, reagent or indicator inserts or disks for detection of infection associated with certain enzymes may be provided as an independent entity and placed into any dressing system comprising a sample inlet, diffusion channels toward different areas containing reagents, an indicator for sample delivery and or an indicator of pH which may be one in the same, and one or more indicators for the following markers selected from lysozyme, MPO, cathepsin G, elastase, catalase, lipase, esterase.

In some embodiments, the enzyme labile region is labile to a protease and the polymer binding domains are selected from cellulose binding domains or are hydrophobic binding domains.

In some embodiments, the enzyme labile region is labile to cathepsin or elastase.

In some embodiments, the chemical entity is selected from a small molecule entity, a modified oligomer, and a modified polymer.

In another aspect, provided herein is a chemical entity for the detection of infection in a wound, the chemical entity comprising an indicator region comprising a pH-sensitive moiety that presents a visible color change.

In some embodiments, the chemical entity further comprises an anchor region wherein the anchor region enables binding of the chemical entity to a support material.

In some embodiments, the pH-sensitive moiety that presents a visible color change at alkaline pH. In some embodiments, the pH-sensitive moiety that presents a visible color change at neutral pH. In some embodiments, the pH-sensitive moiety that presents a visible color change at acidic pH.

In some instances, the pH of a wound can influence many factors of wound healing, such as angiogenesis, protease activity, oxygen release, and bacterial toxicity. Chronic non-healing wounds may have an elevated alkaline environment. As the wound progresses towards healing, the pH of the wound moves to neutral and then becomes acidic. Monitoring of the pH of the wound may provide a method to assess the condition of the wound (e.g., infection or no infection) and aid in determining a wound's response to treatment.

Accordingly, in some aspect of the disclosed technology, the chemical entity for the detection of infection in a wound comprises an indicator region comprising a pH-sensitive moiety that presents a visible color change. In some embodiments, the chemical entity further comprises an anchor region wherein the anchor region enables binding of the chemical entity to a support material. In some embodiments, the pH-sensitive moiety presents a visible color change at alkaline pH. In some embodiments, the pH-sensitive moiety presents a visible color change at pH=7.2-9.5. In some embodiments, the pH-sensitive moiety presents a visible color change at pH=7.2-9.0. In some embodiments, the pH-sensitive moiety presents a visible color change at pH=7.2-8.5. In some embodiments, the pH-sensitive moiety presents a visible color change at pH=7.2-8.0. In some embodiments, the pH-sensitive moiety presents a visible color change at pH=7.5-8.5. In some embodiments, the pH-sensitive moiety presents a visible color change at pH=7.5-9.0. In some embodiments, the pH-sensitive moiety presents a visible color change at pH=8.0-9.0. In some embodiments, the pH-sensitive moiety presents a visible color change at pH=7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5, or increments thereof.

In some embodiments, the pH-sensitive moiety presents a visible color change at neutral pH. In some embodiments, the pH-sensitive moiety presents a visible color change at pH=6.9, 7.0, or 7.1, or increments thereof.

In some embodiments, the pH-sensitive moiety presents a visible color change at acidic pH. In some embodiments, the pH-sensitive moiety presents a visible color change at pH=4.5-6.8. In some embodiments, the pH-sensitive moiety presents a visible color change at pH=4.5-6.5. In some embodiments, the pH-sensitive moiety presents a visible color change at pH=5.0-6.8. In some embodiments, the pH-sensitive moiety presents a visible color change at pH=5.4-6.8. In some embodiments, the pH-sensitive moiety presents a visible color change at pH=5.4-6.5. In some embodiments, the pH-sensitive moiety presents a visible color change at pH=4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or increments thereof.

In some embodiments, the pH-sensitive moiety is bromothymol blue, phenol red, bromophenol red, chlorophenol red, thymol blue, bromocresol green, bromocresol purple; nitrazine yellow; or other sulfophthalein dyes.

Other embodiments include reagents printed on dressing or solid support materials, dipstick devices with indicator disks arranged in various arrays, and devices with separate sample preparation chamber that transfer a sample of a bodily fluid or wound fluid to a standalone diagnostic device that uses reagent pills, solutions, or disks in reaction chambers for detecting biomarkers associated with microbial detection. In further embodiments, indicator reagents are printed, sprayed, or overlayed on support materials, such as dressing, wound dressing, bandage, filter paper, and test strips.

Generally, when a pathogen encounters the human body interior, cells react through innate receptor systems, either to injury, toxins, or to the bacterial cell wall. All of these recognition events result in the recruitment of innate immune cells. These cells are stimulated by pathogens like bacteria to activate bacterial killing systems that are normally present in polymorphonuclear leukoctyes (PMNs) and are mainly enzymatic in character. The cells engulf bacteria and lyse them with enzymes that hydrolyze proteins (e.g., protease, elastase, cathepsin G) and cell walls (lysozyme), or mediate protein denaturation (NADPH oxidase, xanthine oxidase, myeloperoxidase (MPO)). These PMNs are generally only short lived and will themselves lyse in the area of the infection. When they lyse, they release the contents of their lysosomes including the enzymes.

These enzymes are, therefore, biomarkers for the presence of myeloid cells, and PMN s in particular. A rising level of these enzymes in the wound fluid, therefore, corresponds to a heightened bacterial challenge and one that is not being adequately met by the innate defense. The association of these enzyme levels with clinical infection has been validated using a clinical trial approach (Blokhuis-Arkes et al., 2015).

In addition, the pH of a wound can influence many factors of wound healing, such as angiogenesis, protease activity, oxygen release, and bacterial toxicity. Chronic non-healing wounds, and those that are infected or at risk of infection, typically have an elevated alkaline environment. As the wound progresses towards healing, the pH of the wound moves to neutral and then becomes acidic. Monitoring of the pH of the wound may provide a method to assess the condition of the wound (e.g., infection or no infection) and aid in determining a wound's response to treatment.

A typical lateral flow device utilizes the concept of lateral liquid flow in order to transport a given sample to the test. The benefits of lateral flow tests include rapid results, long-term stability and low cost to manufacture. These features make lateral flow tests well-suited for applications involving drug testing in urine, in particular with rapid point of care testing in hospitals and doctor's offices being an advantage. A test strip can be dipped directly in the sample which is taken in a liquid form. The sample travels up the lateral flow strip and binds to available antibodies, which causes a reaction that can be visually detected on the strip. Applying this technology to samples other than urine or blood has however been problematic.

Early detection of markers for infection in wounds has advantages in that treatment of infection can be commenced before the infection becomes established and other signs of infection become apparent, for example, discharge from the wound, redness, pain and unpleasant odor. A difficulty in testing for markers in wound fluid is that wound fluid differs greatly in its consistency and quantity. For instance it can be scant but viscous making the use of a lateral flow test difficult.

Thus it would be desirable to have a single kit for collecting and testing a sample of fluid taken from a wound that is easy to operate and not limited by the type or quantity of exudate from the wound. One embodiment of the stand-alone device kit described herein mitigates the above problems in a kit which comprises a sampling component and a test device where the test device does not rely on a lateral flow strip to move the sample through the device and achieve a diagnosis.

Wound Dressing

In some embodiments, the wound dressing comprises a wound contacting layer; a reagent layer comprising one or more testing regions; and an outer layer that overlays the reagent layer. In some embodiments, the wound dressing further comprises a protective cushioning layer (for example a foam or a nonwoven layer) between the wound contacting layer and the reagent layer. In some embodiments, the wound dressing further comprises one or more lines of wicking stitching or wicking tufting throughout all layers of the wound dressing except the outer layer. In some embodiments, the wound dressing comprises perforation through the wound contacting layer, the protective cushioning layer, or a combination of both. In some embodiments, such perforation allows for wound fluid transfer from the wound to the reagent layer.

Wound Contacting Layer

When in use, the wound contacting layer of the wound dressing absorbs wound exudate and/or wound fluid. In some embodiments, the wound contacting layer comprises gel-forming polymers or hydrofiber. Gel-forming polymers include, but are not limited to cellulose, carboxymethylcellulose (CMC), carboxyethylcellulose, oxidized cellulose (or a derivative thereof), cellulose ethyl sulfonate, other chemically modified cellulose, pectin, alginate, chitosan, modified chitosan, hyaluronic acid, polysaccharide, or gum-derived polymer, or any combination thereof. In some embodiments, the wound contacting layer may comprise polyvinylpyrrolidone, polyvinyl alcohols, polyvinyl ethers, polyurethanes, polyacrylates, polyacrylamides, collagen, gelatin or mixtures thereof. In some embodiments, the wound contacting layer comprises fibers of gel-forming polymers. In some embodiments, the wound contacting layer comprises a nonwoven layer of gel-forming fibers.

In some embodiments, the wound contacting layer further comprises non-gel-forming polymers. In some embodiments, the wound contacting layer comprises cellulose (for example, Lyocell), modified cellulose (for example, viscose or rayon), Polyester, silk, wool, Nylon, Polypropylene, Elastane or mixtures thereof.

In one embodiment, the thickness of the wound contact layer is from 0.1 to 10 mm, in a preferred embodiment it is from 0.1 to 5 mm and in a still more preferred embodiment it is from 0.3 to 3.5 mm.

Protective Cushioning Layer

In some embodiments, the protective cushioning layer provides mechanical protection of the wound and also assists in the management of excess exudate by acting as a large surface area for evaporation. In some embodiments, the protective cushioning layer may also serve as the material that accepts fluid exiting reagent layer or device and may add functionality by pulling or directing fluid through the reagent layer or device. Suitable materials include foams, (non-gelling) fiber fleeces, (non-gelling) nonwoven fabrics, and engineered three-dimensional fabric structures, such as corrugations. Examples of engineered three-dimensional fabric structures are shown at FIG. 1. Preferably, materials used for the protective cushioning layer possess mechanical cushioning properties that are unaffected or are minimally affected by contact with wound exudate. In some embodiments, the protective cushioning layer comprises plastics based on olefins or olefin derived polymers, such as polyethylene, polypropylene, nylon, polyurethane, polystyrene and polyvinyl chloride. In some embodiments, these materials may further comprise agents such as surfactants or absorbents that improve their wettability.

In some embodiments, hydrophilic polyurethane foam is 2.5 mm (+/−0.5 mm) thick, with a density of 90 kg/m$^3$ to 150 kg/m$^3$, absorption of ≥12 g/g.

Wicking Stitching and/or Wicking Tufting

In some embodiments, the transfer of wound fluid to the reagent layer is optimized by fiber tufts from the wound contact layer to the reagent layer. In some embodiments, gel forming polymers from the wound contact layer can be used as the transport mechanism of fluid from the wound to reagent layer. In some embodiments, the increased hydrophilic nature of gel forming polymers in comparison to materials within alternate layers of the dressing allows enhanced wicking action to the reagent layer.

In some embodiments, yarns can be used to provide capillary action of fluid from the wound contact layer to the reagent layer. This can be achieved using stitching of one or more layers of the dressing or using tufting of yarn through one or more dressing layers.

In some embodiments, the wicking stitching and/or wicking tufting is selected from various fibers that are wettable and exhibit capillary action. Such fibers include, but are not limited to, cotton, rayon, viscose, wool, silk, polyester, polyamide, and CMC fibers, solid and hollow fibers. In some embodiments, the wicking stitching comprises cotton, polyester, polyamide, polypropylene, or a combination thereof. In some embodiments, using increased number of plies or multifilament yarn, increased linear density of yarn, and/or decreased linear density of fiber may enhance capillary action of yarn. In some embodiments, the wicking stitching comprises cotton. In some embodiments, the wicking stitching comprises polyester. In some embodiments, the wicking stitching comprises polyamide. In some embodiments, the wicking tufting comprises CMC fibers. In some embodiments, the wicking occurs across all areas of the dressing layers. In some embodiments, the wicking is concentrated immediately beneath or adjacent to the reagent layer to provide focused, enhanced wicking action and/or reaction with the reagent layer.

In some embodiments, stitching of yarn through hydrofiber and/or foam layer using hydrophilic yarn provides wicking capacity. The wound fluid can be wicked up by yarns in a more direct route to the printed substrate or reaction layer. Increase in yarn linear density may allow more of a decrease in wicking time and/or amount of fluid required.

In some embodiments, needling of hydrofiber-foam laminate in wound dressing creates tufts of hydrofiber on the foam side of the dressing. Variable parameters of needling include punch density and penetration depth, such as 10-100 punches/cm$^2$ at 1-10 mm penetration, 20-90 punches/cm$^2$ at 2-9 mm penetration, 30-80 punches/cm$^2$ at 3-8 mm penetration, 40-80 punches/cm$^2$ at 4-8 mm penetration, 50-80 punches/cm2 at 5-8 mm penetration, 60-80 punches/cm$^2$ at 6-8 mm penetration, 70 punches/cm$^2$ at 6 mm penetration. Channels of hydrofiber are created through the foam, leading to vertical wicking of fluid. Hydrofiber tufts may enable quicker fluid and enzyme transfer. Type of needles used for tufting include felting (crown), felting (regular), and fork. In some embodiments, use of felting needles allowed gelling fiber tufts to be created through the foam layer without causing a detrimental effect on the foam or gelling fiber. Penetration depth may be 1 mm, 2 mm, 3 mm, 4 mm, 5 mm, 6 mm, 7 mm, 8 mm, 9 mm, 10 mm, 11 mm or 12 mm, or at least 6 mm, or less than 7 mm, less than 8 mm, less than 9 mm or less than 10 mm. Preferably, penetration depth is 6 mm, which enabled an 18% decrease in vertical wicking time at 70 p/cm$^2$ punch density. As punch density increases, more hydrofiber tufts are created on the foam layer. Enhanced fluid transfer was seen in all punch densities at 6 mm penetration depth.

In some embodiments, stitching of yarn through hydrofiber and/or foam layer using hydrophilic yarn provides wicking capacity. Stitches may be about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, at least about 5 mm, less than about 6 mm, less than about 7 mm, less than about 8 mm, less than about 9 mm or less than about 10 mm. The wound fluid can be wicked up by yarns in a more direct route to the printed substrate or reaction layer. Increase in yarn linear density allows more of a decrease in wicking time and/or amount of fluid required. Short stitches (less than 3.5 mm) do not reduce wicking time/volume required to wick through the foam layer. Stiches may be 5 mm to allow a reduction in wicking time by about 45%. In some embodiments, hydrofiber-foam laminate material with combined thickness of 4.3 mm was tested for stitching with two types of yarn: high wicking polyester (continuous filament) and standard polyester thread. Three stitch lengths were tested, including 2.5 mm, 3.5 mm, and 5.0 mm. Incorporating stiches enhances fluid transfer, while increasing stitch lengths reduced vertical wicking time.

Perforation

In some embodiments, the wicking action of the various layers of the dressing, such as the gel-forming wound contacting layer and the foam, is adequate as it is with the factory porosity and no further treatment. In other embodiments, the wicking action can be enhanced by fine needling to create channels that have capillary action. In some embodiments, the needling can occur across all areas of the dressing layers to provide generally enhanced capillary action. In some embodiments, the needling is concentrated immediately beneath or adjacent to the common entrance to the reagent layer to provide focused, enhanced capillary action. In some embodiments, the perforation occurs through all layers of the dressing. In further embodiments, the perforation occurs in the one or more layers between the wound contact layer and the reagent layer. In some embodiments, capillary action can be enhanced by increasing the punch density of the needling to produce higher number of perforations per unit area.

Perforations allow direct fluid transfer through hydrofiber and/or foam layers to the printed substrate layer. The larger the hole, the more fluid may be transferred, reducing the wicking time/volume required for the fluid to interact with the printed substrate layer. However, if the hole is too large, fluid handling capacity of the dressing may be affected. Gelling fibers swell upon hydration and may obstruct the perforation channel of the gelling fabric. Perforations may be formed using a hypodermic needle. At a higher density, the vertical wicking time can be reduced by about 28%. In some embodiments, the vertical wicking time is reduced by about 10%, about 15%, about 20%, about 25%, about 30%, about 35%, about 40%, about 45% or about 50%.

Reactive or Reagent Layer

In some embodiments, the wound contact layer, or the layer supporting it contains a material that reacts to wound exudates to indicate potential infection, or a reactive layer. A reactive layer may comprise one or more dyes and/or the reagents necessary to support these reactions. In one embodiment, these dyes comprise amino acids, peptides, or proteins conjugated to dyes with strong ionic functions, strong contrasting colors, or the ability to form colors, such as indoxyl/indigo. In a preferred embodiment, addressing includes a layer within the dressing printed with an immobile trapping material to which said dyes bind. This layer is optionally in the outer part of the dressing or at various levels within the dressing such that it may be observed without dressing change, or at dressing change.

In another preferred embodiment, the reactive layer is comprised of an MPO substrate, glucose oxidase and an energy source, such as glucose or starch, and gammaamylase. In another embodiment, the dressing contains particles comprised of chitosan or a derivative that releases dyes on hydrolysis by lysozyme. These dyes may be highly charged or otherwise functional to allow their accumulation at sites of signal interpretation. In yet other embodiments, the reactive layer comprises compounds such as p-aminophenol, ABTS (2,2inophenol, ABTS (strate. In some embodiments, acid) diammonium salt), 3,3'-diaminobenzidine, 3,4 diaminobenzoic acid, DCPIP, N,N-dimethyl-pphenylenediamine, o-dianisidine, p-phenylenediamine, 4-chloro-1-naphthol, o-phenylenediamine N-(4-aminobutyl)-N-ethyl-isoluminol, 3-amino-9-ethylcarbazole, 4-aminophthalhydrazide, 5-aminosalicylic acid, 2,2'-azino-bis(3-thylbenzothiazoline-6-sulfonic acid), indoxyl, indigo, Fast Blue RR, 4-chloro-7-nitrobenzofurazan. In some embodiments, the reactive layer comprises an arylamine. In some embodiments, the reactive layer comprises an amino phenol. In some embodiments, the reactive layer comprises an amino phenol an aminophenol ether. In some embodiments, the reactive layer comprises an indoxyl. In some embodiments, the reactive layer comprises an a neutral dye. In some embodiments, the reactive layer comprises a charged dye, e.g., a dye selected from remazole brilliant blue, toluidine blue, reactive black 5, remazol brilliant blue, reactive violet 5, and reactive orange 16, or a hydrolytic or ammonolytic derivatives thereof, toluidine blue, reactive black 5, or ahydrolytic or ammonolytic derivatives thereof; reactive violet 5, or hydrolytic or ammonolytic derivatives thereof; reactive orange 16, or hydrolytic or ammonolytic derivatives thereof; a dichlorotriazine-based reactive dye such as reactive blue 4, reactive red 120, reactive blue 2, reactive green 19 and reactive brown 10. In some embodiments, the dichlorotriazine-based reactive dye appears black.

In particular embodiments, the reactive layer comprises compounds such as a reactive dye containing a sulfonyl-ethyl-hydrogensulphate-reactive-group. In some embodiments, the reactive dye is reactive black 5, remazol brilliant blue, reactive violet 5 or reactive orange 16. In some embodiments, the reactive dye is reactive black 5. In some embodiments, the reactive dye is remazol brilliant blue. In some embodiments, the reactive dye is reactive violet 5. In some embodiments, the reactive dye is reactive orange 16. In some embodiments, the reactive dye is reactive black 5, remazol brilliant blue, or reactive violet 5. In some embodiments, the reactive dye is reactive black 5 or remazol brilliant blue.

In some embodiments, the reactive layer comprises a nanoparticle. In some embodiments, the reactive layer comprises a colloidal gold particle. In some embodiments, the reactive layer comprises a charged dye, an indole derivative, or a luminol derivative. Especially, the reactive layer comprises a dye containing a sulfonylethyl-hydrogensulphate-reactive-group, e.g., reactive black 5, remazol brilliant blue, reactive violet 5 or reactive orange 16, or a combination thereof, or a dye containing a dichlortriazine reactivegroup, e.g., reactive blue 4, reactive red 120, reactive blue 2, reactive green 19 and reactive brown 10, or a combination thereof.

FIG. 3 shows two embodiments of a reaction cell, comprising indicator units or testing regions. In (A) of FIG. 3, stitching (21) using wicking fibers helps to draw wound or bodily fluid from a wound toward a reagent pad (22), then through testing regions (23 and 24) and toward absorbent or evaporation area (25). In (B) of FIG. 3, a perforation or cut access (27) is made, such as in the reagent pad (22) to allow the flow of wound fluid from the wound to the reagent pad via capillary action. The reagent pad (22) may comprise reagents that react with microbial biomarkers in the wound fluid, such as substrates that react with MPO (29), elastase (30), and lysozyme (31) in the wound fluid. In some embodiments, one or more testing regions may comprise a sulfonic acid filter pad (23) and a quaternary amine trap (24). In some embodiments, one or more testing regions comprise a leach-back trap (28) and an amine back flow trap or filter (29). Some embodiments contain pH indicators (32) and protein indicators (33) that allow a user to detect a visible signal resulting from reactions between microbial biomarkers in the wound fluid and the reagents in the reagent pad (22). Absorbent or evaporation area (25) helps to draw the flow of the fluid from the reagent pad (22) toward (25). In a preferred embodiment, impermeable separators (26) keep adjacent testing regions separate.

In some embodiments, the indicator trap catches reaction products between the wound fluid and the one or more components selected from the group consisting of enzyme-reactive indicators, reagents that are sources of peroxide, enzymes that are able to transform color reactions, pH indicators, and moisture-detecting reagents. In some embodiments, the indicator trap comprises a positively charged or negatively charged trap for reaction products. In some embodiments, the positively charged trap comprises a quaternary amine polymer, a mixture of secondary and tertiary amines, other amine-containing polymers, or a combination thereof. In some embodiments, the positively charged trap comprises polyDADMAC, or an analog thereof. In some embodiments, the negatively charged trap comprises polymers or reagents containing carboxy, sulfate, sulfonate, or other acidic chemical groups. In some embodiments, the negatively charged trap comprises styrene sulfonate. In some embodiments, the indicator trap comprises a total protein indicator which is eluted by wound fluid to indicate overall flow and capacity of the testing region. In some embodiments, the control region contains a substrate for a ubiquitous enzyme such as esterase or carbonic anhydrase, or an indicator for a ubiquitous metabolite like lactate, glucose, ammonia or lipid. In some embodiments, one or more testing regions comprise a sulfonic acid filter pad and a quaternary amine trap. In some embodiments, one or more testing regions comprise a leach-back trap, a sulfonic acid filter pad and a quaternary amine trap. In some embodiments, each of the one or testing regions is used to evaluate the presence of one or more analytes and one or more positive or negative control indicators. In further embodiments, the one or more analytes is associated with enzyme activity. In some embodiments, the enzyme is selected from one or more of the group consisting of elastase, lysozyme, cathepsin G, myeloperoxidase, and leukocyte peroxidase. In some embodiments, the enzyme is elastase. In some embodiments, the enzyme is lysozyme. In some embodiments, the enzyme is cathepsin G. In some embodiments, the enzyme is myeloperoxidase. In some embodiments, the enzyme is leukocyte peroxidase.

In some embodiments, the wound dressing comprises a reagent layer comprising one or more testing regions. In some embodiments, the reagent layer comprises a support material. In some embodiments, the support material comprises a woven or non-woven material that is capable of being wet by a wound fluid and which displays capillary action. In a preferred embodiment, the capillary action is uniform in the plane of the material. In a preferred embodiment, the test regions are arranged in a circle so that diffusion occurs radially when a liquid is applied. Support material includes, but is not limited to, paper, cellulose, cellulose derivatives, viscose, polyamide, polyester, polyacrylate, and other similar polymers that are useful as fibers, and any combination thereof. In some embodiments, the support material is cellulose-based, such as refined papers, or non-woven material containing bonded cellulose fibers. In some embodiments, the support material is polyamide. In some embodiments, the support material is polyester. In some embodiments, the support material is polyacrylate. In some embodiments, the role of the solid support is to adhere substrates and provide a field in which analyte enzymes can travel to and interact with the detector. In some embodiments, cellulose content aids adherence of the enzyme substrates, and a significant cellulose or cellulose like content is preferred.

In some embodiments, each of the one or more testing regions is printed on or in the support material. In some embodiments, each of the one or more testing regions comprises an inlet for wound fluid, an area for the wound fluid to react with reagents (e.g., a reagent pad), an area to observe each product of one or more reactions, and an area for the accumulation of excess wound fluid (e.g., an absorbent area), which is then evaporated from an area sufficiently large as to not block due to accumulated solutes. In some embodiments, the evaporation zone helps to drive pull-through of more wound fluid.

FIG. 4 shows multiple embodiments of the movement of indicators in various reaction cells. When testing regions in the embodiment of (A) of FIG. 4 are exposed to wound fluid, wound fluid flows from the reagent pad (22) to absorbent or evaporation area (25), as shown in the right panel of FIG. 4(A). The embodiment of (B) of FIG. 4 shows an embodiment of reaction cells wherein indicators are arranged in a radial arrangement, and wherein fluid flows outward from the center upon encountering the reagent pad. The embodiments of (C) of FIG. 4 illustrates how multiple reaction cells can be used to cover a broader area, with trap leach-back (41) preventing backflow. In some embodiments, each reagent cell or lane of reagent pad (22) may be a different reporter or color system, such as bromothymol blue, phenol red, bromophenol red, chlorophenol red, thymol blue, bromocresol green, bromocresol purple; nitrazine yellow; or other sulfophthalein dyes. In the presence of wound fluid, in one embodiment reagents interact with analytes in the wound fluid and migrate or diffuse toward the absorbent or evaporation area (25).

In some embodiments, reagents are used that require trapping of the reaction product, and, to this end, each of the one or more testing regions comprises a reagent pad or a reagent cell (22), a filter pad (23), an indicator trap (24), and an absorbent/evaporation area (25). In embodiments comprising a color change reagent, each of the one or more testing regions comprises a reagent pad that is also under a viewing window and an absorbent/evaporation area. In some further embodiments, each of the one or more testing regions comprises a leach-back trap which is a trap field that contains an absorbent that absorbs the reagents and prevents their back flow to the dressing below. In some embodiments, an outer layer overlays the reagent layer in order to modulate evaporation of wound fluid, the outer layer containing one or more windows to visualize the underlying indicator trap and/or reagent pad from one or more testing regions.

In some embodiments, each of the one or more testing regions detects at least one biomarker. In some embodiments, each of the one or more testing regions comprises one or more impermeable separators, wherein each of the one or more testing regions detects more than one biomarker. In some embodiments, the one or more impermeable separators are printed strips of hydrophobic non-permeable material. In some embodiments, the one or more impermeable separators are arranged in parallel lanes. In some embodiments, the one or more impermeable separators are arranged in a radial pattern. In some embodiments, each of the one or more testing regions detects two biomarkers. In some embodiments, each of the one or more testing regions detects three biomarkers. In some embodiments, each of the one or more testing regions detects four biomarkers. In some embodiments, each of the one or more testing regions detects five biomarkers. In some embodiments, each of the one or more testing regions detects six biomarkers. In some embodiments, each of the one or more testing regions detects seven biomarkers. In some embodiments, each of the one or more testing regions detects eight biomarkers. In some embodiments, each of the one or more testing regions detects nine biomarkers. In some embodiments, each of the one or more testing regions detects ten biomarkers. In some embodiment, each of the one or more testing regions detects one or more biomarkers.

FIG. 5 shows a radial arrangement of indicators or a radial indicator patch. As shown in (A) of FIG. 5, testing regions or reagents may be arranged in a circular or radial orientation. The indicator includes reagents (22), a quaternary amine trap (24), and an absorbent or evaporation area (25). A hole or cut access (27) in the middle of the indicator helps to draw fluid from a wound into the indicator. The fluid typically will flow from the access (27) outward to the evaporation area (25). When reagents (22) are exposed to wound fluid and react to microbial biomarkers, the resulting products migrate to amine trap (24), allowing detection by a user. The indicator may also have impermeable separators or lanes (26). As shown in (B) of FIG. 5, a top or "above" view is provided and a bottom or "below" view is provided for a radial indicator patch. In one embodiment, substrates may be printed as dots to allow for greater freedom of printing. Moisture impermeable film with adhesive on both sides allows the radial indicator patch to attach to foam or other support material. In some embodiments, each reaction cell or lane (45-48) can be a different reporter or color system, allowing analysis of multiple analytes on one indicator patch.

In some embodiments, each of the one or more testing regions comprises one or more components selected from the group consisting of enzyme-reactive indicators, reagents that are sources of peroxide, enzymes that are able to transform color reactions, pH indicators, total protein-detecting reagents, and moisture-detecting reagents. In some embodiments, the reagents that are sources of peroxide are selected from peroxy acids, sodium percarbonate, and peroxide-generating oxidases, such as glucose oxidase or lactate oxidase. In some embodiments, the enzymes that are able to assist the transformation of color reactions are selected from peroxidases and laccases. In some embodiments, one or more components are immobilized within the one or more testing regions. In some embodiments, one or more components are mobilized by wound fluid within the one or more testing regions. In some embodiments, one or more components bind to the one or more testing regions due to interaction with wound fluid. In further embodiments, each of the one or more testing regions further comprises one or more of the group consisting of buffers, binders, and solubility enhancers. In some embodiments, one or more buffers, binders, and/or solubility enhancers improves printing or stability.

In some embodiments, each of the one or more testing regions comprises an enzyme-reactive indicator, further comprising an enzyme-labile or enzyme-reactive moiety, an immobilizing moiety that holds the reactive indicator in place, and a moiety that gives rise to a visible change upon interaction of the reactive indicator with a target enzyme. In some embodiments, each moiety is distinctly different from the other. In some embodiments, one moiety incorporates another moiety either partially or entirely. In some embodiments, the reagent pad comprises one or more enzyme-reactive indicators.

In some embodiments, the enzyme-reactive indicator is a protein-indicator conjugate such as a protease substrate comprising both protein and dye materials. In a preferred embodiment, the protein-indicator conjugate is a protein with a binding function to a solid phase, such as a cellulose binding domain conjugated with a protease recognition site and dyes that are released upon proteolysis.

In some embodiments, the pH indicator presents a visible color change at alkaline pH. In some embodiments, the pH indicator presents a visible color change at pH=7.2-9.5. In some embodiments, the pH indicator presents a visible color change at pH=7.2-9.0. In some embodiments, the pH indicator presents a visible color change at pH=7.2-8.5. In some embodiments, the pH indicator presents a visible color change at pH=7.2-8.0. In some embodiments, the pH indicator presents a visible color change at pH=7.5-8.5. In some embodiments, the pH indicator presents a visible color change at pH=7.5-9.0. In some embodiments, the pH indicator presents a visible color change at pH=8.0-9.0. In some embodiments, the pH indicator presents a visible color change at pH=7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5, or increments thereof.

In some embodiments, the pH indicator presents a visible color change at neutral pH. In some embodiments, the pH indicator presents a visible color change at pH=6.9, 7.0, or 7.1, or increments thereof.

In some embodiments, the pH indicator presents a visible color change at acidic pH. In some embodiments, the pH indicator presents a visible color change at pH=4.5-6.8. In some embodiments, the pH indicator presents a visible color change at pH=4.5-6.5. In some embodiments, the pH indicator presents a visible color change at pH=5.0-6.8. In some embodiments, the pH indicator presents a visible color change at pH=5.4-6.8. In some embodiments, the pH indicator presents a visible color change at pH=5.4-6.5. In some embodiments, the pH indicator presents a visible color change at pH=4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or increments thereof.

In some embodiments, the pH indicator is nitrazine yellow, bromocresol purple or bromothymol blue or an analog thereof.

In some embodiments, the filter pad removes unwanted components of wound fluid, such as fibrinogen, albumins or globulins, and cellular components or non-cellular debris, i.e., dressing components, medicaments, metabolites, microbes, microbial debris, microbial metabolites, etc. In some embodiments, the leach-back trap prevents backflow of reagents in the reagent pad or reagent cell from entering the inlet for wound fluid in the testing region. In some embodiments, the filter pad and/or leach-back trap comprises a quaternary amine polymer, a mixture of secondary and tertiary amines, other amine-containing polymers, or a combination thereof. In some embodiments, the filter pad and/or leach-back trap comprises a quaternary amine polymer. In some embodiments, the filter pad and/or leach-back trap comprises a mixture of secondary and tertiary amines. In some embodiments, the quaternary amine polymer is polydiallyldimethylammonium chloride (polyDADMAC or polyDDA). In some embodiments, the mixture of secondary and tertiary amines is polyethylenimine (PEI). In some embodiments, the filter pad and/or leach-back trap is held in place by cross-linking with bifunctional reagents, such as epichlorhydrin, diglycidylethers, di-epoxides or arylazide-isothiocyanates. In some embodiments, such reagents when mixed with a reactive amine-containing polymer link different polymer chains and trap the longer polyDADMAC chains within a matrix. In some embodiments, the trap is composed of choline acrylate derivatives polymerized in situ using a radical initiator such as benzphenone. In some embodiments, the filter pad and/or leach-back trap comprises polymers or reagents containing carboxy, sulfate, sulfonate, or other acidic chemical groups. In some embodiments, the filter pad and/or leach-back trap comprises styrene sulfonate.

In some embodiments, the indicator trap catches reaction products between the wound fluid and the one or more components selected from the group consisting of enzyme-reactive indicators, reagents that are sources of peroxide, enzymes that are able to transform color reactions, pH indicators, and moisture-detecting reagents. In some embodiments, the indicator trap comprises a positively charged or negatively charged trap for reaction products. In some embodiments, the positively charged trap comprises a quaternary amine polymer, a mixture of secondary and tertiary amines, other amine-containing polymers, or a combination thereof. In some embodiments, the positively charged trap comprises polyDADMAC, or an analog thereof. In some embodiments, the negatively charged trap comprises polymers or reagents containing carboxy, sulfate, sulfonate, or other acidic chemical groups. In some embodiments, the negatively charged trap comprises styrene sulfonate. In some embodiments, styrene sulfonate is diluted to 0.02 to 0.8% in water and printed in this form to the support material. In yet other embodiments, styrene sulfonate is diluted to between about 0.01% to 2.0%, about 0.01% to 1.5%, about 0.01% to 1%, about 0.05% to 1%, about 0.1% to 1% or about 0.5% to 1%.

In some embodiments, the indicator trap comprises a total protein indicator which is eluted by wound fluid to indicate overall flow and capacity of the testing region. This region is distinct from the moisture indicator. In one embodiment, a blue polysulfonate dye, such as Evans or Trypan blue, is weakly bound to a tertiary amine trap. On arrival of protein, the dye is displaced and re-trapped as a Protein complex on a quaternary amine trap. In another embodiment, Coomassie Blue G250 is weakly bound to a Styrene sulfonate field and is displaced by protein to be re-trapped on a quaternary amine trap. The dye undergoes a mild color change from the sulfonic acid environment to the amine environment increasing the effect. In another embodiment, the visualization field is pre-printed with the Ponceau S complex of the quaternary amine trap such that it is red indicating non-function. The conversion of the trap to the Blue form indicates the progress of protein elution.

In an embodiment of an indicator of the arrival of fluid in the system, Brilliant Black or a similar dark tetra sulfonate is printed into a reagent pad as a free reagent without any polymer complexing. Being water soluble, it is readily mobilized by the wound fluid and migrates to the window where it is avidly trapped by a quaternary amine trap. The high polysulfonation increases the avidity for the amine and resists further elution by proteins. Under conditions of high secretion, the eventual removal of the dye from the trap may also serve to indicate exhaustion of the device or a need to change it.

In some embodiments, one or more testing regions comprise a sulfonic acid filter pad and a quaternary amine trap. In some embodiments, one or more testing regions comprise a leach-back trap, a sulfonic acid filter pad and a quaternary amine trap.

In some embodiments, each of the one or testing regions is used to evaluate the presence of one or more analytes and one or more positive or negative control indicators. In some embodiments, the one or more analytes is associated with enzyme activity. In some embodiments, the enzyme is selected from one or more of the group consisting of elastase, lysozyme, cathepsin G, myeloperoxidase, and leukocyte peroxidase. In some embodiments, the enzyme is elastase. In some embodiments, the enzyme is lysozyme. In some embodiments, the enzyme is cathepsin G. In some embodiments, the enzyme is myeloperoxidase. In some embodiments, the enzyme is leukocyte peroxidase.

In some embodiments, a positive result (e.g., indication of infection) from the one or more testing regions is in the form of a visible change. In some embodiments, the visible change is a color. In some embodiments, the color is selected from dark blue, dark green, and black. It is clear to those skilled in the art that the signal effect of the color change depends on context and practical consideration of interfering colors from the wound itself. Thus, red is a useful signal to indicate a problem, or to indicate stop or not ready, but it is readily confused with colors associated with wound fluids. Thus, colors that are not likely to emerge from a wound offer potentially less source of error. In some embodiments, the visible change is fluorescent, luminescent, or mediated by physical means such as electrical, refraction, gas evolution or polymer state change. Some fluorescent systems have the drawback that they require a source of light and potentially a darkened room or chamber for viewing, however, other fluorescent systems do not have such drawbacks. Conventional colors are visible under normal treatment conditions. Given that a color may be diluted or covered by fluids such as blood, there remains an embodiment in which a dual indicator is used in which a fluorescent indicator is mixed with a conventional color indicator. Thus, if a field is covered by blood, the result may be optionally interrogated with a black-light to determine whether a signal is present.

Outer Layer

In some embodiments, the outer layer comprises a polymer that is not easily penetrated by wound fluid. Such polymers include, but are not limited to, a polyolefin, a polypropylene, a polyethylene, polyurethane, polyamides, ethylene-vinyl alcohol (EVOH), acrylonitrile (PAN), polyvinyl choride (PVC), polyvinylidene chloride (PVDC), polyacrylates (e.g., (1-methyl-1,2-ethandiyl)bis[oxy(methyl-2,1-ethandiyl) diacrylate) or other similar hydrophobic impermeable polymers that, in some embodiments, are laid down as films by printing, spraying or film blowing. In some embodiments, the outer layer is water vapor permeable. In some embodiments, the outer layer prevents moisture loss in specific areas (e.g., where a visible change indicating infection is observed) and promotes moisture loss in other specific areas (e.g., where excess wound fluid accumulates).

In some embodiments, the reaction layer is protected by two layers: a top layer and a bottom layer. The bottom layer typically has an opening that allows fluid sample inflow. The top layer generally prevents premature evaporation of the sample and may force it to migrate through the device to the evaporation zone. The top layer may also contain one or more windows that allow the response of the reagents to be seen or detected.

Devices

In yet other embodiments, the disclosure herein provides a device comprising a sampling component and a test device comprising:

(a) a housing surrounding a tube to define an opening in the housing to receive the sampling component, the housing also having disposed within it:

(b) a sealed diluent chamber connected to the tube and holding a liquid diluent for removing the sample from the sampling tip to form a liquid test sample;

(c) a reaction well in liquid communication with the tube, the reaction well holding a reagent capable of indicating the presence of the analyte within the test liquid; and (d) a forcing mechanism capable of moving the diluent through the device from the chamber, over the sample tip and into the reaction well.

In some embodiments, the device operates by driving the diluent over the sample and into a reaction well, and a test solution is made by the flow of the diluent over the sample. Preferably, it is not necessary to first mix the sample with the diluent to make a test solution and then move that solution via a lateral flow strip to the reaction well. The moving of the diluent past the sample and to the reaction well means that the kit can be used with a minimum number of steps, for instance taking the sample, inserting the sampling component into the housing and activating the moving or driving mechanism. This procedure minimizes user error and thus minimizes false-negative results and misdiagnoses.

In some embodiments, the diluent is forced through the device in a one-step or multi-step process. For instance, in a one-step process, the diluent is forced through the device which creates a test liquid, which is forced into the reaction well. In a multi-step process, such as a two-step process, the diluent could first be forced through the device to a mixing chamber where a test liquid is prepared. That liquid could then be forced from the mixing chamber to the reaction well in a further step.

In another embodiment, the means of mixing and loading the sample may be achieved in a separate step to its analysis. In one embodiment, a sample swab is first inserted into a recipient fluid container, and then a coaxial plunger is pushed over the swab to eject diluted sample into the analysis device. In a preferred embodiment, gas is removed, such as by using Goretex membranes which are gas and vapor permeable but not permeable to liquid water. Said membranes can be used to degas both the sample as it is injected and to vent the fluid chambers where the assay takes place.

In one embodiment, preferably the diluted sample is distributed to each analysis chamber equally through microchannels. However, when each exit from a chamber contains a Goretex membrane, back pressure ensures that each chamber is only filled once. In a more preferred embodiment, the loss of liquid sample from the assembly is prevented by an absorbent between the last outlet and the exterior of the device.

In still other embodiments, the disclosure herein provides a kit for detecting an analyte or biological marker or target in a sample comprising:

(i) a sampling component comprising a sampling tip for collecting the sample and (ii) a test device comprising: a housing surrounding a tube to define an opening in the housing to receive the sampling component, the housing also having disposed within it: a sealed diluent chamber connected to the tube and holding a liquid diluent for removing the sample from the sampling tip to form a test liquid; a reaction well in liquid communication with the tube, the reaction well holding a reagent capable of indicating the presence of the analyte within the test liquid; and a forcing mechanism capable of moving the diluent through the device from the chamber, over the sample tip and into the reaction well.

The sealed diluent chamber may contain a specified volume of diluent so that an expected volume of test solution reaches the reaction well or wells. In addition the pathway between the diluent chamber and the reaction well is preferably vented at the reaction well end so that trapped air does not affect the flow of test solution through the device or prevent the test solution from reaching the reaction well or prevent the test liquid from correctly filling the reaction well.

The housing preferably has two parts which are capable of moving with respect to each other while remaining connected to one another. The action of moving the parts may provide the forcing mechanism by which diluent is moved through the device. The diluent may be driven through the device by compression of the diluent chamber which forces the diluent past the sample tip and to the reaction well or wells emptying the compression chamber. The compression of the diluent chamber can occur when the parts of the housing are moved with respect to one another such as by sliding one part past another. Alternatively the diluent can be pulled through the device again for example by moving parts of the housing with respect to one another.

The sampling component preferably comprises a handle and a sampling tip, the handle preferably comprising a seal which engages with the opening in the housing to seal the tube when the sampling component is fully inserted in the tube. The seal prevents escape of the sample and diluent from the device reducing the chance of cross contamination from the wound fluid. Preferably the seal and tube engage to lock the sampling component in the device and prevent removal of the sampling component once it has been used. This further reduces the chance of cross-contamination from the sampling component. The sampling component preferably activates release of the diluent from the diluent chamber.

The housing may comprise a locking mechanism which locks the housing in position once the driving mechanism has been activated and prevents reuse of the device. In this way it is immediately apparent that the device has been used and cannot be used again. This minimizes false results from, for instance, a device that has been mistakenly activated in transit or from reuse of a device whose reagents have been spent.

Preferably insertion of the sampling component in the device releases the seal on the diluent chamber. Preferably the seal is a ball valve or can be a film or membrane seal or a duck bill valve or other non-return valve known in the art which is activated when the sampling component is inserted in the device. The sampling component preferably bursts, punctures or displaces the seal on the diluent chamber.

Preferably the tube is the same or similar size to the sampling tip of the sampling component so that the act of inserting the sampling tip into the tube causes it to be scraped along the walls of the tube aiding the dispersion of the sample in the diluent once it is released from the diluent chamber and is flushed through the device. The diluent can be flushed along the whole length of the tube or only part thereof. The sizing of the sampling tip to match the tube also forces the diluent to be flushed through the tip when the diluent is driven from the diluent chamber. Preferably the tube is wider at its mouth to aid insertion.

Preferably the diluent chamber is shaped like a bellows to assist in the compression of the chamber alternatively the chamber can be a combination of a plunger and tube similar to that found in a syringe, or sample preparation device, or can be a filled flexible sachet which is compressed by hand by the user or a balloon which contracts when the seal is released.

Methods of Use

In one aspect, provided herein are methods to diagnose and indicate need for treatment of chronic wounds using a wound dressing described herein.

In some embodiments, the methods and devices disclosed herein detect biological markers or targets from body fluid. In some embodiments, the body fluid is blood, plasma, serum, cerebrospinal fluid, sputum, urine or wound exudate. In preferred embodiments, the body fluid is wound exudate.

In another aspect, provided herein are methods to diagnose chronic wounds using a wound dressing described herein.

In another aspect, provided herein are methods to indicate need for treatment of chronic wounds using a wound dressing described herein.

In another aspect, provided herein are methods to indicate need for treatment of surgical or acute wounds using a wound dressing described herein.

In another aspect, provided herein are methods of detecting biomarkers of infection in wounds using a wound dressing described herein.

In another aspect, provided herein are methods of detecting the pH and/or the presence of biomarkers of infection in wounds using a wound dressing described herein. In some embodiments, the biomarkers of infection are leukocyte enzymes. In some embodiments, alkaline pH in the wound indicates infection in the wound.

In another aspect, provided herein are methods of detecting protease activity in wounds using a wound dressing described herein.

In another aspect, provided herein are methods of monitoring the condition of a wound or surgical site and its healing process or status.

EXAMPLES

Example 1: Wound Dressing

One example of a construction of a wound dressing incorporating the device is shown in FIG. 2. The wound contact layer in this example is carboxymethylcellulose marketed as "AQUACEL", and the AQUACEL is backed by a polyurethane foam. In the infection-indicating area of the device is an impermeable area beneath the reagent layer. Connecting to this area is a material such as a polyester thread, methylcellulose fibers, or a similar wicking, hydrophilic, capillary or similar material, or capillary channels. This fluid connection brings wound exudate or fluid into contact with the reagent layer, where it may react with and mobilize indicator reagents into visible products that are either visible in place or trapped in window visible from the outside of the dressing. This example also demonstrates the use of AQUACEL.

In one embodiment of a wound dressing is shown in cross-section in FIG. 2. In that wound dressing the wound contact layer (4) comprises carboxymethylcellulose, marketed as AQUACEL. In FIG. 2, the wound contact layer (4) is backed by a polyurethane foam (3). In the infection-indicating area of the dressing is an impermeable area beneath the reagent layer (2) and above the polyurethane foam (3). Accordingly, in this embodiment the infection-indicating area is provided between the reagent layer (2) and the polyurethane foam (3). Connecting to the infection-indicating area is a fluid connection (1) component, such as a material such as a polyester thread, methylcellulose fibers, or a similar wicking, hydrophilic, capillary or similar material, or capillary channels (1). This fluid connection component (1) brings wound fluid into contact with the reagent layer (2), where it may react with and mobilize indicator reagents into visible products that are either visible in place or trapped in window (6) visible from the outside of the dressing as shown in the top view of the wound dressing shown in (C) of FIG. 2. As explained above, views (A) and (B) of FIG. 2 show side views of the wound dressing (7). View (B) of FIG. 2 shows the flow of wound fluid (5) from the wound contacting layer (4) at the bottom upward via capillary channels (1), which may be formed by stitching using wicking fibers. The wound fluid reacts with reagents in reagent layer (2), which may contain windows (6), allowing users to observe a visible signal resulting from reactions between wound fluid and reagents in the wound dressing. View (C) of FIG. 2 shows a top view of a wound dressing (7), wherein an opaque film on top of the reagent layer (2) contains windows or clear areas (6) that allow the observation of indicators or changes associated with reagent interaction with an analyte. In some embodiments, a visible signal may be a color change indicative of a microbial infection in the wound.

Example 2: A Dressing Material Printed with a Patterned Reactive Ink to Report MPO Activity A dressing wound contact layer has an upper and lower surface in which the lower surface is the wound contact layer. Reagents can be sprayed or printed on a wound dressing material. One embodiment of such dressing is shown in FIG. 6, wherein (A) depicts a view of the surface of the wound dressing material and illustrates the topside of wound contact material; (B) represents the wound material sprayed with amylase, starch, and glucose oxidase; and (C) represents substrate-printed in the centers of the sprayed area.

In alternate embodiments, onto the upper surface are printed multiple layers, such as three layers, to report MPO activity. In one embodiment the first layer is the substrate which is printed on the upper surface of the wound dressing material, such as at a concentration of 30 mg/mL in ethanol/heptane using a line width of 0.8 mm and a print density of 1 µLiem. Alternatively, the fast blue substrate is printed a grid of circles each 3 mm in diameter (FIG. 6). In one embodiment the next layer is a spray application of a solution of gamma-amylase and glucose oxidase immobilized on hydoxypropyl cellulose. The material may be sprayed in a water buffer solution such that approximately 3 µg of glucose oxidase is deposited per cm2, in parallel, 0.5 µg/cm2 of gamma amylase is applied as the conjugate. Once dried, a starch suspension may be sprayed at a density of 150 µg per cm2. Once printed, the wound contact layer is preferably bonded to an upper protecting layer. The same printing regime can be printed on the upper side an upper protecting layer. When exposed to artificial wound fluid containing enzymes, the grid becomes blue colored over time.

Example 3: An Absorbent Material Printed with a Patterned Reactive Ink to Report Elastase Activity In this example a dressing has an absorbent and protective layer which has an upper and lower surface in which the lower surface contacts the wound contact layer. Onto the upper surface a grid pattern is printed with 1 cm grid spacing. In one embodiment, as shown in FIG. 8, the print is performed with a solution of the AAPV-indoxyl ester 30 mg/mL in heptane/butanol using a line width of 1 mm and a print density of 1.3 µLiem. FIG. 7 illustrates embodiments of in-place color development of MPO and elastase substrates.

Example 4: A Multi-Biomarker Device Insert

The visualization methods are preferably either a color change of an immobile enzyme substrate, directly printed in the window of the reporter area, or of the appearance of an immobilization of the substrate caused by hydrophobic properties of the substance and non-covalent chemical interactions with the carrier material. The amount of applied substrate and possible impregnation mixtures for color improvement were tested in this example as described below Optimization of the reporter area and color signal: Circles (diameter 5 mm) were punched out of carrier material, in this case filter paper. Circles were impregnated with different mixtures of buffers (see specific reagents: Artificial wound fluid 2% bovine serum albumin in phosphate buffered saline containing potassium chloride, urea pH 7.2). See FIG. 8 for examples of substrates in a water solution followed by a drying step. After drying, varying amounts of substrate, usually in an organic solution, were pipetted on the test circles.

The reactivity to wound fluid was tested as follows: 10 µL test liquid (buffer or artificial wound fluid 2% albumin) with or without enzyme were pipetted on the dried test disks. Disks were incubated either in open air or in a closed system. Color development was evaluated visually at various times after initiation. All observations were at room temperature to simulate the condition expected outside the dressing.

After optimization of the two visualization methods, prototypes were prepared in lab scale to test the interaction of the different enzyme substrates/their color development. Prototypes were designed and assembled as described in FIGS. 7 and 9.

FIGS. 7 and 9 show embodiments of in-place color development of different indicators. FIG. 9 shows a prototype with the reporter areas for lysozyme, elastase and MPO detection, a pH indicator and the liquid control was constructed. On the left portion in (A) the diagnostic material is shown. On the right portion in (A) a magnification of the reporter area is shown. (B) shows the diagnostic area after liquid application (artificial wound fluid 0.5% albumin, 1 U/mL elastase, 10 µg/mL MPO, 30000 U/mL lysozyme). The experiment was run over 2 h with a flow rate of 100 µUmin for the first 10 min, followed by 10 µUmin. The experiment was repeated in n=10.

Embodiments of diagnostic inserts or disks are shown in FIGS. 10, 11, and 12. FIG. 10(A) shows the top view of a diagnostic insert, comprising a reporter area (60), reaction area (61), and evaporation area (62). FIG. 10(B) shows the bottom layer, comprising an impermeable layer of plastic film, either white or transparent, with a diameter of about 40 mm. The hole in the middle allows for liquid transport and has a diameter of about 4 mm. The bottom layer is covered with adhesive and in the same shape underneath for an exact fixation on a dressing. FIG. 10 shows embodiments of the reaction material comprising an adhesive layer (C) and a reaction layer (D), wherein each arm has a different substrate/indicator and/or pH system. FIG. 10(E) shows the cover, which comprises an impermeable white plastic foil with a diameter of 20 mm. The outer ring may have an insider diameter of 25 mm and an outer diameter of 31 mm. The top layer may be covered with adhesive underneath for an exact fixation on the reaction material.

Top view of the assembled completed diagnostic insert. See FIG. 10(A). The reporter area is designed as a window surrounded by an off-white layer to achieve a maximum contrast to the color signals. In this embodiment, there are five radial arms, each of which contains a different reporter and color system. In one embodiment, three are for enzymes and two are for controls.

The evaporation area ensures a continuous liquid transport through the diagnostic material, necessary for the enzyme reaction and color development in the reporter area.

Bottom layer as liquid barrier between the dressing and the diagnostic material. Liquid will preferably pass only through the hole in the middle of the layer which leads to a directed radial distribution into the arms of the reaction material (diagnostic material).

Diagnostic material was designed with four or five radial "arms" depending on the favored number of enzyme-substrates and controls to be included. The reaction material is fixed on the bottom layer with medical adhesive. Alternatively, the reaction arms are printed or coated with the less permeable bottom layer in place of the adhesive (one material can serve both purposes).

In some embodiments, the device insert comprises at least one arm or fewer than ten arms. The number of arms may depend on the number of analytes to be determined in a sample and control(s), as applicable. In further embodiments, the device insert comprises one, two, three, four, five, six, seven, eight, nine, or ten arms.

The reaction material is prepared with impregnation mixtures and substrates in accordance to the optimized conditions described above before assembling the detection material.

As shown in FIG. 10(E), the cover has several functions. Firstly, it preferably maintains the reaction zone moist by preferably preventing premature drying. Fluids should pass through the reaction area into the reporter area where there is a transparent window that allows color changes to be seen. The second function is preferably to avoid a stop of liquid flow and to cover the chemistry area so that colored reagents are not seen before they are transported to the window. The cover is water impermeable and includes the windows for signal visualization.

The detection material is preferably fixed with a medical adhesive to the foam backing layer of a hydrofiber dressing.

Optimization of the first visualization method (accumulation and trapping) established the following conditions:

Trapping mixture: Volume of 1.5 µL per 10 mm2, thickener Methylcellulose (Methocel A4C) max. 1.25%. Drying at room temperature for at least 1 h.

Transport of Remazol Brilliant Blue (FIG. 13) and visualization in the trap coated reporter area containing the amino-trap (triplicates), test liquid was artificial wound fluid 2% albumin. This visualization method was used for the Lysozyme-substrate (results obtained by QZY); released and trapped dye after enzyme cleavage: Remazol Brilliant Black) and the liquid control (dye: Brilliant Black BN).

FIG. 13 shows visualization of dye in reporter area (D) after exposure of reaction area (C) to artificial wound fluid. The direction of the fluid flow was from reaction area (C) to reported area (D), further comprising amino trap. The experiment was done in triplicates.

Optimization of the second visualization method (in-place color change) led to clearly colored signals for the MPO-substrate, the elastase substrate and a pH Indicator.

MPO-substrate: The MPO substrate in this example is a Fast Blue derivative. The substrate is soluble in 50° C. ethanol. After pipetting of 1.5 µL of a saturated solution at the reporter area followed by a drying step (20 min, room temperature) the substrate cannot be mobilized by artificial wound fluid 2% albumin. The slightly beige MPO substrate is converted by MPO under development to a deep blue to black color in the reporter area. As the MPO reaction is $H_2O_2$ dependent, a glucose/glucose oxidase based $H_2O_2$ generating system is printed in the reaction area.

Optimized conditions led to the results shown in FIG. 7. Test circles contain 1.5 MPO substrate as described above, 10 µg glucose and 1 µL of 0.1% glucose oxidase (1 µg) in water. After drying of the test circles 5 µL test liquid (artificial wound fluid 2% albumin, pH 7, without/with MPO) were applied. The picture of FIG. 7 was taken after 2 min incubation time.

Elastase substrate: The elastase substrate consists of an Fmoc protected AAPV enzyme recognition motif (amino-acid sequence AAPV) esterified to an Indoxyl moiety. It is soluble in organic solvents, but completely insoluble in aqueous solution. After enzyme cleavage, Indoxyl is released and immediately oxidized to immobile blue Indigo dye (FIG. 8), visible in the reporter area.

Optimized conditions led to the result shown in FIG. 7. In a first step, the test circles were impregnated with a impregnation mixture (0.25% (w/w) Nonidet, 2% (w/w) decanol in 0.05 M borate buffer pH 8). Therefor the two-phase solution was mixed until formation of an opalescent dispersion. This dispersion was transferred in a glass container. The test circles were washed in the impregnation mixture for 1-2 min. Thereafter the filter papers were placed on a glass plate and dried for 1-2 h at 54° C.

In the next step elastase-substrate (10 mg/mL in acetone) was pipetted on the circles 2 times in 2.5 µL steps until a final amount of 50 µg per test circle (20 mm2) was applied (FIG. 7). After drying at room temperature an elastase assay was performed by addition of 10 µL test liquid (artificial wound fluid 2% albumin, pH 7, with/without elastase). Color development was observed and documented after 15 min incubation at room temperature.

The pH indicator is a preparation of bromothymol blue in chitosan, containing glutaraldehyde. The mixture is pipetted in the reporter area, after drying leading to a dark yellow and immobile indicator system. The color changes from slightly green (pH 7) to a dark green (pH 8) within 30 minutes of liquid flow (artificial wound fluid 2% albumin). See FIG. 14 for an example of a pH indicator.

Immobilized bromothymol blue derived pH indicator after running with approximately 300 µL artificial wound fluid 2% albumin with different pH values. pH indicator was applied in amounts of 1.5 µL per 10 mm2 in three pipetting steps of 0.5 µL.

Production and functionality of the reporter area in prototypes. In the reporter areas of the arms of the diagnostic material for Lysozyme detection and the liquid control, 1.5 µL of the trapping mixture were printed. In the reporter areas for Elastase and MPO detection as well as for the pH indicator, the substrates were applied (FIG. 7, 9).

FIG. 9 shows a prototype with the reporter areas for lysozyme, elastase and MPO detection, a pH indicator and the liquid control. On the left the diagnostic material is shown, on the right a magnification of the reporter areas. FIG. 9 (A) shows an example for a prototype with the reporter areas before liquid application.

FIG. 9 displays the diagnostic area after liquid application (negative control, artificial wound fluid 0.5% albumin without enzymes). FIG. 9(C) shows the diagnostic area after liquid application (artificial wound fluid 0.5% albumin, 1 U/mL elastase, 10 µg/mL MPO, 30000 U/mL lysozyme). The experiment was run over 2 h with a flow rate of 100 µL/min for the first 10 min, followed by 10 µL/min. The experiment was repeated in n=10.

FIG. 9 shows a prototype with the reporter areas for lysozyme, elastase and MPO detection, a pH indicator and the liquid control. On the left the diagnostic material is shown, on the right a magnification of the reporter areas. Color signals for the liquid flow control are visible, so it is believed that the method of visualization by trapping and accumulation works. The order of reaction is generally MPO, then elastase, then lysozyme. Color change of the pH indicator as well as the color development of the MPO and elastase substrates is visible in the reporter area. The in-place color change was established for these reactions and functionality was demonstrated.

The inserts can be made in many forms including radial designs (FIG. 10-12), linear designs and single spot approaches. These vary in which layers and patterns are formed. It is generally the goal to make the insert as small and non-occlusive as possible.

One means to reduce occlusiveness is to reduce the area of film layers. In the embodiments shown in FIG. 10-12, the only occlusive layers are the lanes themselves. In this version, the round bottom layer is replaced by only the adhesive. The advantage of the round bottom layer is that tended to support a broader area of the dressing being sampled into the device. The reduced bottom layer has the advantage of permitting more vapor transfer.

Example 4: Lysozyme Responsive Testing Strip

In one embodiment of a means to detect lysozyme activity, a strip of a wicking substance like filter paper is printed with both dyed peptidoglycan (FIG. 15(D), a) and a trap material (quaternary amine fixed with cross-linked PEI) (FIG. 15(D), b). Wound fluid is applied to the base and allowed to wick up the carrier to point C where it evaporates. Lysozyme, if present, degrades the dyed peptidoglycan and transports anionic fragments to the trap (FIG. 15(D), b) where they form a line.

In FIG. 15, one embodiment of a lysozyme test strip (50) comprises a Whatman filter 1001/85 that is cut into 0.5 cm×4 cm pieces having fixation areas (51), evaporation area (52), 3% crosslinked, amino trap (53), substrate area (54), and a stitching area (21) for wicking fluid from a wound. Side view (B) shows a wound dressing comprising a test strip (50), base layer (55), and stitching (21). Top view (C) shows the test strip (50) adhered to wound dressing (56).

Integration of dyed peptidoglycan into a lysozyme responsive testing strip (FIG. 15). In some embodiments, a testing strip comprises a Whatman filter 1001/85 that is cut into 0.5 cm×4 cm pieces. 2 μl of the quaternary amine trapping solution is pipetted onto the cellulose filter 1.5 cm beneath the upper end of the stripe. 2 μl of a substrate formulation containing 4 mg dyed peptidoglycan in 240 μl 0.5% PEG6000 solution in $H_2O$ are pipetted 1 cm above the lower end of the stripe. The modified strip is incubated at 90° C. for 30 minutes. The test strip is then ready to use. Alternatively other dyed lysozyme substrates (e.g. dyed chitosan derivatives) can be incorporated into the testing system. In some embodiments, the testing strip comprises a substrate spot, a quaternary amino trap, and a cellulose matrix.

In some embodiments, integration of the lysozyme responsive testing strip into a dressing for the online detection of early stage wound infections.

Liquid transport system from the bottom side of the dressing to the test strip is performed via a polypropylene yarn stitched through the layers of the dressing and the first water impermeable adhesive layer. While the stitching helps the process, it is not essential and the same results are obtained without stitching, albeit more slowly. The testing strip is embedded in between of two water impermeable adhesive layers. An evaporating area is included in the upper region of the strip. The detection unit releases the coupled dye in region 'a' which is then trapped in area 'b' of the testing stripe and gives a clear visible signal upon lysozyme activity.

Material selection for the test strip: Different cellulose based materials can be used as solid matrix for the test stripe. Non-wovens containing a defined amount of cellulose can alternatively be used. Schematic representation of the Lysozyme test strip. Attachment of the detection system to the dressing (FIG. 15). Base layer contains liquid transfer system to the detection unit. Upper view of the combined base layer and detection unit.

Example 5: Indicator Reactions

FIG. 16 shows examples of indicator reactions include a substrate with at least two domains A and B, or A and C, connected by a cleavage site (X), which is recognized by enzymes in wound fluid, such as elastase (E or E2). In some embodiments, peptidoglycan anchor (S) is attached to an enzyme substrate, requiring digestion or breakdown of the peptidoglycan anchor (S) by lysozyme (El) before the cleavage site (X) on the substrate can be accessed by an enzyme in the wound fluid. Products (P) of the reactions are colored, giving rise to a color change detectable by a user. In example I, upon exposure to elastase (E) in the wound fluid, the substrate is cleaved at cleavage site X, releasing MPO substrate (B), which can react with MPO in the wound fluid and oxidize the substrate (B) to form a colored product (P). In example II, lysozyme (El) breaks down peptidoglycan anchor (S) to expose cleavage site (X). Upon exposure to elastase (E2) in the wound fluid, elastase cleaves the substrate at cleavage site (X) and releases indole (C), which may be converted to indigo in the present of oxygen, giving rise to a color change. In example III, MPO substrate (B) may be used instead of indole (C) to yield a colored product (P).

Example 6: Indicator Disk

FIGS. 10-12 show schematics of indicator inserts or disks. FIG. 10(A) shows the top view of a diagnostic insert, comprising a reporter area (60), reaction area (61), and evaporation area (62). FIG. 10(B) shows the bottom layer, comprising an impermeable layer of plastic film, preferably either white or transparent, with a diameter of about 40 mm. The hole in the middle allows for liquid transport and has a diameter of about 4 mm. The bottom layer is covered with adhesive in the same shape underneath for an exact fixation on a dressing. FIG. 10 shows the reaction material comprising an adhesive layer (C) and a reaction layer (D) wherein each arm may be a different substrate and/or pH system and where the arms in each layer overlap to allow exact fixation. Indicator disks can have any number or indicator arms, such as 4 or 5 arms of indicators arranged radially as in FIG. 10. In some embodiments, the indicator disks comprise 1 to 10 arms, or preferably 4 or 5 arms. FIG. 10(E) shows the cover, which preferably comprises an impermeable white plastic foil with a diameter of 20 mm. The outer ring may have an insider diameter of 25 mm and an outer diameter of 31 mm. The top layer may be covered with adhesive underneath for an exact fixation on the reaction material.

In the embodiment shown in FIG. 11, (A) shows the bottom layer, comprising a double sided and hydrophobic film (65) with a diameter of 40 mm. A hole cut in the middle has a diameter of about 5-6 mm. Reference (66) shows the hydrophobic lanes on non-woven or paper, either full sheet or cut out, placed on the adhesive film. Reference (67) shows traps printed on non-woven or paper which is adhered to the bottom layer with a back-flow trap (68). In (B), the reaction layer comprises arms, each may have a different indicator and color system as shown in (70). An evaporation cover (71) may be printed, sprayed, or overlaid film. Reference

(72) shows the indicator disk affixed to a dressing, wherein outer dressing has a window (shown as dashed line) for viewing the indicator change.

In another embodiment of the indicator disk, as shown in FIG. 12, bottom layer (A) preferably comprises a white or transparent impermeable plastic film (73) of diameter 40 mm. A hole in the middle of bottom layer, comprising a diameter of 4 mm allows for wound fluid transport. The bottom layer may be covered with adhesive in the same shape (73) as the reaction material (77) underneath for an exact fixation on wound dressing, double-sided adhesive and hydrophobic. The reaction layer (77) is placed on top of adhesive layer (73), at the bottom. Each arm of the reaction layer may be 13 mm or 15 mm in length from the center, and about 5 mm wide. Cut access in the center of the disk may also comprise a back-flow trap (75) to ensure fluid flows from the center outward to evaporation area in the periphery of the insert. Reference (74) shows hydrophobic lanes on non-woven or paper, fill sheet or cut out, placed on adhesive. Reference (76) shows traps printed on non-woven or paper with back-flow trap (75) in the middle. In some embodiments, reaction material (77) comprises brilliant black print, pH indicator, MPO substrate, elastase-peptide-indoxyl, and lysozyme-peptidoglycan indicator, and any combination thereof on arms of the indicator disk. Such substrates may be printed on the reaction material or solid support material. Evaporation cover may be printed, sprayed, or overlaid as a film over (78), shown as gray box in (78). The reaction material may be covered by a transparent or translucent film, with a window (79, dash-line box) to allow detection of the reaction.

In some embodiments, a cover as shown in FIG. 10(E), comprises a middle cover of impermeable white plastic film with a diameter of 20 mm, an outer ring with an inside diameter of 25 mm and an outer diameter of 31 mm, and a top layer covered with adhesive in the same shape underneath for an exact fixation on the reaction material.

As shown in FIG. 10(A), one embodiment comprises an impermeable white plastic foil with an outer diameter of 31 mm, inner diagnostic circle (60, reporter area) with diameter of 25 mm, and the substrate cover (61) with diameter of 20 mm in embodiments using a substrate cover. Evaporation area (62) is located at the periphery of the indictor insert. A small evaporation area, such as 2×5 mm may be too small for a 7-day run, but is sufficient for a smaller run, such as a one-day run. Visible signal resulting from reactions can be detected in diagnostic area (60) or window reporter area (FIG. 11 or FIG. 12). Such reporter areas can be surrounded by an off-white layer to achieve maximum contrast to color signals.

In another embodiment, the diagnostic reaction can be performed on a solid phase in which liquid sample diffuses in the vicinity of dyes that are absorbed onto the solid phase. Enzymes carried in the sample can transform the dyes through contact in the pores of the solid phase material. The changes are visible as color changes. Due to the low volumes in use and the high concentration of dye, the color change can be a sensitive indicator.

In a preferred embodiment indicator disks are prepared by impregnating a filter paper with the reagents and then punching disks prior to adhering them to a carrier to form a "stick" with a reactive dye coated on it. This stick can be brought into contact with the sample and a color change observed.

In a more preferred embodiment, more than one indicator disk type is placed onto the stick carrier such that multiple enzymes or parameters can be detected in one test. Parameters that may be determined include pH, lysozyme, elastase, Cathepsin G, MPO, catalase and lipases. Such a stick should also contain a positive control to indicate adequate sample wetting, and or sample application including, in addition to wetting, also the presence of protein.

In one preferred embodiment the indicator disks are aligned in a line on a thin "stick" and the sample is applied to them in sequence using a swab, gauze, or by pressing the stick into or onto a sample, for example a used dressing.

In another embodiment, the indicator disks are aligned next to each other on a broad support and their edges on one side are cut such that the stick can be pressed with the cut edge to the sample source (i.e. a used dressing or diluted wound fluid, or the edge of a cleaning swab or gauze) such that liquid is taken up into each of the disks at the front of the broad stick ("Fork" format).

In another preferred embodiment the indicator disks are placed inside a carrier box such that the sample swab can be inserted into the box and then sealed inside by closing the box. After closure, the sample swab can be moved and in the process, contacts each sample disk in turn to wet them appropriately such that the resulting reaction can be observed through windows appropriately placed above each indicator disk. Such an arrangement can preserve the swab for later microbiological examination and simplify the handling of materials at or during a dressing change.

Indicator disks are preferably prepared with reagents that are capable of color change. Such reagents may be selected from compounds such as p-aminophenol, ABTS (2,2inophenol, ABTS (strate. In some embodiments, acid) diammonium salt), 3,3'-diaminobenzidine, 3,4 diaminobenzoic acid, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, 4-chloro-7-nitrobenzofurazan. In some embodiments, the reactive layer comprises an arylamine. In some embodiments, the reactive layer comprises an amino phenol. In some embodiments, the reactive layer comprises an amino phenol an aminophenol ether. In some embodiments, the reactive layer comprises an indoxyl. In some embodiments, the reactive layer comprises an a neutral dye. In some embodiments, the reactive layer comprises a charged dye, e.g., a dye selected from remazole brilliant blue, toluidine blue, reactive black 5, remazol brilliant blue, reactive violet 5, and reactive orange 16, or a hydrolytic or ammonolytic derivatives thereof, toluidine blue, reactive black 5, or ahydrolytic or ammonolytic derivatives thereof, reactive violet 5, or hydrolytic or ammonolytic derivatives thereof; reactive orange 16, or hydrolytic or ammonolytic derivatives thereof; a dichlorotriazine-based reactive dye such as reactive blue 4, reactive red 120, reactive blue 2, reactive green 19 and reactive brown 10. In some embodiments, the dichlorotriazine-based reactive dye appears black. In particular embodiments, the reactive layer comprises compounds such as a reactive dye containing a sulfonylethylhydrogensulphate-reactive-group. In some embodiments, the reactive dye is reactive black 5, remazol brilliant blue, reactive violet 5 or reactive orange 16, particularly reactive black 5. In some embodiments, the reactive dye is remazol brilliant blue, reactive violet 5, reactive orange 16, reactive black 5, or remazol brilliant blue. Especially, the reactive layer comprises a dye containing a sulfonylethyl-hydrogensulphate-reactive-group, e.g., reactive black 5, remazol brilliant blue, reactive violet 5 or reactive orange 16, or a combination thereof; or a dye containing a dichlortriazine reactive-group, e.g., reactive blue 4, reactive red 120, reactive blue 2, reactive green 19 and reactive brown 10, or a combination thereof.

In other embodiments, indicator disks are preferably prepared with reagents that are capable of physical change, e.g., nanoparticle, colloidal gold particle or a luminol derivative.

In a preferred embodiment, MPO is detected using an analog of Fast Blue, or a di-amino phenol as a color generating agent; Elastase is detected using a peptide derived indicator including a napthol phenol, indoxyl or a nitro-phenol; Lysozyme is detected using an oligo saccharide conjugated to a dye or color generator, or an oligosaccharide particle containing a charged dye in particular said oligosaccharide may be selected from peptidoglycan or chitosan derivatives. Purely as a representative example, lysozyme may be detected by visualizing reactive black 5, remazol brilliant blue, reactive violet 5 or reactive orange 16, reactive blue 4, reactive red 120, reactive blue 2, reactive green 19 and reactive brown 10, or a combination thereof bonded to a substrate such as chitosan, N-acetyl chitosan; oligo-β-D-1,4-glucosamine; acetyl-D-glucopyranoside; N-acetylglucosamine (GlcNAc); glucosamine dimer $(GlcNAc)_2$; acetyl-chitosan; chitobiose octaacetate; a chitooligomer comprising the structure (GlcNAc), wherein n=4, 5, or 6; a chitooligosaccharide; 2-acetamido-2-deoxy-D-glucopyranoside; 2-deoxy-3,4,6-tri-O-acetyl-D-glucopyranoside; or a combination thereof. Protease such as human neutrophil elastase or HNE) may be detected by using a peptide substrate comprising a core sequence Alanine-Alanine-Proline-Valine (AAPV) which is conjugated to one or more of the aforementioned dyes.

In another embodiment, the reagents to detect these analytes are subject to cleavage to yield a compound that is trapped on an immobile portion.

Example 7. Use of an Indicator Dressing in the Context of a Wound Therapy

A dressing containing an indicator disk as described above is prepared in which the printed disks are inserted between the absorbative outer layer of the dressing and the outer membrane or film such that the reacted areas are visible. The dressing is applied to a wound, be it chronic or surgical, such that sites of secretion in the wound (deeper sites, sutures) are located under or as near as possible to centers of the disks. See FIG. 17. Following dressing application, the dressing will begin to absorb secretions. In one embodiment, the first observation of wound status can be made after the "flow control" has turned blue. This is an indicator of the fact that sufficient liquid has entered the dressing to saturate the reagent pads. If, at this stage one or more of the biomarker indicators has already reacted, this would be an indicator of the fact that a degree of inflammation or potential infection was present in the wound at dressing change. One biomarker reacting, with or without an indication of pH above neutral, is likely sufficient to justify detailed wound hygiene steps at the next change. Two biomarkers responding with or without a pH above neutral is likely an indication that in an ideal situation, the wound would be immediately re-dressed and anti-microbial approaches initiated. Three biomarkers responding, with or without pH would likely be an indicator that in an ideal situation the dressing should be immediately changed and anti-microbial hygiene, wound dressings and laboratory microbiology should be initiated.

In a broad sense the indicators can respond immediately after dressing change, after 1-2 days and after 2-5 days. Due to the dynamics of flow, the reagents are intended to respond within 2-6 h of exposure to a threshold of enzyme activity, for example 0.5 U/mL elastase, however, long exposure to low enzyme levels, i.e. 5 days, may also ultimately engender a signal. Thus, the user can distinguish a low level of activity from an acute sign in that the reporter area very slowly accumulates signal, i.e. very faint at 3 or 4 days and only slightly more developed after 4 or 5 days. This would be indicative of a wound deserving of close observation and hygiene but not necessarily one in acute infection. Experience with the particular patient would also inform the therapist. If the same pattern was apparent over multiple dressing changes it would suggest a stable situation but that any change in the degree of reaction should be taken as an indication of a potential change in wound status.

In contrast, a situation in which a strong signal suddenly appears is potentially indicative of the onset of an acute infection. Given that the indicator can change within 1-2 hours once a threshold is crossed suggests that any sudden developments reflect the current situation of the wound.

Where multiple infection indicator disks are placed within the wound dressing, the position of those that react is an indicator of where in the wound potential problems arise. Thus, the absence of clear signals after 5 days would be an indication that no thresholds have been crossed in that period and that current therapy may be adequate. Weak signals that develop slowly may indicate that hygiene could be improved. Moderate signals that appear gradually after 5 days may be the first signs that an infection is developing and should result in more elaborate therapy. Strong signals that develop over 5 days would be correspondingly more emphatic indications that therapy need be improved, for example, by instituting silver dressings. The rapid onset of a clear signal is, in turn, the indicator of an acute issue that merits immediate attention.

As shown in FIG. 4(C), multiple reaction cells can be applied to a wound dressing in some embodiments for detection of microbial infection over an area. Amine back flow trap or filter or leach-back trap (41) may be used to separate testing regions.

Example 8. Dressing Inserts that May be Applied to any Dressing

In some embodiments, indicator insert may be freely placed at a site of likely secretion or placed anywhere in a wound dressing or a surgical dressing.

Diagnostic disks, as described above, can be incorporated into a dressing during its manufacture. These inserts may be placed between the outer absorbent and the outer film and equally spaced, and glued in place during manufacture. However, the fixed spacing may not be appropriate to a particular wound. In this example, the reporter disks are prepared as independent materials that can be put on any absorbent dressing below the outer film. For example, the inserts are prepared as stand-alone disks, cut and sealed in sterile outer envelope. Therapists using dressings, see reference (92) in FIG. 17, without reporters may still insert these reporters (90) into such dressings in so far as these are modular and require the therapist to assemble the dressing from: wound contact material, absorbent, and outer film or cover. The reporter disk can fulfill its function in many ways, including so long as it is in fluid contact with the wound fluids (91) and otherwise under an appropriate outer dressing. An adhesive transparent outer disk is one means of fixing and holding the reporter disk. Similarly, the disk itself may have an adhesive bottom coat.

In another embodiment of diagnostic inserts, shown in FIG. 18, non-woven layer in a dressing carries or contains diagnostic disks (705), wherein the dressing further comprises a film cover layer (701), non-woven carrier of indicators (702), polyurethane foam (703), and cellulose contact layer (704). As demonstrated by the arrow in FIG. 18(A), wound fluid flows upward to diagnostic disks (705) embedded in such dressing. FIG. 18(8) shows a side view of the wound dressing with embedded diagnostic disks, wherein quaternary amine coating (shown as dashed line) on foam surface acts as trap for preventing return of diagnostic substances and that wound fluid flows upward to diagnostic disks.

In a further embodiment of diagnostic disks in wound dressing, as shown in FIG. 19(A), the side view representation (A) shows an example disk for detecting MPO, wherein (720) is a paper disk impregnated with the MPO substrate through dipping or spray coating. Reference (721) is the paper or non-woven material that acts as a carrier. Reference (722) shows an adhesive layer. Reference (723) represents a disk containing glucose oxidase and/or starch and an amylase, such as gamma amylase. FIG. 19(D) shows the wound fluid mobilizes starch into glucose, which in turn is oxidized by glucose oxidase to yield $H_2O_2$. This is used by MPO in the wound fluid to convert the substrate to the detectable blue form. FIG. 19(8) shows the side view of a disk for detecting lysozyme, wherein particles of chitosan or peptidoglycan are embedded in the paper disk on its lower side using a water permeable adhesive layer that also serves to adhere the disk to the foam layer below. Enzyme activity dissolves the particles and releases dye that is trapped and is detectable in the top layer. In FIG. 19(8), the paper disk (730) is a trap impregnated top layer. In the presence of wound fluid, as shown by the upward arrow in FIG. 19(C), the paper/non-woven disk acts as a carrier (721) so that the wound fluid moves to the top layer, via stained peptidoglycan particles (731) in the process. Reference (722) shows an adhesive layer. Reference (732) shows an adhesive ring or thermal weld that secures the disk to the non-woven carrier layer (721). The dashed line in FIG. 19(C) represents quaternary amine coating on foam surface under the diagnostic strips that acts as a trap for preventing return of diagnostic substances. FIG. 19(E) shows stained peptidoglycan particles slowly being dissolved by wound fluid and the dye that is released is then captured in the trap material while excess wound fluid flows to the sides, as indicated by the arrows. In FIG. 19(E), the paper disk is impregnated with trap material in the top layer.

In FIG. 20, the scaling up of the production of the disk constructs is described. In the continuous process, the disks are punched from a sheet comprised of sealing film, the adhesive, the paper or non-woven carrier, which is protected by the top cover sheet.

FIG. 21 shows different embodiments of paper disks. FIG. 21(A) shows the different layers involved in such embodiments, namely, film cover on top, a non-woven carrier, a polyurethane foam, and a cellulose contact layer. FIGS. 21(8) to 21(E) show different variants of such analytic system with indicator disks. FIG. 21(8) shows nonwoven carrier of indicators with diagnostic disks attached, including pH indicator on paper, paper disk printed with starch, amylase, and glucose oxidase, and trap impregnated paper disks. FIG. 21(C) shows partly printed non-woven and applied paper disks, including trap printed and UV border or trap border (910). FIG. 21(D) shows partly printed nonwoven and gradient (911) application of indicator disks. The gradient is formed by printing concentric rings of substrate at different concentration, or with a different pH mediator. Fully transformed, different substrate concentrations lead to different color intensity. Alternatively, using polymeric buffers in each ring can modulate the degree of reaction requiring more activity to yield the same color. Suitable buffers include polycarbonates and polysulfonates. The number of concentric rings of color provides an indication of overall activity and thus with reference to a color chart can assist in assessing the degree of severity. FIG. 21(E) shows one embodiment of the diagnostic disks with printed indicators (912) and reagents applied on adhered paper disks. In these embodiments, the non-woven functions as a carrier of indicators.

FIG. 22 shows different ways diagnostic disks (800) may be attached to a dressing. For example, FIG. 22(A) shows continuous adhesive that allows wound fluid to penetrate through the adhesive. FIG. 22(8) shows ring or annular adhesive that allows wound fluid to penetrate via the hole in the middle of the adhesive layer. FIG. 22(C) shows welding with UV printed border. FIG. 22(D) shows welding with polyethylene component of non-woven.

Example 9: Dipstick-Traffic Light Format

Certain reagents have adequate affinity for paper or similar solid phases and remain substrates for the biomarker enzymes of interest. Where these substrates exhibit color change, the activity of the enzymes can be observed by simply contacting the fluid containing the markers with the impregnated paper. Capillarity ensures the distribution of the fluid to the substrate. Each impregnated disk can be separately added to a combined "dipstick" which allows all disks to be used in a test (FIG. 23). One format is the linear array of disks, although the layout may be easily varied.

FIG. 23 shows indicator inserts or disks (820) specific for various enzymes or microbial biomarkers and controls may be placed in various combinations or arrangements to form various dipstick devices. Each impregnated disk (820) can be separately added to a combined dipstick that allows all indicator disks to be used in a test. One format is the linear array of disks, although the layout may be easily varied. Indicator disks may be separated by lanes or borders (821).

In this example, the following disks are prepared:

1. Fluid control: a 5 mm disk of double sided adhesive is punched, and 50 µg of a micronized Fast green powder is placed on the adhesive in the center. A paper disk is placed over the adhesive disk concentrically, such that the powdered dye is covered by the paper. The resulting disk is then placed in the first position on the carrier stick via the other side of the adhesive.

2. pH control. Filter paper is soaked in a mixture containing bromothymol blue, chitosan and glutaraldehyde in ethanol as reported above. The filter paper is dipped in the mixture, allowed to drip dry, and is then dried on glass at 54° C. 5 mm disks are then punched and the disks are attached to the carrier with adhesive.

3. MPO indicator. 5 mm paper disks are impregnated sequentially with 1.5 µL of the MPO fast blue substrate as described above for the Dressing indicator. Once dried, one half of the disk is impregnated with 10 µg of glucose and the other half of the disk is impregnated with 1 µg of glucose oxidase in buffer (PBS).

4. Elastase indicator. Filter paper was impregnated with a mixture (0.25% (w/w) Nonidet, 2% (w/w) decanol in 0.05 M borate buffer pH 8) and dried for 1-2 h at 54° C. 5 mm paper disks are punched from the buffer treated paper and impregnated sequentially with 2 times 2.5 μL of the AAPV indoxyl substrate (10 μg/μL in acetone) as described above for the Dressing indicator.

5. Lysozyme indicator. Filter paper is lightly sprayed (1.5 μL per cm2) with a trap solution containing 3% W/V quaternary amine trap and allowed to dry with the top surface identified. A 5 mm disk of double sided adhesive is punched, and 40 μg of a Brilliant Black stained Peptidoglycan is placed on the adhesive in the center and allowed to dry. A paper disk is placed over the adhesive disk concentrically, such that the PG-dye deposit is covered by the paper. The resulting disk is then placed in the fifth position on the carrier stick via the other side of the adhesive. The resulting dipstick can have the sample applied to it by means of swab, or gauze.

Example 10: Dipstick-"Fork" Format

In one embodiment a dipstick is prepared essentially as for the above example with the exception that the reagent disks are oriented to the base of a thicker carrying card or stick. The ends of the reagent disks are trimmed at the last stage of production such that they are flush with the bottom edge of the device. This allows them to be pressed onto a surface to be sampled. The sample then diffuses into the cut end of the disks to react. This format is potentially more convenient for sampling surfaces like used dressings.

Example 11: Dipstick-Box Format

In certain instances, suspected infection, or the risk of contamination between patients through consumables and their disposal demands a more secure system. In one embodiment, where sampling is done via a swab, retention of the swab for subsequent bacteriological evaluation may be desirable. Similarly, it may be desirable to retain the result and display it to a colleague after a dressing change. In this context, a means to retain the result without risk of contamination is desirable. To this end, in one embodiment, a sealable container or enclosure may be used for accommodating a plurality of disks, such as 6 disks, in which a wet swab can be placed and then closed such that it can apply the sample to the paper disks but not contaminate any further objects. One such design is illustrated along with its working principle (FIG. 23). The key elements of the design are: the well for wetting the swab; its closed sealable form; the sealing rings around the stem of the swab; the pressure fins that push the swab to the disks while also making it a one-way movement; the window to the disks; the space for reference colors on the case, the possibility to re-open in a microbiology lab.

Example 12: Surgical Site Detection

In another embodiment, the dressing is intended for the treatment of surgical wounds and contains distinct linear regions intended to be placed over the line of sutures. These linear regions contain particularly high concentrations of reporter dye such that even in the earliest phases of infection, the signal will be apparent. In another embodiment, the dressing contains a removable components such as a thread, or similar absorbent that can be withdrawn and tested without removing the dressing (FIG. 24). Said removable component is placed in such a way as to be located at or near the edges of the surgical wound. In another embodiment, the surgical site dressing is essentially transparent in the linear region both to allow observation of the sutures, and the reporter dye. In a preferred embodiment, the transparent area is covered by an opaque film that may be easily peeled back to examine the wound. In another embodiment the covering and absorbent material contains a trapping material such as a polymeric cation or anion that is capable of binding and concentrating the dyes that are released.

For example, in FIG. 24, sampling threads (100) are built in or added to dressing for a wound or at a surgical site (92). AQUACEL (4) is used in some embodiments of the dressing (92). Sampling threads absorb wound fluid or fluid at surgical site (D). A thread may be pulled out or extracted (E) from dressing without having to remove or disturb dressing using an instrument or device (101) such as a tweezer, hook, or thread hook device. The thread can then be dissolved in a buffer for use in a diagnostic device (102) using one or more indicator regents or indicator disks described herein.

In some embodiments, a wound dressing comprises built in sampling threads. In some embodiments, the sampling threads absorb wound fluids and may be removed without disturbing the wound dressing for detection of analytes in the wound fluid.

In some embodiments, the sample threads may be diluted in buffer to dissolve markers for diagnosing the status of the surgical site or wound.

In some embodiments, a thread hook device may be used to remove a thread from a wound dressing.

Example 13: Manufacture of Dressing Inserts

The reporter inserts are manufactured by the sequential placement of various materials on a solid carrier. This carrier can be a cellulose, viscose, polyethylene, poly-amide or other suitable polymer or mixture of these components.

FIG. 25 shows indicator inserts may be manufactured or printed in sheets or reels. FIG. 25 also shows the order of printing, printing of lanes, order on which reagents are laid down, and placement of reagents for printing disks in sheets or reels, comprising adhesive or backing film as in FIG. 25(A), applying a non-woven material as in FIG. 25(B), and printing reagents and lanes on non-woven material as in FIG. 25(C). Completed or assembled inserts, as show in FIG. 25(D) can be separated or cut before sticking to a dressing or similar support materials.

In one embodiment the material is prepared in a reel to reel format. The solid carrier is first printed with guide lanes that penetrate the film to full thickness. Next, a bottom film that sits under the polymer and does not penetrate it is printed, this includes a hole in the center through which sample fluid enters. Next trap material is printed, at half density around the entrance site (back-flow trap) and at full density in the trapping sites for the flow control and the lysozyme substrate. Next the flow control ink is applied to the first position of the radial arms of the disk, 10 to 50 μg of Brilliant black in 1% methylcellulose is typical. Next the pH reporter, as described above is printed in position 2. Next, the MPO area is printed sequentially with substrate, glucose and glucose oxidase as noted above. Next the elastase substrate is applied in sequential prints to reach the appropriate load. Next the lysozyme substrate is printed to position 5 in the reagent level (as distinct from the trap level). Finally a film is printed on the top of the construct but without penetration of the solid carrier. This film occludes only the radial arms from center to the end of the reporter window.

The resulting reel contains a continuous pattern of evenly spaced reporter fields. These continuous printed fields can be directly rolled into a dressing sandwich between absorbent and outer film, or, they may be punch cut and packaged for separate use.

FIG. 20 shows another embodiment of manufacturing paper disks. FIG. 20(A) shows a side view of a continuous sheet, comprising a cover film on top, paper in the middle, and backing film at the bottom. Adhesive/particle matrix (901) may be applied between the cover film/backing film and the paper layer (900). FIG. 20(B) shows a top view of cut sheets prepared for application to non-woven carrier by removal of inter disk material prior to placement on non-woven carrier.

Example 14: Manufacture of Reagents for Liquid Based Devices

In certain embodiments, it is desirable to place reagents in devices in such a way as that they are stable, but readily soluble for access to injected enzymes. One approach is to dry reagents on disks of paper and include the disks in the devices.

Disks are prepared using either a continuous paper or similar material or textile which is dipped, sprayed or printed, or using pre-cut disks that are dipped or mixed in a reagent and subsequently dried. See FIGS. 20, 25.

The densities of the reagents per 20 mm2 are:
MPO substrate (alkyl-fast blue) 0.6 µg
Glucose 10 µg, glucose oxidase 1 µg For elastase, paper is first impregnated with impregnation mixture (0.25% (w/w) Nonidet, 2% (w/w) decanol in 0.05 M borate buffer pH 8).

Thereafter the paper is sprayed with a solution of elastase substrate corresponding to 2.5 µg per mm2.

The paper so printed can be punched to yield disks containing the reagents.

These disks can then be incorporated into the devices.

Example 15: Manufacture of Reagents for Liquid Based Devices

Alternatively, the reagents may be pressed into water soluble "pellets" which are then included in the wells of the devices. The pellets can contain a range of materials in addition to those used on paper.

A liquid based diagnostic device uses pre-formulated reagents to generate a colour in response to enzyme activity in a sample. The sample may contain all or only some of the liquid required. Where the sample is to be diluted, the device preferably contains water or buffer suitable to dilute or render the sample homogeneous. The resulting mixture is distributed to wells which each contain a different reagent set. The reagents are a mixture of buffer salts, energy source, substrate and associated chromophores if not contained in the substrate. These reagents are ideally delivered in a discreet entity like a tablet or similar that can be placed in the wells. Here we describe the preparation of tablets for enzymatic assays for elastase, lysozyme, MPO and protein standard as internal standard. The tablets dissolve after addition of wound fluid and release assay components to start the enzyme reactions that lead to colour changes where positive.

A Perkin Elmer electro-hydraulic tablet press is used to form the tablets as follows:
The pressing time per tablet is approximately 10 sec.
The diameter of the filled part of the pressing tool is 5 mm
Tablets are: 20 mg, 5 mm diameter, 1 mm deep
A vacuum is first applied for about 15 sec.

The applied vacuum is maintained until the removal of the pressing tools.
The pressing pressure is adjusted to 2 t.

TABLE 1

List of tablet reagents for use in liquid-based diagnostic devices.

| Component | Amount in 20 mg (mg) |
|---|---|
| MPO Tablet | |
| $Na_2CO_3$ | 0.38 |
| $NaHCO_3$ | 0.54 |
| Guajacol $(CH_3O)C_6H_4OH$ = Substrate Alternatively diaminophenol | 1.53 |
| Sodium percarbonat × 1.5 $H_2O_2$ $(Na_2CO_3 \cdot 1.5H_2O_2)$ | 0.02 |
| Maltose Monohydrate $(C_{12}H_{22}O_{11} \cdot H_2O)$ | 17.53 |
| Elastase Tablet | |
| Sodium Acetate $(C_2H_3NaO_2)$ | 1.64 |
| Sodium chloride (NaCl) | 5.84 |
| N-Methoxysuccinyl-Ala-Ala-Pro-Val-p-nitroanilide $(C_{27}H_{38}N_6O_9)$ = Substrate | 0.24 |
| Maltose Monohydrate $(C_{12}H_{22}O_{11} \cdot H_2O)$ | 12.28 |
| Lysozyme Tablet | |
| Potassium hydrogenphosphate $(K_2HPO_4)$ | 7.32 |
| Potassium dihydrogenphosphate $(KH_2PO_4)$ | 1.09 |
| Peptidogycan (von *Micrococcus lysodeicticus*) as a film or dyed with reactive black as gross particles = Substrate | 0.20 |
| Maltose Monohydrate $(C_{12}H_{22}O_{11} \cdot H_2O)$ (Filler) | 11.39 |
| Internal Standard Tablet | |
| Citric acid $(HCO(COOH)(CH_2COOH)_2$ | 8.56 |
| Sodium hydrogenphosphat $(Na_2HPO_4)$ | 1.54 |
| Bromophenol blue $(C_{19}H_{10}Br_4O_5S$ | 0.06 |
| Maltose Monohydrate $(C_{12}H_{22}O_{11} \cdot H_2O)$ | 9.84 |

Example 16: Standalone Device and Kit for Liquid Based Assay

Stand-alone devices and kit for detecting and measuring wound infection using the compositions and device are described herein. These devices and kits preferably comprise a sampling component for collecting a sample and a test device. In some embodiments, the test device comprises a housing surrounding a tube to define an opening in the housing to receive the sampling component, the housing having within it a sealed diluent chamber which is connected to an opposite end of the tube and holding a liquid diluent for removing the sample from the sampling tip to form a test liquid. The tube is in liquid communication with a reaction well which holds a reagent capable of indicating the presence of the analyte. A driving mechanism drives the diluent from the chamber past the sampling tip, into the tube and finally to the reaction well.

In some embodiments, the kit for detecting an analyte in a sample comprises: (i) a sampling component comprising a sampling tip for collecting the sample and (ii) a test device, further comprising: a housing surrounding a tube to define an opening in the housing to receive the sampling component, the housing also having disposed within it: a sealed diluent chamber connected to the tube and holding a liquid diluent for removing the sample from the sampling tip to form a test liquid; a reaction well in liquid communication with the tube, the reaction well holding a reagent capable of indicating the presence of the analyte within the test liquid; and a driving mechanism capable of driving the diluent through the device from the chamber, over the sample tip and into the reaction well.

The kit operates by driving the diluent over the sample and into a reaction well, a test solution is made by the flow of the diluent over the sample. It is not necessary to first mix the sample with the diluent to make a test solution and then move that solution via a lateral flow strip to the reaction well. The driving of the diluent past the sample and to the reaction well means that the kit can be used with a minimum number of steps, for instance taking the sample, inserting the sampling component into the housing and activating the driving mechanism. This simple procedure minimizes user error and thus minimizes false negative results and misdiagnoses.

The sealed diluent chamber may contain a specified volume of diluent so that an expected volume of test solution reaches the reaction well or wells. In addition the pathway between the diluent chamber and the reaction well is vented so that trapped air does not affect the flow of test solution through the device or prevent the test solution from reaching the reaction well.

The housing preferably has two parts which are capable of moving with respect to each other while remaining connected to one another. The action of moving the parts may provide the driving mechanism by which diluent is moved through the device. The diluent can be driven through the device by compression of the diluent chamber which forces the diluent past the sample tip and to the reaction well or wells. The compression of the diluent chamber can occur when the parts of the housing are moved with respect to one another such as by sliding one part past another.

In some embodiments, the housing comprises a locking mechanism which locks the housing in position once the driving mechanism has been activated and prevents reuse of the device. In this way it is immediately apparent that the device has been used and cannot be used again. This minimizes false results from, for instance, a device that has been mistakenly activated in transit or from reuse of a device whose reagents have been spent.

In some embodiments, the sampling component preferably comprises a handle and a sampling tip, the handle preferably comprising a seal which engages with the opening in the housing to seal the tube when the sampling component is fully inserted in the tube. The seal generally prevents escape of the sample and diluent from the device reducing the chance of cross contamination from the wound fluid. Preferably the seal and tube engage to lock the sampling component in the device and prevent removal of the sampling component once it has been used. This further reduces the chance of cross contamination from the sampling component.

Preferably insertion of the sampling component in the device releases the seal on the diluent chamber. Preferably the seal is a ball valve or can be a film or membrane seal or a duck bill valve or other non-return valve known in the art which is activated when the sampling component is inserted in the device. The sampling component preferably bursts, punctures or displaces the seal on the diluent chamber when it is inserted in the device.

Preferably the tube is the same or similar size to the sampling tip of the sampling component so that the act of inserting the sampling tip into the tube causes it to be scraped along the walls of the tube aiding the dispersion of the sample in the diluent once it is released from the diluent chamber and is flushed through the device. The sizing of the sampling tip to match the tube also forces the diluent to be flushed through the tip when the diluent is driven from the diluent chamber. Preferably the diluent chamber is shaped like a bellows to assist in the compression of the chamber. Alternatively the chamber can be a combination of a plunger and tube similar to that found in a syringe or can be a filled flexible sachet which is compressed by hand by the user or a balloon which contracts when the seal is released.

In some embodiments, the kit comprises a sampling component for collecting a sample and a test device. The test device comprises a housing surrounding a tube to define an opening the housing to receive the sampling component, the housing having within it a sealed diluent chamber which is connected to an opposite end of the tube and holding a liquid diluent for removing the sample from the sampling tip to form a test liquid. The tube is in liquid communication with a reaction well which holds a reagent capable of indicating the presence of an analyte.

A driving mechanism drives the diluent from the chamber past the sampling tip, into the tube and finally to the reaction well.

FIG. 26 shows a cross section of a standalone device kit for detecting an analyte in a sample. The sampling component (2) comprises a handle (4) and a sampling tip (6) in the process of being inserted into the housing through one end of a tube (10). The sampling component (2) has a sealing means (12) which forms a seal with the open end of the tube (10) while the sampling tip (6) depresses the ball valve (14) to open the diluent chamber (16). FIG. 27 shows a sampling tip fully inserted in the housing to seal the component to the device. FIG. 28 shows a plan view of the standalone device kit with the sampling component in place and shows three viewing windows (20) to the left of the housing which coincide with three reaction chambers (18) which contain a reagent capable of indicating the presence of an analyte. The reaction chambers may contain reagents capable of detecting different analytes from for instance a wound fluid. The window on the right of the housing when viewed from above is a control window which indicates that the test has taken place. Housing (8) is in two main parts which are slidably connected to each other. In FIG. 29, a user of the device can slide a lower part of the housing (24) away from the upper part of the housing (26) and in so doing cause a lever (28) to compress the diluent chamber (16) and drive the diluent out of the chamber, through the sampling tip (6) and up tube (10) to manifold (30). A plan view (FIG. 30) of the standalone device kit with housing slid apart, which results in windows (20) and control window (22) indicating that a test has taken place. The arrows (A) in FIG. 29 indicate the movement of the diluent through the device to form a test solution. Diluent chamber, tube and reaction chamber in the standalone device kit are shown in FIG. 31, with the housing removed for clarity. FIG. 32 shows distribution of test solution to each reaction chamber in a standalone device kit. Test solution flows to each reaction chamber (18) from a central node (32). The node (32) may also contain a non-return valve to prevent test solution from flowing back into the device and causing cross contamination.

The sampling component comprises a handle and a sampling tip in the process of being inserted into the housing through one end of a tube. The sampling component has a sealing means which forms a seal with the open end of the tube while the sampling tip depresses the ball valve to open the diluent chamber. The sampling tip, when fully inserted in the housing to seal the component to the device, allows the housing to be opened, releasing the diluent and allowing the forcing means to operate.

The device also comprises three viewing windows in the housing that correspond to three reaction chambers which contain a reagent capable of indicating the presence of an analyte. The reaction chambers may contain reagents capable of detecting different analytes from for instance a wound fluid. Some embodiments include a control window which indicates that the test has taken place and that the sample was sufficient to make the test viable.

The user of the device can slide a lower part of the housing away from the upper part of the housing and, in so doing, cause a lever to compress the diluent chamber and drive the diluent out of the chamber, through the sampling tip and up tube to manifold. If the device is not activated, that is if the seal on the diluent chamber has not been broken, it is not possible for the housing to open. The opening of the housing causes the viewing windows to be positioned over the reaction wells and enable the result to be viewed by the user. This provides a safety measure as it ensures that proper operation of the device in order to obtain a reliable result.

Once activated, the test solution flows to each reaction chamber from a central node. In some embodiments, the node comprises a non-return valve and filter to prevent test solution from flowing back into the device and between reaction chambers, which can cause cross contamination. The pathway for the flow of diluent through the device is preferably provided with vents at the reaction chamber end.

Example 17. Devices with Separate Sample Preparation Chamber

FIG. 33 shows a diagnostic swab device with housing. In one embodiment the swab device comprises a resealable housing (80), further comprising locator and locking pins (82), a viewing window (81) for observing visible signals from reagent disks placed in disk holders (83), and a groove (85) for placing the swab. Side view of FIG. 33(C) shows the housing (80). To use, a user touches a sample with the swab, places the swab in the housing (80) in groove (85), pull on the stem of the swab as shown by the arrow in (D) so that the sample on the swab slides on the strip (86) and transfers the sample to reagent or indicator disks (83). The results may be viewed through viewing window (81). The swab may also be kept in the housing (80) for analysis later.

FIG. 34 shows one embodiment of a thread hook sample preparation device (200), comprising a needle-like tip and a handle or plunger (201), wherein the tip further comprises a hook for extracting a thread from a dressing without disturbing the dressing as shown in FIG. 34(A). Upon extracting a thread from the dressing, thread hook device (200) may be inserted into a sample preparation chamber or diluent chamber (202) containing a diluent for dissolving or diluting microbial biomarkers or wound fluid from the thread FIGS. 34(B) and 34(C). The plunger (201) of the thread hook device may be depressed downward in the sample preparation chamber (202) so that the tip of the needle breaks a seal as shown in FIG. 34(D) at the bottom of the sample preparation chamber (203) in order to release the sample solution into a device for analysis of wound fluid or surgical site.

FIG. 35 shows one embodiment of a swab sample preparation device (300), comprising a swab (302) with a handle or plunger (301) may be used to touch a sample for testing. The swab device (300), after sampling a bodily fluid or wound fluid, is placed inside a sample preparation chamber (202) containing a buffer for dissolving or diluting the wound fluid or bodily fluid as seen in FIG. 35(A). The swab device is agitated or mixed inside the sample preparation chamber to further release the fluid sample into the sample preparation chamber as shown in FIG. 35(B). The plunger (301) of the needle is depressed downward as shown in FIG. 35(C) to break the seal (203) at the bottom of the sample preparation chamber, allowing the sample fluid to flow into a reaction chamber containing reagents or indicator inserts or disks for detecting microbial infection in the sample taken by the swab. In some embodiments as shown in FIG. 35(D), gas is removed using Goretex membranes (204) which are gas and vapor permeable, but not permeable to liquid water. Said membranes can be used to degas both the sample as it is injected and to vent the fluid chambers where the assay takes place.

FIG. 36 shows a sample preparation chamber adapted to indicator testing. Sample preparation chamber (202) is adapted for dissolving or diluting a sample for testing further and comprises a resealable top (401) and a breakable seal (402) at the bottom of the chamber (203), where the sample preparation chamber connects to a reaction chamber or diagnostic device. When a swab device or a thread hook device is plunged downward or depressed downward in the chamber, it causes the seal (402) at the bottom to break, releasing sample fluid into a diagnostic device connected to the chamber.

In a further embodiment, FIG. 37, a diagnostic device (500) or analysis system is adapted to connecting to the sample preparation chamber (202) at one end, allowing sample fluid to flow from the sample tip (300) upon breaking the seal (203) at the chamber connector, which allows the sample fluid to flow from the sample preparation chamber (202) into reaction chambers (502) for analysis. Absorbent material (501) positioned after the reaction chambers (502) helps to draw the sample fluid from the sample preparation chamber (202) into the reaction chambers (502). Reaction chambers may contain reagents, reagent tablets, reagent disks, or indicator inserts, as described herein.

In so far as liquid phase tests are desired, they may be conducted using a variety of means but ultimately rely on the formation of a visible signal in a low volume of liquid (e.g. 100 μL). The methods differ in terms of how one acquires, dilutes and introduces the sample. In this example, we introduce the sample using an adapted syringe-like configuration. The sample may be a swab, piece of gauze or contaminated thread from a dressing. The swab (FIG. 35) is placed in a plunger configuration and then the plunger forms a handle with which the swab can be mixed with an extraction buffer or a diluent in a sample preparation chamber. The plunger then allows the removal of fluid by sealing against the stem of the swab and the sides of the chamber simultaneously; a goretex insert in the plunger allows gas removal as the plunger descends. Where the sample is a thread or piece of gauze, the swab is replaced by a hook, however, the principle is the same as the stem of the hook is placed within the plunger.

The sample preparation chamber contains buffer which is mixed with the sample on the swab/hook. The chamber is sealed at the Luer-Lock style connector and this seal is broken either when the Luer is placed in a receptacle, or when the swab or hook is pushed through the bottom of the chamber (FIG. 35). The assay device entrance includes a standard female Luer with a Luer lock like surround to ensure good sealing. The modified chamber engages irreversibly with the female Luer lock and on depression of the plunger, the fluid is transferred gas free into the device via a fluid distribution network. Each chamber in the device contains a reagent tablet (see previous example for the reagents). Each chamber is vented via a goretex patch sonic welded over the chamber. As soon as the chamber is filled (from bottom to top), fluid flow preferably stops. The vented gas passes by a filter before reaching the atmosphere. The arrival of fluid dissolves the reagent pills and allows the reaction to start. The degree of reaction over a given time is determined by comparison to a chart of colors. The result is largely binary, clear color or not. The more markers associated with color, the more likely the potential infection. Thus, wound fluids from uninfected wounds do not cause color change. Those from infected wounds cause at least one marker to change color and more often all three markers within 5 minutes.

FIG. 38 shows one embodiment of a diagnostic device or a transfer system, comprising a chamber or vessel (601) containing a buffer, such as saline, a resealable top (600), a plunger or similar device (602) with a gas outlet and a hook or sample tip at one end for transferring sample into the a sample preparation chamber or a diluent chamber (601), and at least one reaction chamber (606) capable of analyzing a sample fluid from the chamber (601). To conduct such analysis, the plunger or piston (602) containing a sample at the end is inserted into the sample preparation chamber (601), or a sample is placed in the diluent chamber (601), so that the sample may be diluted or dissolved in the buffer in the chamber (601). The assembly of a plunger (602) inserted in a diluent chamber (601) is shown in (607).

The chamber (601) may further comprise a Luer-Lock or slip tip (605) for connecting to a reaction chamber (604) or an analysis system. After connecting plunger unit (601, 602) to reaction chamber (604), one may depress the plunger (602) downward to break a seal at the end of the chamber (601), releasing sample fluid from the sample preparation chamber into reaction chambers (604), wherein individual reaction chamber (606) may have a different reporter or color system for detecting an analyte. The plunger (602) can further comprise membrane that pushes water and lets out gas, thus degassing the sample fluid as one depresses the plunger into the chamber. The reaction chambers may be filled in parallel, and the last chamber contains an aerosol filter and a pressure exit to atmosphere. Pressure, equalization, reaction chamber filling and aerosol filtering can be achieved through membrane exits. In some embodiments, reaction chambers contain reagent tablets or reagent disks. Top membranes can be welded in place using ultrasound. Lenses that enlarge the view of the reaction chambers are used in some embodiments. The connection to the reaction chamber or transfer system (604) includes a rough filter and a penetrator for breaking the buffer seal on connection at 605. Reaction chambers can be closed at the top and bottom by clipping on.

The conformation of the reaction vessels can be flexibly organized. One example is shown in FIG. 39, which shows another embodiment of an analysis system (604). Reaction chambers (606) can be arranged in a radial manner instead of in a linear arrangement. A fan- or radial-shaped analysis system (604) is adapted to use with a sample preparation chamber (601) with a plunger (602) system for driving a sample solution into reaction wells or chambers. Different views of such analysis system (604) are shown in (B). (608) shows a top view of a series of reaction chambers arranged in a radial arrangement. In some embodiments, the reaction chamber unit (610) may be removable from housing (609). This removable feature facilitates a user in refilling, inserting, or exchanging reagents in individual reaction chambers within the reaction unit (610).

In this example, the reagents used are water soluble and are formulated as tablets using excipients such as PEG, maltose and sorbitol as carriers. The tablets are formulated with the appropriate amounts of buffer salts in the bulk mixture to result in optimal pH upon dissolution. For supply of hydrogen peroxide, sodium percarbonate is used. As an MPO substrate, a soluble Fast Blue derivative, i.e the product of reaction with succinic anhydrice, is used, alternatively, guacol, diamino phenol or similar may be used. For Elastase, AAPV nitrophenol amide is employed, alternatively, AAPV-indoxyl with a diazonium salt enhancer. For Lysozyme, the substrate is a labelled peptidoglycan particle, however, the well contains a positively charged membrane at the viewing interface. This membrane is derived on one half with the trap, and the contrast between the two sides in the main indicator of reaction indicates the degree of reaction.

In some embodiments, such as FIG. 24, sampling threads (100) are built in or added to dressing for a wound or at a surgical site (92). AQUACEL (4) is used in some embodiments of the dressing (92). Sampling threads absorb wound fluid or fluid at surgical site (D). A thread may be pulled out or extracted as shown in FIG. 24(E) from dressing without having to remove or disturb dressing using an instrument (101) such as a tweezer, hook, or thread hook device. The thread can then be dissolved in a buffer for use in a diagnostic device (102) using one or more indicator regents or indicator disks described herein.

In some embodiments, a wound dressing comprises built in sampling threads. In some embodiments, the sampling threads absorb wound fluids and may be removed without disturbing the wound dressing for detection of analytes in the wound fluid.

In some embodiments, the sample threads may be diluted in buffer to dissolve markers for diagnosing the status of the surgical site or wound.

In some embodiments, a thread hook device may be used to remove a thread from a wound dressing.

While preferred embodiments of the disclosed technology have been shown and described herein, it will be obvious to those skilled in the art that such embodiments are provided by way of example only. Numerous variations, changes, and substitutions will now occur to those skilled in the art without departing from the disclosed technology. It should be understood that various alternatives to the embodiments of the disclosed technology described herein may be employed in practicing the disclosed technology. It is intended that the following claims define the scope of the disclosed technology and that methods and structures within the scope of these claims and their equivalents be covered thereby.

The invention claimed is:

1. A wound dressing comprising:
   a) a wound contacting layer;
   b) a reagent layer comprising one or more testing regions, wherein the reagent layer is in fluid communication with the wound contacting layer; and
   c) an outer layer that overlays the reagent layer,
   wherein the one or more testing regions comprise a leach-back trap in fluid communication with a reagent pad and one or more lines of wicking stitching or wicking tufting crossing through the one or more testing regions only at the leach-back trap.

2. The wound dressing of claim 1, wherein each of the one or more testing regions includes one or more of a back-flow trap, the reagent pad, a filter pad, an indicator trap, and an absorbent area, and wherein when the one or more testing regions includes the reagent pad or the indicator, one or more viewing windows are located either above the reagent pad or the indicator trap.

3. The wound dressing of claim 2, wherein when each of the one or more testing regions includes the reagent pad, the filter pad, the indicator trap, and the absorbent area:
 a) the reagent pad is in fluid communication with the filter pad;
 b) the filter pad is in fluid communication with the indicator trap; and
 c) the indicator trap is in fluid communication with the absorbent area.

4. The wound dressing of claim 1, wherein each of the one or more testing regions comprises one or more reagents selected from the group consisting of enzyme-reactive indicators, reagents that are sources of peroxide, enzymes that produce colored products, pH indicators, protein responsive reagents, and moisture-detecting reagents;
 wherein the enzyme-reactive indicators are protein indicator conjugates;
 wherein the protein indicator conjugates have the structure of Formula (I):

$$A\text{-}B \quad \text{Formula (I)}$$

wherein:
 A is an anchor region or moiety that attaches an enzyme-reactive region to the reagent pad covalently, non-covalently, or ionically; and
 B is the enzyme-reactive region.

5. The wound dressing of claim 4, wherein when each of the one or more testing regions includes enzyme-reactive indicators, B further comprises an indicator region having an enzyme reaction indicator.

6. The wound dressing of claim 5, wherein the indicator region is configured to be cleaved by a target enzyme and transformed into a colored species by accessory enzymes selected from the group consisting of lipase, esterase, hexosaminidase, peroxidase, oxidase, glycosidase, glucosidase, laccase, and a combination of two or more thereof.

7. The wound dressing of claim 5, wherein the enzyme-reactive indicators are configured for interaction with one or more enzymes selected from the group consisting of elastase, lysozyme, cathepsin G, myeloperoxidase, and any combination thereof.

8. The wound dressing of claim 5, wherein the enzyme-reactive indicators comprise a moiety capable of producing a visible color or a detectable electronic change upon interaction of an enzyme-labile or enzyme-reactive region with one or more enzymes, wherein the moiety is selected from the group consisting of a peroxidase substrate, arylamine, an amino phenol, a neutral dye, a charged dye, a nanoparticle, a colloidal gold particle, and an analog thereof.

9. The wound dressing of claim 1, further comprising a foam layer between the wound contacting layer and the reagent layer.

10. The wound dressing of claim 9, further comprising one or more perforations in the wound contacting layer.

11. The wound dressing of claim 1, wherein the leach-back trap is in fluid communication with one or more perforations aligned with the leach-back trap.

* * * * *